US012806046B2

(12) United States Patent
Kuniholm et al.

(10) Patent No.: US 12,806,046 B2
(45) Date of Patent: Nov. 24, 2026

(54) PROSTHETIC DEVICES, SYSTEMS INCLUDING THE SAME, AND RELATED METHODS

(71) Applicant: Stumpworx LLC, Portland, OR (US)

(72) Inventors: Jonathan Kuniholm, Portland, OR (US); Zachary Meyer, Portland, OR (US)

(73) Assignee: Stumpworx LLC, Portland, OR (US)

( * ) Notice: Subject to any disclaimer, the term of this patent is extended or adjusted under 35 U.S.C. 154(b) by 733 days.

(21) Appl. No.: 18/307,203

(22) Filed: Apr. 26, 2023

(65) Prior Publication Data

US 2023/0255803 A1 Aug. 17, 2023

Related U.S. Application Data

(63) Continuation-in-part of application No. 17/494,828, filed on Oct. 5, 2021, now Pat. No. 11,950,685, and (Continued)

(51) Int. Cl.

*A61F 2/80* (2006.01)
*A61F 2/50* (2006.01)
*A61F 2/78* (2006.01)

(52) U.S. Cl.

CPC .............. *A61F 2/80* (2013.01); *A61F 2/5046* (2013.01); *A61F 2002/503* (2013.01);

(Continued)

(58) Field of Classification Search

CPC ...... A61F 2/54; A61F 2/78; A61F 2/80; A61F 2002/5026; A61F 2002/5027;

(Continued)

(56) References Cited

U.S. PATENT DOCUMENTS 999,484 A 8/1911 Carnes
1,173,219 A 2/1916 Rowley (Continued)

FOREIGN PATENT DOCUMENTS

AT 273362 B * 8/1969
CA 2304743 A1 11/2000

(Continued)

OTHER PUBLICATIONS

Alley et al., "Prosthetic Sockets Stabilized by Alternating Areas of Tissue Compression and Release," 48 JRRD. 679-96 (2010).

(Continued)

*Primary Examiner* — Christie Bahena
(74) *Attorney, Agent, or Firm* — Kolitch Romano Dascenzo Gates LLP

(57) ABSTRACT

A prosthetic device for engaging a residual limb includes a plurality of elongate counters configured to receive at least a portion of the residual limb within a volume defined by the plurality of elongate counters. Each respective elongate counter is configured to counteract forces applied to the residual limb via the prosthetic device. The prosthetic device also includes a socket and a selective adjustment system, and may include an independent counter engaged with the socket. The socket is configured to engage with the residual limb, and may include a lower textile socket coupled to the plurality of elongate counters and an upper textile socket coupled to the lower textile socket. The selective adjustment system is configured to secure the prosthetic device to the residual limb and to provide selective adjustment of compression of the socket and the plurality of elongate counters around the residual limb.

37 Claims, 35 Drawing Sheets

Related U.S. Application Data a continuation-in-part of application No. 16/974,120, filed on Oct. 5, 2020, now Pat. No. 11,672,678.

(60) Provisional application No. 63/370,790, filed on Aug. 9, 2022, provisional application No. 63/370,446, filed on Aug. 4, 2022, provisional application No. 62/911,232, filed on Oct. 5, 2019.

(52) U.S. Cl.
CPC . *A61F 2002/5038* (2013.01); *A61F 2002/505* (2013.01); *A61F 2002/7862* (2013.01)

(58) Field of Classification Search
CPC .......... A61F 2002/503; A61F 2002/543; A61F 2002/5083; A61F 2002/509; A61F 2002/546; A61F 2002/7812; A61F 2002/7818; A61F 2002/7862
See application file for complete search history.

(56) References Cited

U.S. PATENT DOCUMENTS

| | | | | |
|---|---|---|---|---|
| 1,206,753 | A | 11/1916 | Desmore | |
| 1,263,675 | A | 4/1918 | Jeffery | |
| 1,277,747 | A | 9/1918 | O'Connor | |
| 1,285,326 | A | 11/1918 | Nelson | |
| 1,507,683 | A | 9/1924 | Pecorella et al. | |
| 1,989,960 | A | 2/1935 | Wheeler et al. | |
| 2,333,009 | A * | 10/1943 | Hosmer | A61F 2/54 623/65 |
| 2,409,884 | A | 10/1946 | Mollenhour | |
| 2,494,646 | A | 1/1950 | Crawshaw | |
| 2,554,237 | A | 5/1951 | Blackburn | |
| 2,668,959 | A | 2/1954 | Sargeson | |
| 2,793,368 | A | 5/1957 | Nouel | |
| 3,434,469 | A | 3/1969 | Swift | |
| 3,905,503 | A | 9/1975 | Fraze | |
| 4,125,904 | A | 11/1978 | Levine | |
| 4,258,441 | A | 3/1981 | Bell | |
| 5,018,652 | A | 5/1991 | Holtzclaw, Jr. | |
| 5,181,638 | A | 1/1993 | Mchale | |
| 5,765,735 | A | 6/1998 | Kimchi et al. | |
| 5,961,019 | A | 10/1999 | Gleason et al. | |
| 6,793,112 | B2 | 9/2004 | Ammerman | |
| 7,198,610 | B2 | 4/2007 | Ingimundarson et al. | |
| 7,431,184 | B2 | 10/2008 | Gregory | |
| 7,743,885 | B2 | 6/2010 | Martin et al. | |
| 8,323,353 | B1 | 12/2012 | Alley et al. | |
| 8,821,588 | B2 | 9/2014 | Latour | |
| 8,978,224 | B2 | 3/2015 | Hurley et al. | |
| 8,998,053 | B2 | 4/2015 | Cromie et al. | |
| 9,044,349 | B2 | 6/2015 | Hurley et al. | |
| 9,180,027 | B2 * | 11/2015 | Kettwig | A61F 2/70 |
| 9,283,093 | B2 | 3/2016 | Alley | |
| 9,486,031 | B2 | 11/2016 | Dua et al. | |
| 9,549,828 | B2 | 1/2017 | Hurley et al. | |
| D778,452 | S | 2/2017 | Cespedes et al. | |
| 9,581,414 | B1 | 2/2017 | Mironski | |
| 9,750,643 | B2 | 9/2017 | Convert et al. | |
| 10,123,888 | B2 | 11/2018 | Alley et al. | |
| 10,159,592 | B2 | 12/2018 | Ingimundarson et al. | |
| 10,179,056 | B2 | 1/2019 | Hurley et al. | |
| 10,278,837 | B1 | 5/2019 | Martin | |
| 10,369,027 | B2 | 8/2019 | Alley | |
| 10,543,112 | B2 | 1/2020 | Bache et al. | |
| 11,168,416 | B2 | 11/2021 | Huffa et al. | |
| 11,470,889 | B2 | 10/2022 | Huffa et al. | |
| 2004/0185247 | A1 | 9/2004 | Fenton et al. | |
| 2005/0131322 | A1 | 6/2005 | Harris et al. | |
| 2007/0007314 | A1 | 1/2007 | Lin | |
| 2007/0245526 | A1 | 10/2007 | Fidrych et al. | |
| 2008/0142557 | A1 | 6/2008 | Hess et al. | |
| 2011/0071647 | A1 | 3/2011 | Mahon | |
| 2011/0208321 | A1 | 8/2011 | Doddroe et al. | |
| 2012/0101597 | A1 | 4/2012 | Bache | |
| 2012/0141750 | A1 | 6/2012 | Taylor | |
| 2013/0103166 | A1 * | 4/2013 | Butler | A61F 2/7812 623/36 |
| 2014/0121783 | A1 | 5/2014 | Alley | |
| 2015/0032041 | A1 | 1/2015 | Ingimundarson et al. | |
| 2015/0366678 | A1 | 12/2015 | Edwards et al. | |
| 2017/0000216 | A1 | 1/2017 | Dua et al. | |
| 2017/0128238 | A1 | 5/2017 | Hurley et al. | |
| 2017/0143518 | A1 * | 5/2017 | Hurley | A61F 2/76 |
| 2017/0151072 | A1 | 6/2017 | Mahon et al. | |
| 2018/0214284 | A1 | 8/2018 | Wagner et al. | |
| 2019/0200693 | A1 | 7/2019 | Bishop | |
| 2020/0163783 | A1 | 5/2020 | Martin | |
| 2020/0345521 | A1 | 11/2020 | Mahon et al. | |
| 2022/0062014 | A1 | 3/2022 | Martin | |
| 2022/0282410 | A1 | 9/2022 | Dua et al. | |
| 2023/0038383 | A1 | 2/2023 | Dua et al. | |
| 2023/0088406 | A1 | 3/2023 | Mahon | |

FOREIGN PATENT DOCUMENTS

| | | | | |
|---|---|---|---|---|
| CA | 2325607 | A1 | 5/2002 | |
| CN | 115734720 | A | 3/2023 | |
| DE | 102014220087 | B4 | 5/2016 | |
| EP | 3178342 | A1 | 6/2017 | |
| EP | 3508628 | A1 | 7/2019 | |
| EP | 3567146 | A1 | 11/2019 | |
| ES | 2642964 | T3 | 11/2017 | |
| GB | 191118428 | A * | 3/1912 | A61F 2/54 |
| GB | 105262 | A * | 4/1917 | A61F 2/588 |
| JP | 2022081489 | A | 5/2022 | |
| WO | 2006138388 | A2 | 12/2006 | |
| WO | 2018144736 | A1 | 8/2018 | |

OTHER PUBLICATIONS

Fryer, Charles M., "Upper-Limb Prosthetics: Harnessing and Controls for Body-Powered Devices," 6B Atlas of Limb Prosthetics: Surgical, Prosthetic, and Rehabilitation Principles, 2ed. American Academy of Orthopedic Surgeons, Rosemont, IL (2002).

Mutnick, Ally, "McCormick Freshman Design Prosthetic Arms for Amputee Patients," The Daily Northwestern (Jan. 9, 2013), https://dailynorthwestern.com/2013/01/09/campus/mccormick-freshmen-design-prosthetic-arms-for-amputee-patients/.

Miguelez et al., "The Transradial Anatomically Contoured (TRAC) Interface: Design Principles and Methodology," 15 JPO. 148-57 (2003).

Paterno et al., "Sockets for Limb Prostheses: A Review of Existing Technologies and Open Challenges," 65 IEEE. 1996-2010 (Sep. 2018).

Sokolowski et al., "A Product Design Approach to Prosthetic Design: A Case Study," 3304 DMD Proc (2019).

Taylor, Craig. L., "The Biomechanics of Control in Upper-Extremity Prostheses," 2, 3 Artificial Limbs 4-25 (1955).

Wang et al., "Physical and Mechanical Testing of Textiles," Fabric Testing, 4, 90-124 (Dec 2008).

Wikipedia Encyclopedia, "Breathability," http.wikipedia.com/breathability, (Nov. 2, 2022).

Machine-generated English language translation of Spanish Patent No. ES2642964T3, issued Nov. 20, 2017.

The Science Museum Group, "Artificial Right Leg," 1999-471, Orthopaedics, Richmond Twickenham and Roehampton Healthcare NHS Trust, New York, United States (1910-1914).

Fillauer LLC, "WD Quick Change Wrist" product page, (Apr. 18, 2023) https://fillauer.com/products/wd-quick-change-wrist/.

Machine-generated English language translation of Japanese Patent Application Publication No. JP2022081489A, published May 31, 2022.

Machine-generated English language translation of Chinese Patent Application Publication No. CN115734720A, published Mar. 3, 2023.

Machine-generated English language translation of German Patent No. DE102014220087B4, issued May 12, 2016.

(56) References Cited

OTHER PUBLICATIONS

Kuniholm et al., "Functionally Viable 3D Printed Polymer Transradial Frame and Wrist with Variable Compliance Dynamic Volume Soft Socket with Increased Breathability and Range of Motion," Stumpworx LLC (Aug. 9, 2022).
Kuniholm et al., Stumpworx LLC, "Functionally Viable 3D Printed Polymer Transradial Frame and Wrist with Variable Compliance Dynamic vol. Soft Socket with Increased Breathability and Range of Motion" Presentation, Fredericton, NB, CA (Aug. 9, 2022).
Kuniholm, Jonathan, International Society for Prosthetics and and Orthotics, "Variable Compliance Transradial Prosthetic Socket Allowing Full Anatomical Range of Motion Using Stiff Motion Counters in a Breathable Soft Matrix" presentation, 17th World Congress, Kobe Convention Center, Kobe, Hyogo, Japan (Oct. 8, 2019).
International Society for Prosthetics and and Orthotics, 17th World Congress Abstract Book, "Prosthetics and Orthotics International" 43.1, p. 433, Kobe, Hyogo, Japan (Sep. 30, 2019).
Nash, Zachary, Pensole Footwear Design Academy, "This is Jake" presentation, IFN Platform Challenge, 10 NW 5th Avenue, Portland, Oregon 97209 (Jun. 26, 2015).
Openprosthetics.org, Kuniholm, Jonathan, "The Open Prosthetics Socket: A Variable Compliance Prosthetic Socket with Stiff Motion Counters in a Soft Sock Matrix," https://web.archive.org/web/20180816001714/https:/www.openprosthetics.org/projects/jkuniholm/open-prosthetics-socket-variable-compliance-prosthetic-socket-stiff-motion (Aug. 16, 2018).

* cited by examiner

PROSTHETIC DEVICES, SYSTEMS INCLUDING THE SAME, AND RELATED METHODS

RELATED APPLICATIONS

This application is a continuation-in-part of U.S. Non-Provisional patent application Ser. No. 16/974,120, entitled "VARIABLE COMPLIANCE PROSTHETIC SOCKET WITH BREATHABLE MATRIX," which was filed on Oct. 5, 2020, and claims priority to U.S. Provisional Patent Application No. 62/911,232, entitled "VARIABLE COMPLIANCE JOINT-TRANSITING SOFT PROSTHETIC SOCKET," which was filed on Oct. 5, 2019, the complete disclosures of which are incorporated herein by reference. This application also claims priority to U.S. Provisional Patent Application No. 63/370,790, entitled "PROSTHETIC LIMB WITH INTEGRATED POLYMER FRAME, WRIST, AND VARIABLE COMPLIANCE DYNAMIC VOLUME SOFT SOCKET WITH INCREASED BREATHABILITY AND RANGE OF MOTION," which was filed on Aug. 9, 2022, the complete disclosure of which is incorporated herein by reference. This application also claims priority to U.S. patent application Ser. No. 17/494,828, entitled "PRESSURE-RELIEVING FLEXURAL LOAD BEARING STRAP AND METHOD FOR MANUFACTURING THE SAME," which was filed on Oct. 5, 2021, and U.S. Provisional Patent Application No. 63/370,446, entitled "PRESSURE RELIEVING FLEXURAL LOAD BEARING COMPONENT AND METHOD FOR MANUFACTURING SAME," which was filed on Aug. 4, 2022, the complete disclosures of which are incorporated herein by reference.

FIELD

The present disclosure relates generally to limb prostheses, and more particularly to prosthetic devices including features of a variety of stiffnesses.

BACKGROUND

Among the general population, nearly half of all arm amputees either reject or have never worn a prosthetic arm. While leg amputees are more likely to accept prostheses, they have similar complaints about conventional prosthetic devices. Dissatisfaction often stems from discomfort resulting from contact between the residual limb and the prosthetic suspension or interface (i.e., the point of attachment to the body) and/or from a lack of function once attached to the residual limb. Specifically, conventional prosthetic devices have shortcomings involving the security and comfort of the attachment to the residual limb, the resulting weight-bearing tolerance when using the conventional prosthetic device to bear weight in compression or tension, heat and moisture management, the range of motion being restricted due to the use of rigid sockets, and the accuracy of transmission of motion via the conventional prosthetic device.

Conventional prosthetic devices have attempted to produce self-suspending sockets, which are designed to be secured to the residual limb without requiring use of a harness, as conventional harnesses are often seen as a source of discomfort and/or inconvenience. However, existing solutions either utilize a hard socket that restricts mobility and provides poor moisture management, or a suction sleeve and pin lock with their own disadvantages. Conventional self-suspended sockets have difficulty securing the prosthetic device against forces resulting from the amputee's use of their residual limb. For example, extended arm tensile loads in conventional supracondylar prosthetic devices may create uncomfortable pressure against the epicondyles of the residual limb, can generally slip off the residual limb at certain angles of extension, and generally restrict the patient's range of motion. Transverse loads, either by force directed by the residual limb against an object or from a load supported by the terminal device of the prosthesis, exert force on the prosthetic device and ultimately, the residual limb inside the socket. Conventional prosthetic devices utilize sockets that transfer forces from the residual limb to a terminal device as directly as possible. Movement of the residual limb in the socket and movement of the bone (which displaces soft tissue in the residual limb) results in undesired movement of the residual limb relative to the terminal device. The prior art sockets thus fail to sufficiently meet the competing demands of resisting movement of the socket relative to the residual limb, while at the same time allowing sufficient range of motion of the most distal joint.

While the majority of amputees use body-powered prosthetic devices, current conventional research and development efforts in prosthetic arm design are focused mainly on powered robotic movement and the various control improvements. However, both body-powered and robotic prosthetic devices must create an interface between the socket and the residual limb, and all conventional solutions have drawbacks in comfort and/or efficiency of movement. In the specific case of transradial amputations, encroachment into the area of the socket that covers the patient's cubital fold area directly limits the range of motion of the residual limb. Transradial prosthetic devices also must contend with the added challenge of approximating the high degree of stretch of the skin surface at the elbow during flexion of the residual limb in these cases. Thus, there remains a need for an improved prosthetic device that addresses the disadvantages and inefficiencies of conventional prosthetic devices.

SUMMARY

Presently disclosed prosthetic devices may address the above-detailed shortcomings and other disadvantages of prior art prosthetic devices. Generally, disclosed prosthetic devices include a combination of components with different degrees of stiffness and compliance, such as rigid or semi-rigid counters, a socket that engages the residual limb, and a plurality of laces or cables. Together, these components provide compression and suspension for a secure and comfortable attachment to the residual limb that preserves anatomical range of motion of the residual limb and its joint or joints. Components of disclosed prosthetic devices may function together as a dynamic and synergistic structure, together providing suspension in a way that no single component can by itself, with the overall effect potentially being greater than the sum of its parts. Components of disclosed prosthetic devices may be configured to cross one or more joints of the body when the prosthetic device is worn, without interfering with the patient's comfort or anatomical range of motion of the residual limb.

In examples, a disclosed prosthetic device may include a plurality of elongate counters and/or other counters, a socket, and a selective adjustment system. The plurality of elongate counters may extend proximally from a chassis and may be configured to receive at least a portion of the residual limb within a volume defined by the plurality of elongate counters. Each respective elongate counter of the plurality of elongate counters may be configured to counteract forces applied to the residual limb via the prosthetic device. The socket may be configured to engage with the residual limb, and may include a lower textile socket and an upper textile socket. The lower textile socket may be coupled to the plurality of elongate counters, and the upper textile socket may be coupled to the lower textile socket. In some examples, the upper textile socket also is coupled to one or more independent counters, such as a proximal counter. The selective adjustment system may be configured to secure the prosthetic device to the residual limb and provide selective adjustment of compression of the socket around the residual limb.

In examples, a disclosed prosthetic device may include a plurality of elongate counters and/or other counters, a socket configured to engage with the residual limb, and a selective adjustment system. The plurality of elongate counters may extend proximally from a chassis and may be configured to receive at least a portion of the residual limb within a volume defined by the plurality of elongate counters. One or more independent counters may be attached to any part of the socket and be similarly configured to receive at least a portion of the residual limb. Each respective elongate or independent counter may be configured to counteract forces applied to the residual limb via the prosthetic device. The selective adjustment system may be configured to secure the prosthetic device to the residual limb and provide selective adjustment of compression of the socket and counters around the residual limb. The selective adjustment system may include at least one fixed line having a predetermined length, and at least one lace having a selectively adjustable length.

Disclosed systems may include a disclosed prosthetic device and a harness configured to be worn by a patient while the prosthetic device is worn. The harness may be coupled to the prosthetic device to reinforce securement of the prosthetic device to the residual limb. The harness may include at least one portion comprising a stretch material (e.g., a stretch fabric) and at least a second portion comprising a non-stretch material (e.g., a non-stretch fabric).

Methods of making prosthetic devices also are within the scope of the present disclosure. Methods may include performing a 3D-scan of the given residual limb, creating a computer-aided design (CAD) model of the given residual limb, forming a plurality of elongate counters and/or an independent, or proximal, counter, and forming a plurality of textile pattern pieces to form a socket of the prosthetic device. For example, forming the plurality of elongate counters and the independent counter may be performed using the CAD model of the given residual limb. The plurality of elongate counters and the independent counter may be custom-sized and shaped for the given residual limb (e.g., may be patient-specific). The plurality of textile pattern pieces may be used to form an upper textile socket and a lower textile socket, which may be coupled together to form the socket. The plurality of textile pattern pieces may be custom-sized and shaped for the given residual limb using the CAD model of the given residual limb.

DESCRIPTION

Figure 1:
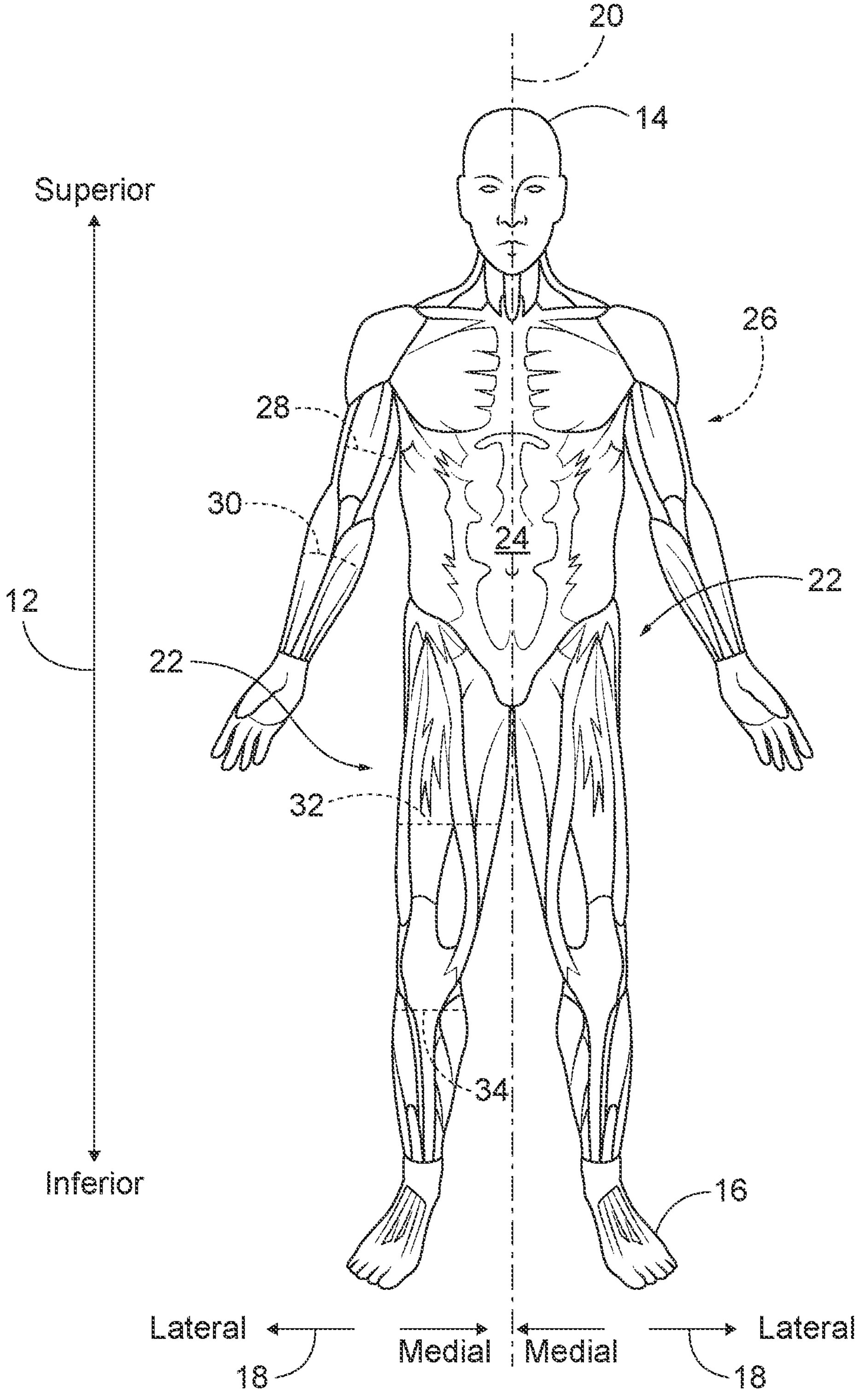
FIG. 1 is a reference figure to establish reference terminology used herein.

FIG. 1 provides a general reference framework for discussion of presently disclosed prosthetic devices herein, illustrating the general reference direction indications for a patient 10, or other wearer, of the disclosed prosthetic devices. As indicated by arrow 12, a first component or feature of the disclosed prosthetic devices may be described as being superior relative to another component or feature, or relative to an aspect of patient 10, if the first component or feature is closer to the head 14 of patient 10. Similarly, a first component or feature of the disclosed prosthetic devices may be described as being inferior relative to another component or feature, or relative to an aspect of patient 10, if the first component or feature is closer to the feet 16 of patient 10.

As indicated by arrows 18, a first component or feature of the disclosed prosthetic devices may be described as being lateral to another component or feature, or to an aspect of patient 10, if the first component or feature is closer to a side 22 of patient 10 than the other component or feature. Likewise, a first component or feature of the disclosed prosthetic devices may be described as being medial to another component or feature, or to an aspect of patient 10, if the first component or feature is closer to an imaginary centerline 20 of patient 10 than the other component or feature. Put another way, a first component or feature is medial to a second component or feature if the first component or feature is closer to imaginary centerline 20 than the second component or feature is, whereas a first component or feature is lateral to a second component or feature if the first component or feature is closer to a given side 22 than the second component or feature. Thus, generally, if a first component or feature is lateral to a second component or feature, then the second component or feature will likewise be medial to the first component or feature.

Reference will also be made herein to an anterior, or front, side 24, which may refer to anterior side 24 of patient 10 and/or to components or features of disclosed prosthetic devices that are configured to be positioned on anterior side 24 of patient 10, and/or anteriorly to another component or feature of disclosed prosthetic devices (e.g., closer to anterior side 24). Posterior, or back, side 26 may refer to posterior side 26 of patient 10 and/or to components or features of disclosed prosthetic devices that are configured to be positioned on posterior side 26 of patient 10, and/or posteriorly to another component or feature of disclosed prosthetic devices (e.g., closer to posterior side 26).

Reference will also be made herein to components being proximal or distal to one another. As used herein, the term "proximal" means nearer to the center of the body or point of attachment, and the term "distal" means situated further away from the center of the body or the point of attachment. Thus, the shoulder is proximal to the wrist and elbow, the wrist is distal to the elbow and shoulder, and the elbow is proximal to the wrist and distal to the shoulder. Likewise, components or features of disclosed prosthetic devices will be described as proximal or distal, or proximal or distal to one another, with reference to the residual limb that the prosthetic device is configured to engage with. Finally, reference may be made to different levels of amputation, which are schematically represented in FIG. 1 in dashed lines for transhumeral amputations (indicated at 28; above or proximal to the elbow), transradial amputations (indicated at 30; below or distal to the elbow), transfemoral amputations (indicated at 32; proximal to the knee), and transtibial amputations (indicated at 34; distal to the knee). Disclosed prosthetic devices configured for other levels of amputations also are within the scope of the present disclosure.

Figure 2:
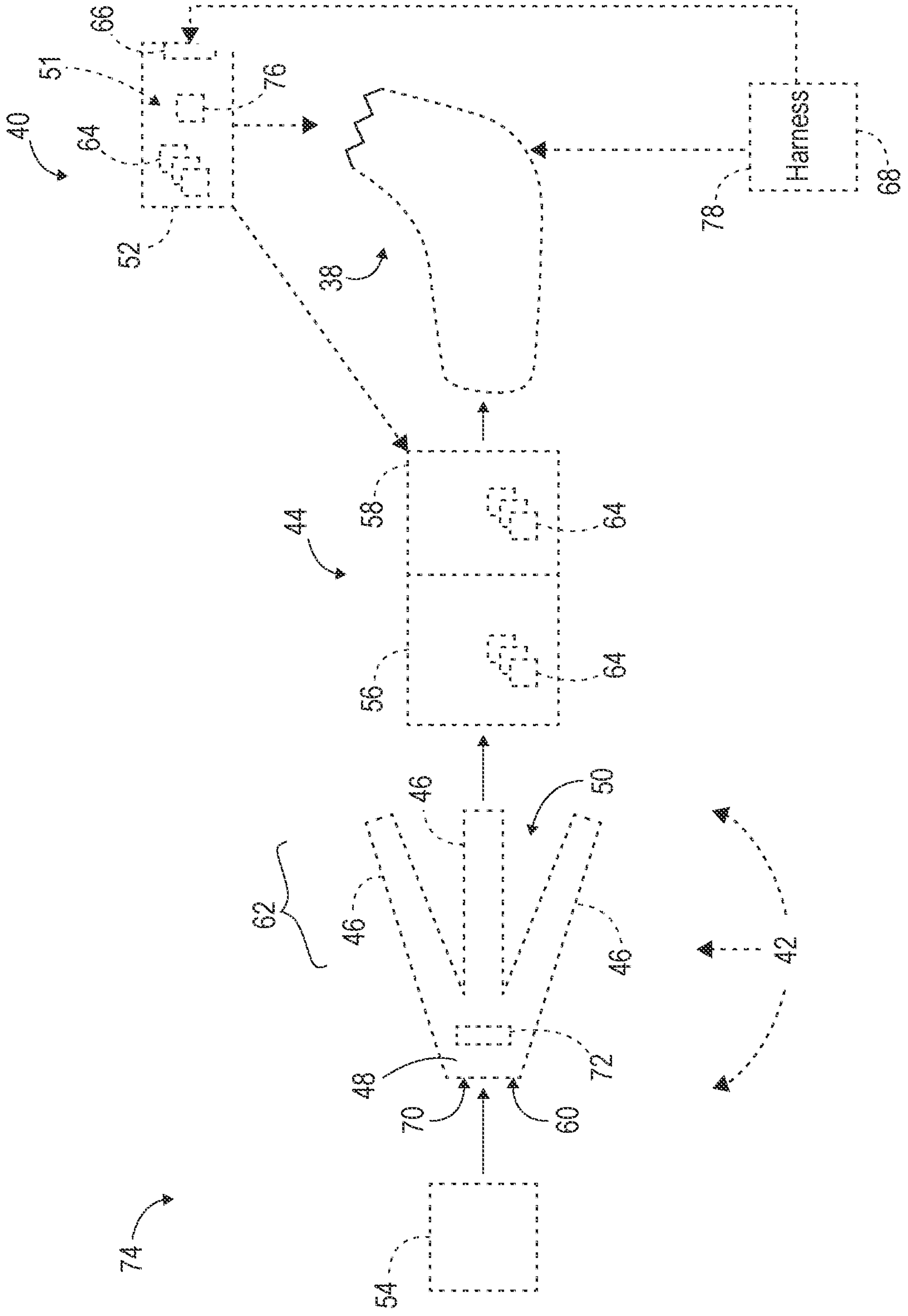
FIG. 2 is a schematic black box exploded diagram of non-exclusive examples of disclosed prosthetic devices and systems including the same.

In general, elements that are likely to be included in a given (i.e., a particular) example are illustrated in solid lines, while elements that are optional to a given example are illustrated in dashed lines. However, elements that are shown in solid lines are not essential to all examples, and an element shown in solid lines may be omitted from a particular example without departing from the scope of the present disclosure. FIG. 2 provides illustrative, non-exclusive examples of prosthetic devices 40 according to the present disclosure shown in a schematic, exploded view that is not drawn to scale. A socket 44 is configured to engage with a residual limb 38 of a patient or wearer, and to secure prosthetic device 40 to residual limb 38. Prosthetic device 40 also includes a plurality of counters 46, with counters 46 being configured to receive at least a portion of residual limb 38 within a volume 50 defined by, or between, counters 46. Each counter 46 is configured to counteract forces applied to residual limb 38 via prosthetic device 40 and generally will be rigid or semi-rigid in nature. Put another way, counters 46 may be configured to counter motion of counters 46 themselves relative to a portion of the residual limb 38. Illustrated examples of disclosed prosthetic devices 40 include counters 46 having an elongate shape. Thus, counters 46 are referred to herein as elongate counters 46, though prosthetic devices 40 may include one or more counters 46 that are not elongate. Similarly, while counters 46 are illustrated as being coupled to or integrally formed with a frame, body, or chassis 48 (e.g., extending proximally from chassis 48), prosthetic devices 40 may include additional or alternative counters 46 that do not extend from chassis 48 and/or that are not coupled to or integrally formed with chassis 48. Elongate counters 46 generally are coupled to, or integrated into, socket 44.

Elongate counters 46 may have a sufficient rigidity such that they are configured to translate motion from residual limb 38 to distal end region 60 of chassis 48 and/or to an end effector 54 attached thereto (and/or from a first joint to a second joint), while allowing some flex in key locations. For example, elongate counters 46 typically include some flexibility such that they may be drawn together around residual limb 38 by selective adjustment system 42. Materials such as nylon and/or thermoplastic polyurethane may provide suitable rigidity and flexibility for such applications. Elongate counters 46 and selective adjustment system 42 may be said to be mutually reinforcing, such that each element supports the other. Additionally or alternatively, elongate counters 46 may be configured to create a self-reinforcing connection with distal bones of residual limb 38 when elongate counters 46 are loaded. Elongate counters 46 may be integrally formed with chassis 48 or may be coupled to chassis 48.

Prosthetic device 40 also may include one or more independent counters 52 configured to engage residual limb 38. Generally independent counter 52 is not directly coupled to chassis 48 or elongate counters 46, but rather is only directly coupled to socket 44 and selective adjustment system 42 (which indirectly couple independent counter 52 to elongate counters 46). In some examples, one or more independent counters 52 may be positioned proximal to elongate counters 46, and thus may be referred to as a proximal counter 52, though additional or alternative independent counters 52 may be positioned distal to elongate counters 46. Generally, prosthetic device 40 may be configured to worn such that a joint of residual limb 38 is positioned between elongate counters 46 and independent counter 52, with elongate counters 46 positioned on one side of the joint (e.g., distal to the joint) and independent counter 52 positioned on the other side of the joint (e.g., proximal to the joint). Independent counter 52 may be coupled to socket 44 independently from elongate counters 46 (or other counters 46), and also may be configured to receive a portion of residual limb 38 within a volume 51 (best seen in the example of FIG. 15) defined by independent counter 52.

While elongate counters 46 are generally integrally formed with or coupled to chassis 48, independent counter 52 is not directly coupled to chassis 48 in some examples. Generally, independent counter 52 may be configured to resist movement of a joint of residual limb 38 (e.g., the patient's elbow) away from distal end region 60 of chassis 48. In other words, independent counter 52 may be configured to urge residual limb 38 into socket 44. Additionally or alternatively, independent counter 52 may be configured to counteract forces applied to residual limb 38 via prosthetic device 40, and transmitted to the independent counter 52 via socket 44 or selective adjustment system 42. Other functions of independent counter 52 may include creating flexible hinges with other components of prosthetic device 40, and contributing to the functionality of selective adjustment system 42. Similarly to elongate counters 46, independent counter 52 generally will be rigid or semi-rigid in nature.

Chassis 48 may be configured to receive an end effector 54, which as used herein may include an end effector, a terminal device, a prosthetic foot, a leg pylon, a gripper, and/or any tool or device that a user wishes to manipulate or use to manipulate objects via body power of residual limb 38 or via a myoelectric or neuroprosthetic interface. Selective adjustment system 42 is configured to secure prosthetic device 40 to residual limb 38 and configured to provide selective adjustment of compression of socket 44, independent counter 52, and/or elongate counters 46 around residual limb 38. In some examples, independent counter 52 includes a proximal tensioning reel 66 configured to adjust a tension of one or more laces, cables, wires, lines, or fibers of selective adjustment system 42. Independent counter 52 may be configured to be coupled to a harness 68 worn by the patient for additional suspension of prosthetic device 40. For example, independent counter 52 may include a magnetic attachment point configured for selective coupling to harness 68 worn by the patient.

Selective adjustment system 42 also may function as a suspension system that functions to provide suspension of prosthetic device 40 with respect to residual limb 38 (e.g., ensure secure attachment between prosthetic device 40 and residual limb 38). Selective adjustment system 42 may include a combination of one or more fixed lines having a predetermined or set length, and one or more adjustable laces, each having a selectively adjustable length. Overall, selective adjustment system 42 is configured to selectively adjust suspension of prosthetic device 40 via its fixed and/or adjustable lines and laces, and the interaction between selective adjustment system 42, elongate counters 46, and socket 44. Additionally or alternatively, selective adjustment system 42 may be configured to automatically adjust suspension of prosthetic device 40 in reaction to external forces applied to prosthetic device 40. For example, selective adjustment system 42 may be configured to tighten socket 44 around residual limb 38 if forces applied to a distal end region 60 of chassis 48 cause socket 44 to be pulled away from residual limb 38. To selectively adjust tension in one or more components of selective adjustment system 42, chassis 48 may include a distal tensioning reel 72, which may be in addition to or instead of proximal tensioning reel 66.

Socket 44 generally is formed at least partially of textile materials and may include textiles and/or components of varying compliances, the technical effect of which may enhance comfort, moisture management, and/or range of motion for the patient's residual limb 38, as compared to conventional prosthetic devices. Specifically, fabric materials used to form socket 44 may impart stretch, breathability, and/or moisture-wicking properties to socket 44. Socket 44 may be described as a fabric matrix, in view of the variety of different fabric or textile materials that may be combined having different degrees of stretch, to form socket 44. Socket 44 may be configured to conform to residual limb 38, move with residual limb 38, have an adaptable fit on residual limb 38, and/or remain in secure engagement with residual limb 38 in different modes of use, for different activities, and even for changes in volume of residual limb 38 (e.g., due to fluid loss, muscle mass changes, weight changes, natural movement of the limb, etc.). To this end, the interaction between socket 44 and selective adjustment system 42 may work to create a dynamic volume within socket 44, as the volume of socket 44 may be redistributed during use of prosthetic device 40 to account for changes of shape of residual limb 38 throughout its range of motion. This dynamic volume is due at least in part to the flexibility of textiles used to form socket 44, the selective adjustability of selective adjustment system 42, and changes induced in selective adjustment system 42 induced by motion of residual limb 38. Such disclosed sockets 44 may also result in improved suspension or attachment to residual limb 38, and/or improved transmission of motion from residual limb to end effector 54, due to the ability of socket 44 and selective adjustment system 42 to conform to and create a dynamic volume around residual limb 38. Additionally or alternatively, prosthetic device 40 may be configured to avoid predetermined portions, or areas, of residual limb 38 so as to preserve the range of motion residual limb 38. For example, in the example of transradial amputations, prosthetic device 40 may be configured such that elongate counters 46 and independent counter 52 avoid impingement of the cubital fold region of residual limb 38, as such impingement from rigid or semi-rigid structures, or even volume limitation from non-stretch textiles, can significantly limit flexion of the elbow.

Figure 3:
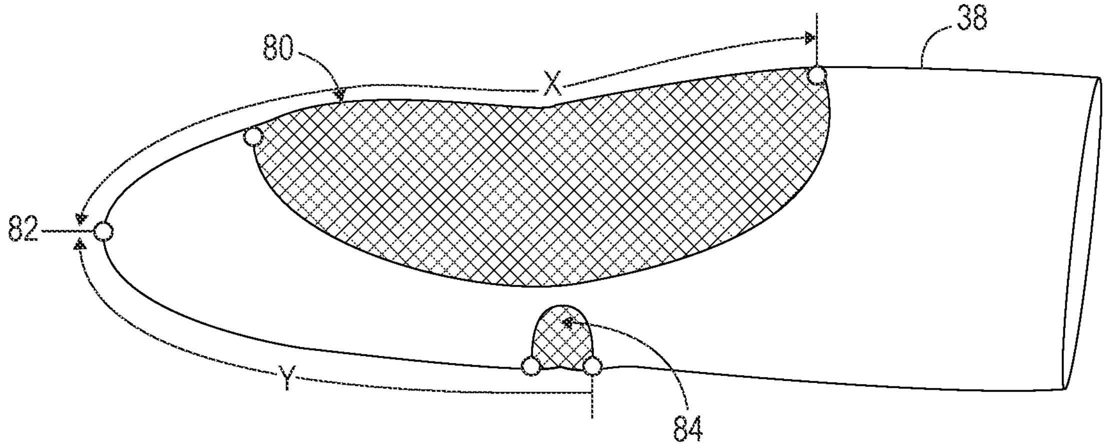
FIG. 3 is a schematic reference illustration showing an elevation view of a residual limb at extension.
Figure 4:
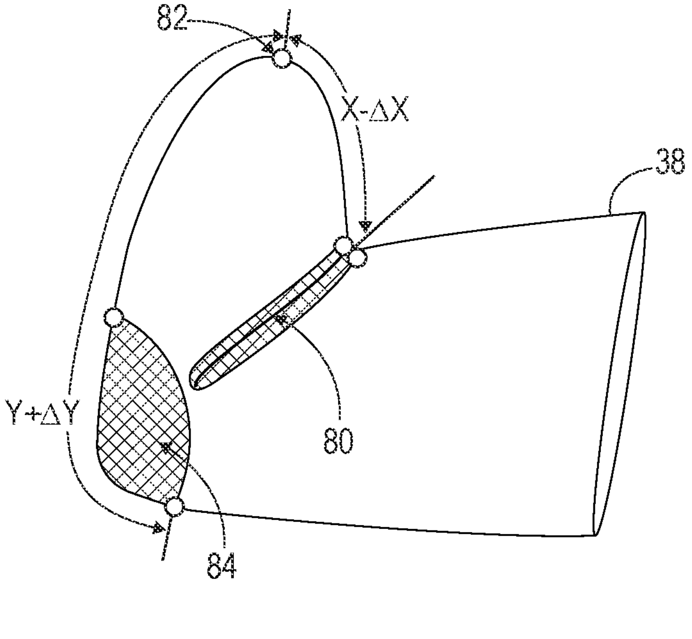
FIG. 4 is a schematic reference illustration showing an elevation view of a residual limb at flexion.
Figure 5:
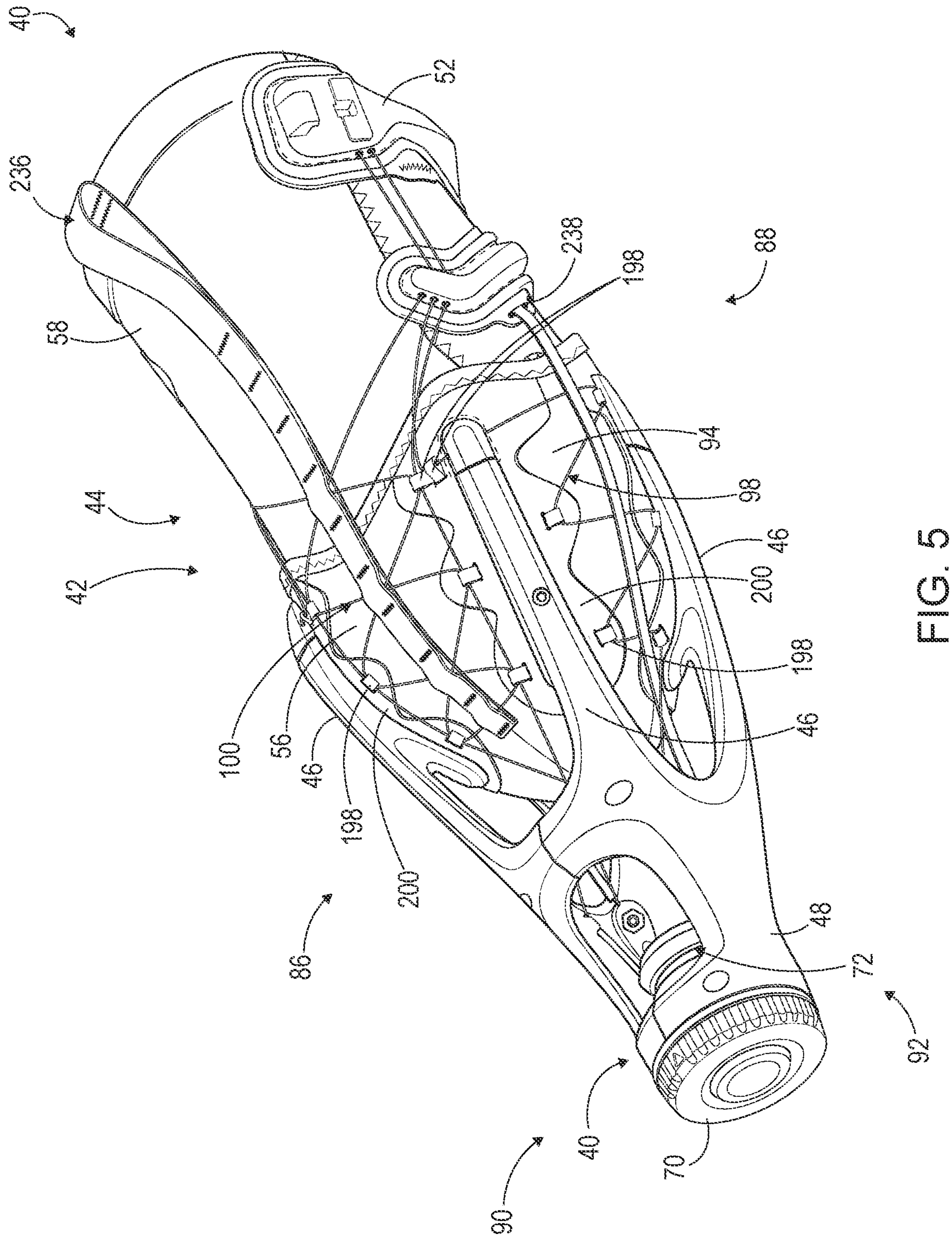
FIG. 5 is an isometric view of an example of disclosed prosthetic devices.
Figure 6:
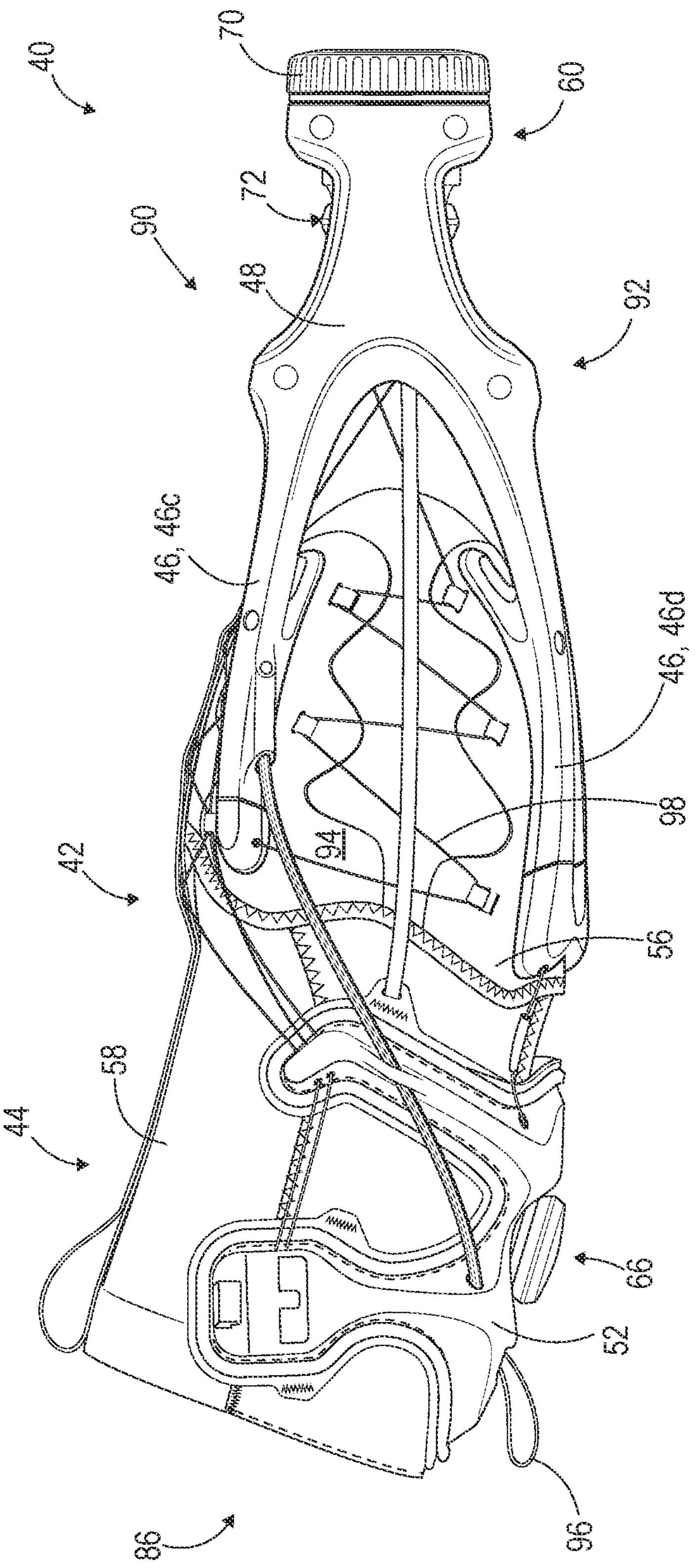
FIG. 6 is a lateral side elevation view of the prosthetic device of FIG. 5.
Figure 7:
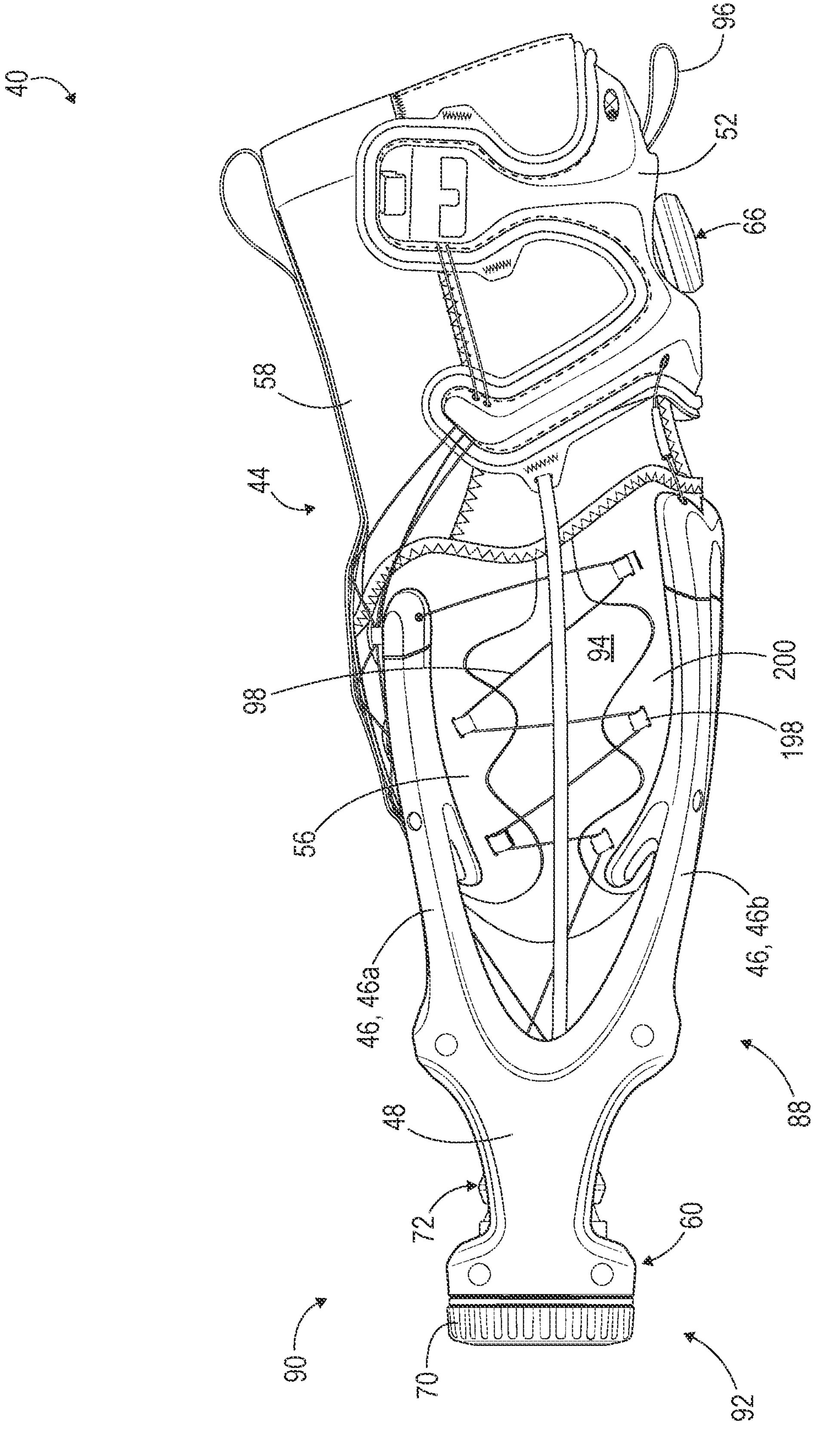
FIG. 7 is a medial side elevation view of the prosthetic device of FIG. 5.

FIGS. 3 and 4 illustrate an example of a range of motion of residual limb 38 that presently disclosed prosthetic devices 40 may be designed to accommodate and preserve. FIG. 3 shows residual limb 38 at full extension, while FIG. 4 shows residual limb 38 at full flexion. In FIG. 3, X represents a distance from cubital fold region 80 to a distal tip 82 of residual limb 38 while in extension, while Y represents a distance from elbow 84 to distal tip 82 of the residual limb while in extension. As residual limb 38 flexes, distance X decreases, while distance Y increases. The increase in distance Y during flexion is represented in FIG. 4 as ΔY, with the skin surface of residual limb 38 stretching as much as 200% in length in the area of elbow 84 during flexion. The decrease in distance X during flexion is represented in FIG. 4 as ΔX, with the skin surface of residual limb 38 overlapping itself in cubital fold region 80 during flexion, thereby creating this reduction in distance X from when residual limb 38 is extended. Encroachment into cubital fold region 80 impacts the ability of residual limb 38 to fold onto itself during flexion, and thus reduces the range of motion of residual limb. As described herein, disclosed prosthetic devices 40 may be configured to reduce or avoid these encroachments to avoid limiting the patient's range of motion.

With reference again to FIG. 2, socket 44 generally may serve as a flexible matrix to which other components of prosthetic device 40 (e.g., elongate counters 46, independent counter 52, and/or selective adjustment system 42) are secured. In disclosed prosthetic devices 40, it is a combination of the fabric matrix nature of socket 44, elongate counters 46, independent counter 52, and selective adjustment system 42 that creates a technical effect of securement and selective tightening around residual limb 38. When a tensile load is borne by distal end region 60 of chassis 48, this load often may start to cause some slippage against residual limb 38 in areas where prosthetic device 40 is less secure. In areas where prosthetic device 40 is more secure, elongate counters 46 will tend to move less and become more firmly seated against residual limb 38. Selective adjustment system 42 may be routed in a manner that encircles residual limb 38, and independent counter 52 may be configured to tighten around residual limb 38 as the more distal components of prosthetic device 40 move away from independent counter 52, thereby tightening components of selective adjustment system 42 around independent counter 52. Unlike conventional rigid sockets, components of socket 44, elongate counters 46 and independent counter 52 can move with respect to each other (even without adjustment of selective adjustment system 42), which creates tightening of prosthetic device 40 around residual limb 38 during some uses. For example, while elongate counters 46 and independent counter 52 have some rigidity to them, they are configured to allow for a certain degree of flex or movement. The fact that independent counter 52 is not completely rigid and can flex inward as selective adjustment system 42 is tightened around it, allows one or more underlying interface pads 64 to be squeezed tighter in circumference around residual limb 38, even as interface pads 64 may also be pulled tighter axially (e.g., along a length of residual limb 38) as a tensile load is applied to distal end region 60 of chassis 48. Components of selective adjustment system 42 distal to independent counter 52 also may include crisscrossing between elongate counters 46, which may similarly tighten circumferentially around residual limb 38 and apply pressure on underlying interface pads 64 to engage residual limb 38. In this manner, socket 44 is tightened as it incrementally lengthens, and the arrangement of selective adjustment system 42 with respect to elongate counters 46 and independent counter 52 causes the pressure of the tightening to be applied in optimized areas of the residual limb to reinforce secure and comfortable engagement of prosthetic device 40 with residual limb 38.

A further advantage of presently disclosed prosthetic devices 40 is that because socket 44 is flexible and secured to elongate counters 46 and independent counter 52 as described herein, as interface pads 64 are tightened into residual limb 38, any tissue displaced by interface pads 64 is free to bulge in areas of socket 44 where stretch is preserved. This configuration has a technical effect of allowing the volume of residual limb 38 to be displaced as opposed to being constricted, helping to preserve the patient's comfort as well as range of motion. In other words, while a "finger trap" style design creates a lattice woven structure that is uniformly tightened when elongated, thereby almost immediately preventing further motion, presently disclosed prosthetic devices 40 enable motion of residual limb 38 even as selective adjustment system 42 is tightened due to the variable compliance of the components of prosthetic device 40 and the way the components are coupled to interact with one another. Overall, the configuration of interface pads 64, combination of stretch and non-stretch elements of socket 44, as well as locations of elongate counters 46 all work together to create as comfortable a position as possible for the anatomy of residual limb 38 to bear loads under pressure in as many loading situations as possible.

While the hard sockets used in prior art prosthetic devices create a single pain point where the distal tip of the residual limb engages with the hard socket, presently disclosed prosthetic devices 40 are designed to avoid this pain point by ensuring that the distal tip of the residual limb comes to rest against a pad and a variably flexible portion of socket 44. For example, flexible portions of socket 44 may conform to the distal tip of residual limb 38, and may combine with interface pads 64 and non-stretch portions of socket 44 to create a pocket for receiving the distal tip of the residual limb. This arrangement in disclosed prosthetic devices 40 distributes pressure more evenly under load, and acknowledges that the bony anatomy of the residual limb moves around inside soft tissue and the whole residual limb invariably moves around in socket 44. By accounting for this with socket 44 being configured to respond to these inevitable movements, a higher level of comfort is possible for the patient than with prior art prosthetic devices.

Socket 44 may be configured to be a padded and/or flexible buffer between the skin surface of residual limb 38 and selective adjustment system 42. Examples of socket 44 include a plurality of layers that integrate with each other and with the plurality of elongate counters 46 to reinforce a connection between residual limb 38 and any end effector 54 coupled to chassis 48. At least part of socket 44 may be formed of a stretch textile, and at least part of socket 44 may be formed of a non-stretch textile. In some examples, socket 44 includes a lower textile socket 56 and an upper textile socket 58. Lower textile socket 56 may be coupled to elongate counters 46, and upper textile socket 58 is coupled to lower textile socket 56. For example, upper textile socket 58 may be at least partially inserted within lower textile socket 56. In some examples, selective adjustment system 42 is configured to provide selective adjustment of compression of lower textile socket 56, independently from upper textile socket 58, around residual limb 38.

Some or all of prosthetic device 40 may be custom-fit for individual patients. For example, elongate counters 46 may be 3D-printed with patient-specific features and/or dimensions. For example, a contact length (i.e., the length of each elongate counter 46 that contacts or interacts with residual limb 38) may be customized for each patient or for the characteristics of their particular residual limb 38. Similarly, the overall length, spacing, and shape of elongate counters 46 may be uniquely designed to receive an individual residual limb 38. For example, at least a proximal portion 62 of elongate counters 46 may be formed to follow a 3D-surface scan or circumference measurements of a particular residual limb 38. For each patient's anatomy, elongate counters 46 may be shaped and sized such that they are configured to avoid impeding a range of movement of residual limb 38, while maintaining sufficient force to counter a load on a terminal device or end effector 54 coupled to chassis 48. In some examples, elongate counters 46 may be formed with an offset that accounts for a thickness of the socket 44. On the other hand, some of prosthetic device 40 may be standardized. For example, distal end region 60 of chassis 48 may be standardized (or available in select standard sizes), while elongate counters 46 may be individualized for each patient. In this manner, elongate counters 46 may be said to bridge between the unique anatomy of the individual patient's residual limb 38 and distal end region 60 of chassis 48. Additionally or alternatively, independent counter 52 may be 3D-printed and/or custom formed so as to be patient-specific. Additionally or alternatively, socket 44 (e.g., upper textile socket 58 and/or lower textile socket 56) may be custom-patterned and fabricated for each respective patient's residual limb 38.

Selective adjustment system 42 works to couple elongate counters 46 and socket 44 together in such a way that prosthetic device 40 is configured to bear a required load exerted on chassis 48 and/or end effector 54 attached thereto, while still preserving the range of motion of residual limb 38. Similarly, other features or components of prosthetic device 40 may be configured and positioned to increase comfort for the patient during such load bearing. For example, prosthetic device 40 may include one or more interface pads 64 associated with socket 44 (e.g., positioned within upper textile socket 58 and/or lower textile socket 56) and/or independent counter 52. Interface pads 64 generally are configured to provide cushioning for one or more bony prominences of residual limb 38 by being positioned between elongate counters 46 (and/or independent counter 52) and the residual limb. In other words, interface pads 64 may be configured to interface with the patient's underlying bone structure and/or bony prominences of residual limb 38.

Any desired motion or reaction to a force requires residual limb 38 to experience two counter-forces, which may be described as static loading. For example, a downward force at distal end region 60 of chassis 48 (e.g., at an end effector attachment unit 70) may create a counter-force upwards on the radius and ulna of the residual limb (or other bones in different levels of amputation), and a counter-force downwards on the elbow. This situation may be referred to as flexion static loading. Interface pads 64 may be configured to be positioned relative to the radius, ulna, and elbow to help cushion the bones of residual limb 38 during these forces, such as by including a respective interface pad 64 on the anterior side of lower textile socket 56 and a respective interface pad 64 on a posterior side of prosthetic device 40 configured to be positioned under the elbow. Similarly, interface pads 64 may be positioned on a posterior side of lower textile socket 56 to cushion the radius and ulna during extension static loading when an upward force may be applied at end effector attachment unit 70. In compression static loading, lower textile socket 56 may aid in cushioning the radius and ulna during the counter-forces applied to the distal tips of those bones. In tension static loading, interface pads 64 may be positioned to cushion the elbow of residual limb 38 from counter-forces applied to the elbow.

As described in further detail herein, one or more interface pads 64 may be laminated within layers of upper textile socket 58 and/or within layers of lower textile socket 56. In some examples, elongate counters 46 are configured to apply compression to one or more such interface pads 64, such that interface pads 64 cushion elongate counters 46. Additionally or alternatively, independent counter 52 may be configured to apply a compressive force on one or more interface pads 64 of prosthetic device 40. Interface pads 64 may be compression molded and/or contoured for optimized fit and/or engagement with residual limb 38. Suitable but non-limiting examples of materials that may be used to form interface pads 64 may include: thermoplastic polyurethane (TPU), ethylene-vinyl acetate (EVA) foam, neoprene, polyester, latex foam, a mineral or silicone gel, wool, cotton, cotton felt, leather, nylon, and/or polylactic acid (PLA). Interface pads 64 may be design to improve comfort for the patient, and thereby improve suspension of residual limb 38 while maintaining a range of motion of residual limb 38. Interface pads 64 may include different layers of varying densities in some examples. For example, some interface pads 64 may contain an area of denser foam or rigid polymer in the center surrounded by softer foam.

Chassis 48 may include an end effector attachment unit 70 configured to receive end effector 54 (e.g., a terminal device, an end effector, a leg end effector, a leg pylon, and/or a prosthetic foot). End effector attachment unit 70 may be positioned within distal end region 60 of chassis 48, such that chassis 48 is configured to operatively and removably couple end effector 54 to residual limb 38. In some examples, end effector attachment unit 70 is selectively adjustable between a lock configuration, a caster configuration, and a release configuration. To transition end effector attachment unit 70 between configurations, end effector attachment unit 70 may be rotated relative to elongate counters 46, though other mechanisms for transitioning between configurations also are within the scope of the present disclosure. In the lock configuration, end effector attachment unit 70 is configured to secure end effector 54 with respect to chassis 48 such that end effector 54 has a fixed position and orientation with respect to chassis 48. In the caster configuration, end effector attachment unit 70 is configured to secure end effector 54 with respect to chassis 48 such that end effector 54 is free to rotate with respect to chassis 48, yet still secured to chassis 48. In the release configuration, end effector attachment unit 70 is configured to release end effector 54 such that end effector 54 may be selectively removed from chassis 48. To change end effectors 54, any presently attached end effector 54 may be removed from end effector attachment unit 70 when the in the release configuration, then a different end effector 54 may be engaged with end effector attachment unit 70, and then end effector attachment unit 70 may be transitioned to the lock configuration or the caster configuration to secure the newly placed end effector 54 with respect to chassis 48 and prosthetic device 40 as a whole. End effector attachment unit 70 may be made from materials configured to provide good grip for ease of transitioning end effector attachment unit 70 between configurations. Additionally or alternatively, end effector attachment unit 70 may include one or more visual indicators to indicate which configuration end effector attachment unit 70 is in at its current position.

Examples of prosthetic devices 40 disclosed herein are primarily illustrated in the example of prosthetic devices for transradial amputations. In these examples, distal end region 60 of chassis 48 is configured as a wrist unit, elongate counters 46 serve as forearm counters that are configured to be positioned surrounding a residual forearm of the patient, and independent counter 52 is an elbow counter configured to be positioned proximal to the patient's elbow when prosthetic device 40 is worn. Generally, elongate counters 46 and independent counter 52 are configured to avoid applying pressure to pressure-intolerant areas of residual limb 38 and areas of the residual limb as needed to preserve a range of motion of the residual limb. For example, for transradial amputations, elongate counters 46 may be configured to terminate distal to a cubital fold region of the patient when prosthetic device 40 is donned. In other words, elongate counters 46 on anterior side 90 of prosthetic device 40 are configured to terminate distal to an area enveloped by elbow flexion of the residual limb.

However, prosthetic devices 40 for other levels of amputation also are within the scope of the present disclosure, and the concepts and features described in the context of transradial amputations may be applied to other levels of amputation, such as transfemoral amputation, transtibial amputation, hip disarticulation, transhumeral amputation, and/or shoulder disarticulation. For example, basic principles described herein may be adapted for other joints or limbs of the body. Generally, disclosed prosthetic devices 40 may be best secured to a residual limb by engaging the next most proximal joint. For example, for a transhumeral prosthesis, prosthetic devices 40 may be adapted to engage the shoulder and/or the opposite shoulder as well. By the same principle as the forearm and elbow, elongate counters 46 at the most distal portion may be configured and arranged to align with the long bone of the residual limb and avoid constraining the parts of the joint that transform the most, away from the neutral axis, allowing motion at the joint to continue. The configurations of selective adjustment system 42 could be applied to other joints and limbs. Independent counter 52 may be configured to engage the clavicle and/or acromion, for example, in the case of a transhumeral amputation. In the case of a transtibial amputation, elongate counters 46 may be configured to avoid the popliteal fossa area behind the knee, rather than the cubital fold region of the elbow. In these examples, the patella of the residual limb would serve a similar anchoring feature as the olecranon, and the femur has similar medial and lateral epicondyles to the elbow, so interface pads 64 may be positioned accordingly. In a transfemoral example, an independent counter 52 may be configured as part of a belt harness and/or with upper textile socket 58 to engage the pelvis. While elongate counters 46 and independent counters 52 are described herein as counteracting forces experienced by prosthetic device 40 when residual limb 38 is an arm, in other examples of prosthetic device 40 (e.g., for transfemoral or transtibial amputations), such elongate counters 46 and independent counters 52 may be configured to counteract forces experienced by prosthetic device 40 when residual limb 38 is a leg, such as during walking. For example, at least one elongate counter may be configured to resist motion relative to the residual limb on heel-strike while walking, and/or at least one elongate counter may be configured to resist motion relative to the residual limb on toe-off while walking.

Disclosed systems 74 for transradial amputation prostheses may include prosthetic device 40 and harness 68. Harness 68 is configured to be worn by the patient while prosthetic device 40 is worn, with harness 68 being coupled to prosthetic device 40 and configured to reinforce securement of prosthetic device 40 to residual limb 38. Systems 74 also may include one or more end effectors 54 for use with prosthetic device 40, which may be selectively coupled to end effector attachment unit 70, as well as selectively removed from end effector attachment unit 70. In some examples, prosthetic device 40 is configured to be selectively coupled to harness 68 via one or more couplers 76 which may be configured to be selectively coupled and de-coupled using one hand. Couplers 76 may be magnetic, though couplers 76 are not limited to the same. Coupler 76 may be fixed to independent counter 52 or to another component or feature of prosthetic device 40. Harness 68 may include at least one portion comprising a stretch fabric or material and at least a second portion comprising a non-stretch material or fabric. In some examples, harness 68 is configured to stretch around a perimeter edge region 78 of the harness, while being substantially static in areas of harness 68 interior to perimeter edge region 78.

Generally, prosthetic devices 40 according to the present disclosure are body-powered and provide on-demand suspension adjustment via a selective adjustment system 42, though features and concepts of disclosed prosthetic devices 40 may be utilized with powered or robotic prosthetic devices. For example, disclosed textile sockets 44, elongate counters 46, and selective adjustment system 42 may be configured for use with powered and myoelectric or nerve-directed wrists and terminal devices. In some examples, mounting for such electronics and a powered wrist may be incorporated in the elongate counters. Additionally or alternatively, socket 44 may include one or more integrated sensors of various types.

As used herein, the term "textile" is non-limiting and is an umbrella term intended to include various fiber-based materials, including fibers, yarns, filaments, threads, and different fabric types (which may be knit, woven, or non-woven, in various examples). The term "textile" may be used interchangeably with the term "fabric" herein. Examples of suitable, but non-limiting, textiles and other materials for components of disclosed prosthetic devices are provided throughout this disclosure, though those of ordinary skill in the art will appreciate that a variety of textiles and/or other materials may be used to accomplish the technical effects described herein. One or more fabrics used to form socket 44 may be breathable to improve moisture management and comfort for the patient while disclosed prosthetic devices 40 are worn. The breathability of a garment or accessory can be calculated using the geometrical dimensions of the component materials and may be imparted with material properties themselves and/or by using perforations in the material. Additionally or alternatively, one or more fabrics used to form socket 44 may be moisture-wicking, such that socket 44 may be configured to wick moisture away from the skin surface of residual limb 38.

While the use of nylon and/or thermoplastic polyurethane to form disclosed elongate counters 46 and independent counters 52 provides advantages described herein, the scope of the present disclosure is not limited to forming these components from nylon and/or thermoplastic polyurethane. Other materials that may be used to form elongate counters 46 and independent counters 52 may include materials such as aluminum, bar stock, 3D-printed metal, polylactic acid (PLA), Acrylonitrile Butadiene Styrene (ABS), high impact polystyrene, polyvinyl alcohol (PVA), carbon fiber, polycarbonate, and/or Acrylic Styrene Acrylonitrile (ASA). Elongate counters 46, chassis 48, independent counter 52, and/or other components of disclosed prosthetic devices 40 may be 3D-printed or may be formed using a variety of other manufacturing techniques, such as by being molded, cut, machined, and/or cast, among others, as will be understood by those of ordinary skill in the art. Likewise, a variety of materials may be suitable for use in selective adjustment system 42 (e.g., for fixed lines and adjustable laces), such as multi-strand wires or cables with flexibility, which may be coated to reduce friction and/or protect from abrasion and/or corrosion. Specific examples include stainless-steel wire rope with coatings of nylon, vinyl, and/or fluorinated ethylene propylene, available from many providers including McMaster-Carr (https://www.mcmaster.com/), though selective adjustment systems 42 are not limited to the same.

Turning now to FIGS. 5-37, illustrative non-exclusive examples of prosthetic devices 40 are illustrated. Where appropriate, the reference numerals from the schematic illustration of FIG. 2 are used to designate corresponding parts in FIGS. 5-37; however, the examples of FIGS. 5-37 are non-exclusive and do not limit prosthetic devices 40 to the illustrated examples of FIGS. 5-37. That is, prosthetic devices 40 are not limited to the specific examples illustrated in FIGS. 5-37 and may incorporate any number of the various aspects, configurations, characteristics, properties, etc. of prosthetic devices 40 that are illustrated in and discussed with reference to the schematic representation of FIG. 2 and/or the examples of FIGS. 5-37, as well as variations thereof, without requiring the inclusion of all such aspects, configurations, characteristics, properties, etc. For the purpose of brevity, each previously discussed component, part, portion, aspect, region, etc. or variants thereof, may not be discussed, illustrated, and/or labeled again with respect to each of FIGS. 5-37; however, it is within the scope of the present disclosure that the previously discussed features, variants, etc. may be utilized therewith.

Figure 8:
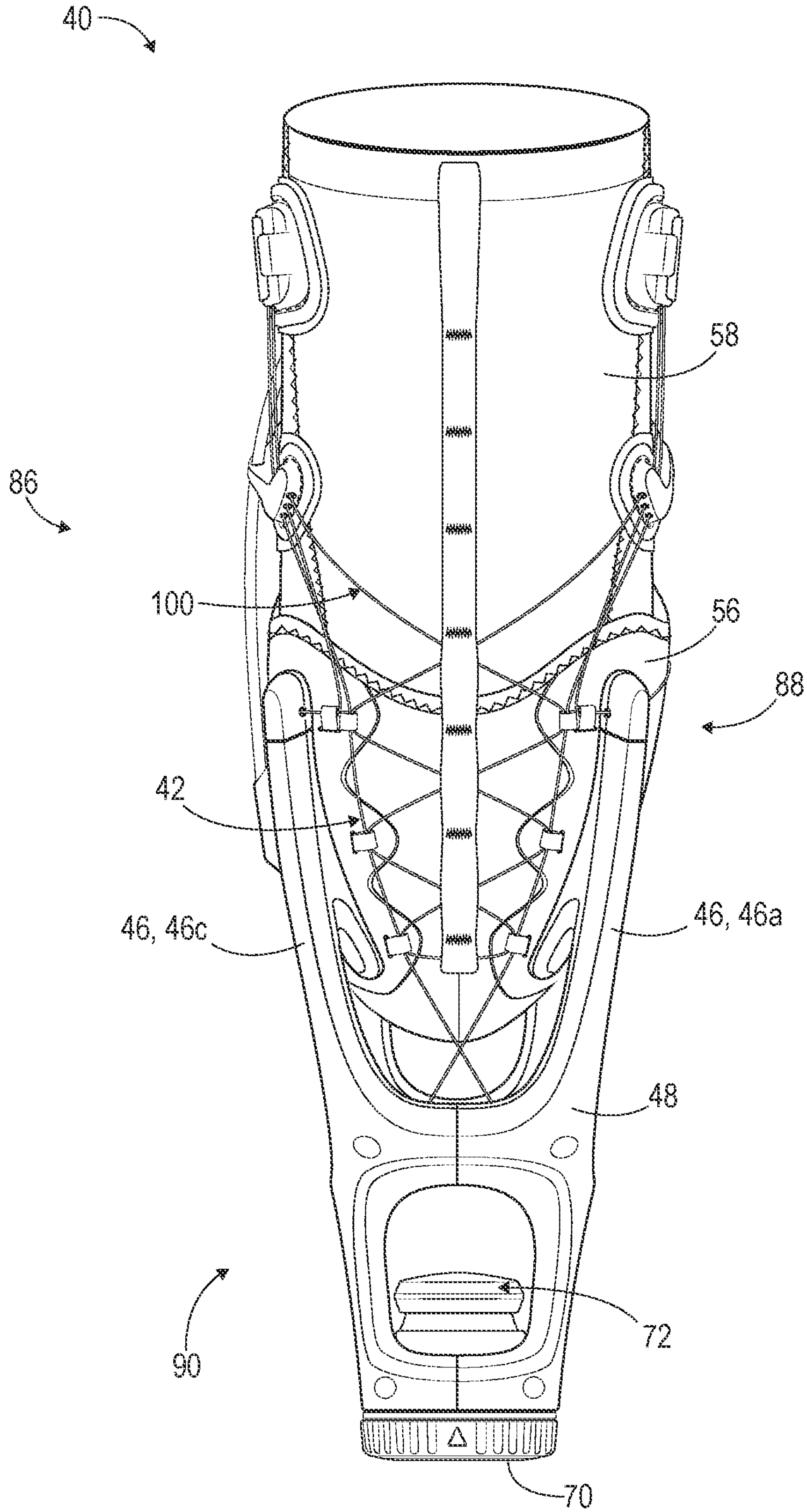
FIG. 8 is a top plan view of the prosthetic device of FIG. 5.
Figure 9:
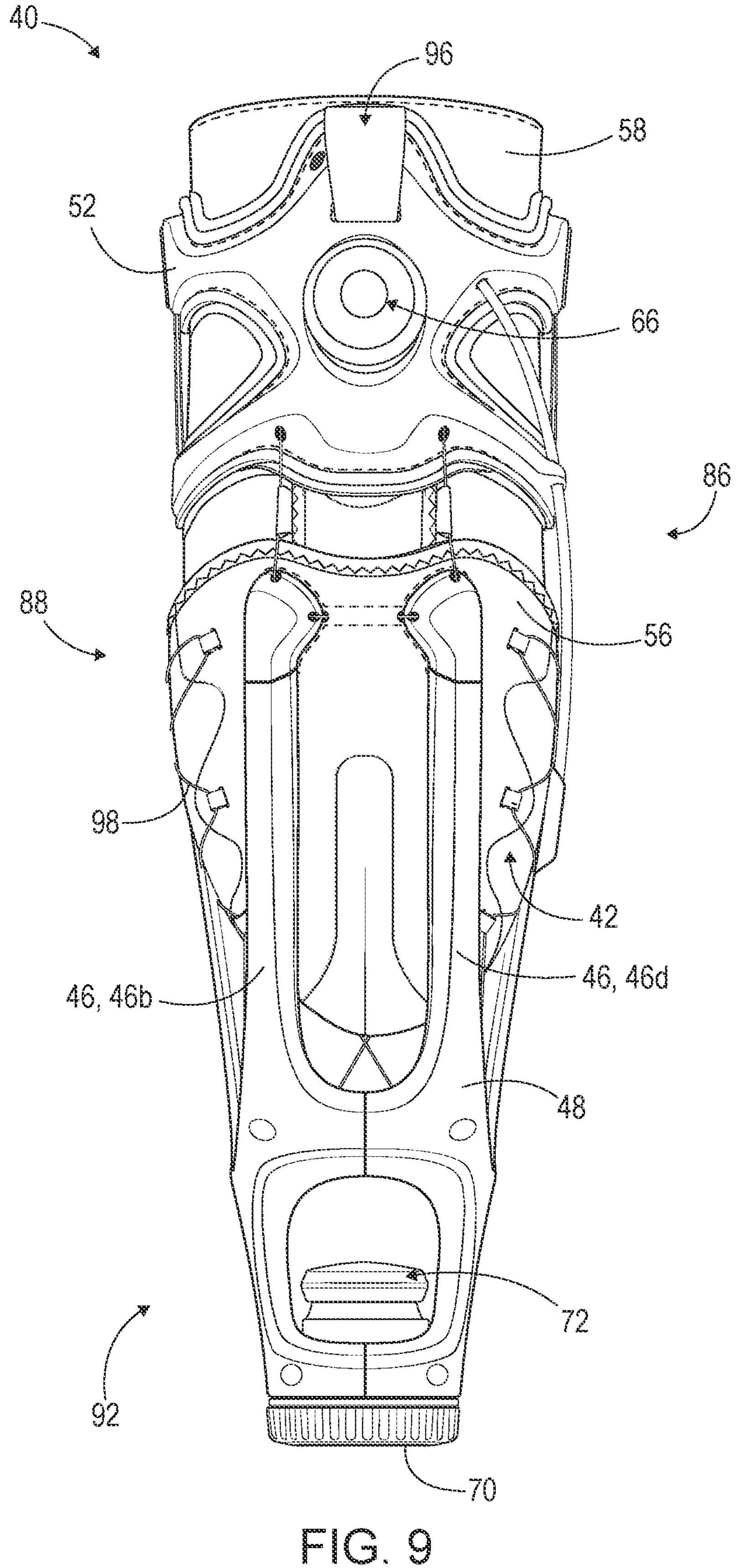
FIG. 9 is a bottom plan view of the prosthetic device of FIG. 5.

FIGS. 5-9 illustrate an example of prosthetic device 40, shown isometrically (FIG. 5), from a lateral side 86 (FIG. 6), from a medial side 88 (FIG. 7), from an anterior side 90 (FIG. 8), and from a posterior side 92 (FIG. 9). In these examples, chassis 48 includes four elongate counters 46, with two elongate counters 46 being positioned on anterior side 90, and two elongate counters 46 being positioned on posterior side 92. Likewise, two of elongate counters 46 are generally positioned medially (i.e., elongate counters **46*a* and 46*b* in FIG. 7), and two of elongate counters 46 are generally positioned laterally (i.e., elongate counters 46*c* and 46*d* in FIG. 6). Elongate counters 46*c* and 46*d* collectively may be referred to as a lateral portion of elongate counters 46, which may be configured to support both an anterior and posterior side of a residual limb (e.g., residual limb 38). Specifically, elongate counter 46*c* may be a lateral anterior elongate counter, and elongate counter 46*d* may be a lateral posterior elongate counter. Similarly, elongate counters 46*a* and 46*b* may collectively be referred to as a medial portion of elongate counters 46, which may be configured to support both an anterior and posterior side of the residual limb. Specifically, elongate counter 46*a* may be a medial anterior elongate counter, and elongate counter 46*b* may be a medial posterior elongate counter. Elongate counters 46 are generally configured to maintain consistent attachment of socket 44 on the residual limb. As best seen in FIGS. 8-9, elongate counters 46 on anterior side 90 of prosthetic device 40 may be arranged differently than elongate counters 46 on posterior side 92 of prosthetic device. For example, elongate counters 46*a* and 46*c* (on anterior side 90, FIG. 8) may be positioned towards medial side 88 and lateral side 86, respectively, extending proximally away from each other at a slight angle. On the other hand, elongate counters 46*b* and 46*d* (on posterior side 92, FIG. 9) may extend proximally at least substantially parallel to one another. In the example of a prosthetic device for transradial amputations, posterior elongate counters 46*b*, 46*d* may be configured to be positioned near to and on either side of the patient's ulna, and may extend proximally to the patient's elbow when prosthetic device 40** is worn.

Socket 44 includes upper textile socket 58 and lower textile socket 56, with elongate counters 46 coupled to lower textile socket 56 (e.g., to an outer surface 94 of lower textile socket 56). Independent counter 52 is directly coupled to upper textile socket 58, and upper textile socket 58 and lower textile socket 56 also are coupled together. Independent counter 52 may include a counter pull loop or tab 96 configured to facilitate positioning of prosthetic device 40 on the residual limb. For example, counter pull loop 96 may be sized to receive the patient's finger, which may be used by inserting the patient's finger through counter pull loop 96 and exerting a force in a proximal direction to help pull socket 44 onto the residual limb. In this example, counter pull loop 96 is configured to be positioned on the posterior side of the residual limb (i.e., pull loop 96 is shown on posterior side 92 of prosthetic device 40, as seen in FIG. 9). In various examples, one or more counter pull loops 96 additionally or alternatively may be positioned in other locations of prosthetic device 40, such as on medial side 88 (e.g., configured to be positioned on the medial side of the residual limb when prosthetic device 40 is worn), on lateral side 86 (e.g., configured to be positioned on the lateral side of the residual limb when prosthetic device 40 is worn), and/or on anterior side 90 (e.g., configured to be positioned on the anterior side of the residual limb when prosthetic device 40 is worn).

Figure 18:
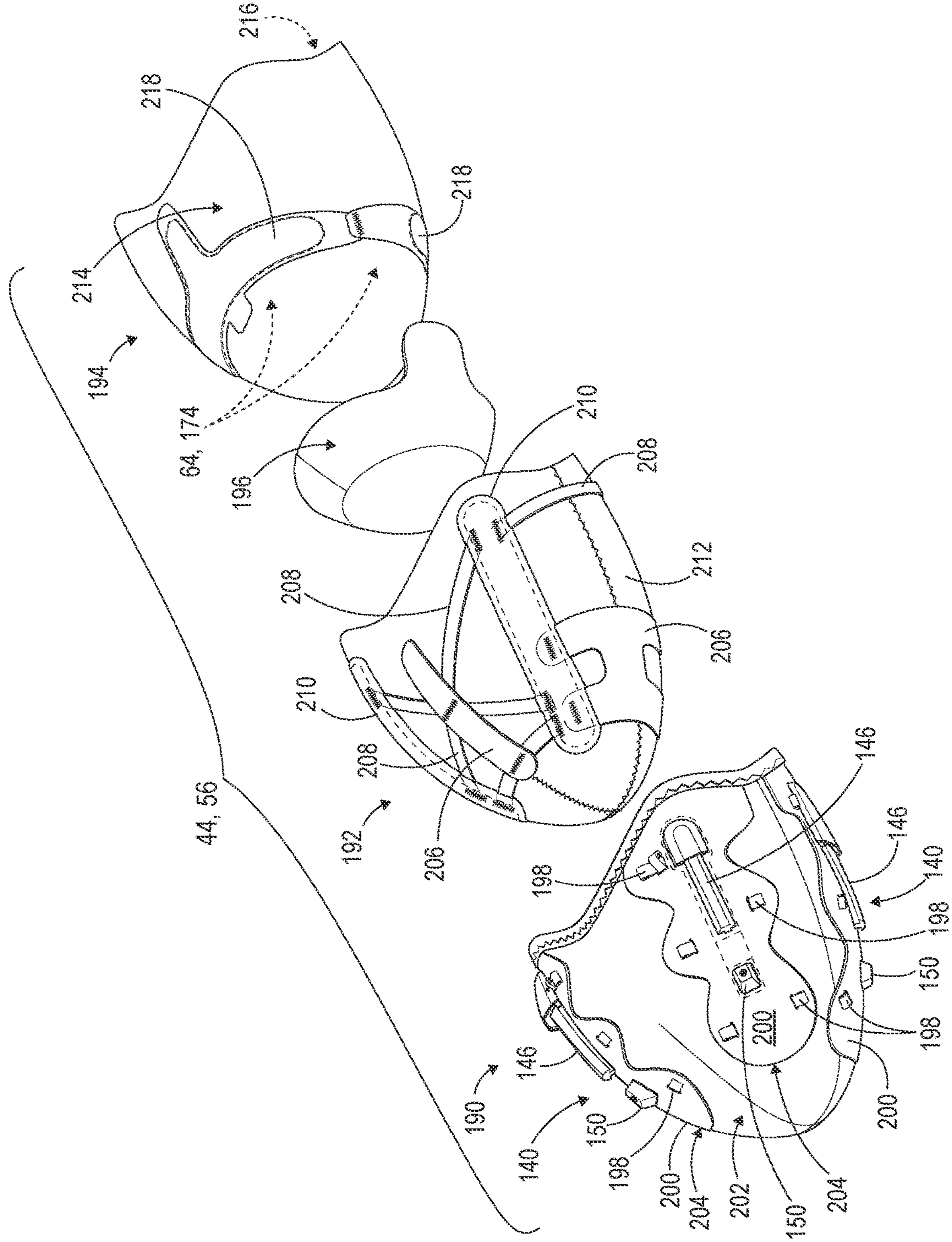
FIG. 18 is an exploded view of an example of a lower textile socket of presently disclosed prosthetic devices.

As best seen in FIGS. 5-9, upper textile socket 58 may be positioned at least partially within lower textile socket 56. For example, upper textile socket 58 may be coupled to an inner socket surface of lower textile socket 56, such as to an inner liner layer 216 (FIG. 18).

Selective adjustment system 42 generally includes lacing and/or a plurality of wires, fibers, laces, lines, and/or cables that pass around, over, and/or across one or more joints of the residual limb. Selective adjustment system 42 may be said to be configured to function as one or more flexible hinges, thereby working with the socket 44 to adjust to range of motion and changes in volume of the residual limb. As shown in the figures and described herein throughout, the wires, fibers, laces, lines, and/or cables of selective adjustment system 42 may be integrated into, mounted on, and/or passed through chassis 48, elongate counters 46, socket 44, and/or independent counter 52. Thus, selective adjustment system 42 may be configured to create a plurality of flexible hinges connecting socket 44 to other components of prosthetic device 40 and/or to harness 68.

Selective adjustment system 42 generally may include one or more fixed lines having a set or predetermined length and one or more adjustable laces configured for selective adjustment in tension and/or length. While the convention used herein describes the fixed aspects of selective adjustment system 42 as fixed "lines," it is to be understood that the fixed lines may be any of wires, fibers, laces, lines, and/or cables, or similar structures. Similarly, the convention used herein describes the adjustable aspects of selective adjustment system 42 as "laces," it is to be understood that such adjustable aspects may be any of wires, fibers, laces, lines, cables, and/or similar structures. Furthermore, while some aspects of selective adjustment system 42 are described as "fixed," it is within the scope of the present disclosure that such fixed lines may, in some examples, be adjustable, though generally the adjustability of the fixed lines is less than that of the adjustable laces, and/or configured to be adjusted less frequently. In other words, while tensioning reels 66, 72 may permit quick and easy adjustment of the tension or length of the adjustable laces of selective adjustment system 42, adjustment of the fixed lines may require tools and/or generally is not adapted for repeated or frequent adjustments.

Selective adjustment system 42 may include a balancing lace 98 and a top lace 100. Balancing lace 98 is sometimes referred to as a hinge lace 98, though the term "balancing lace" is used herein to avoid confusion with hinges discussed herein formed via various components of selective adjustment system 42. Top lace 100 may be configured to automatically increase in tension in response to extension of the residual limb, thereby limiting slip of prosthetic device 40 on the residual limb, and top lace 100 may be further configured to automatically decrease in tension in response to flexion of the residual limb. On the other hand, balancing lace 98 may be configured to automatically increase in tension in response to flexion of the residual limb, thereby limiting slip of prosthetic device 40 on the residual limb, and balancing lace 98 may be further configured to automatically decrease in tension in response to extension of the residual limb.

Independent counter 52 may be sized such that the independent counter applies compression to one or more interface pads 64 when prosthetic device 40 is worn. When the residual limb is flexed, tissues of the residual limb may expand outward (e.g., in the cubital fold region), thereby slightly increasing compression on interface pads 64 by independent counter 52. At the same time, top lace 100 is configured to slacken during flexion of residual limb 38, such that expansion of the cubital fold region (or other area, in the case of prosthetic devices 40 adapted for other levels of amputation) is not restricted. Independent counter 52 also flexes slightly outward to accommodate the expansion of the cubital fold area. On the other hand, when the residual limb is extended, the volume in the cubital fold area decreases and top lace 100 tightens, thereby compressing independent counter 52. In addition to these automatic changes in tension during use, the patient can selectively adjust the tension of top lace 100 (e.g., via proximal tensioning reel 66) and balancing lace 98 (e.g., via distal tensioning reel 72) independently of one another.

Figure 10:
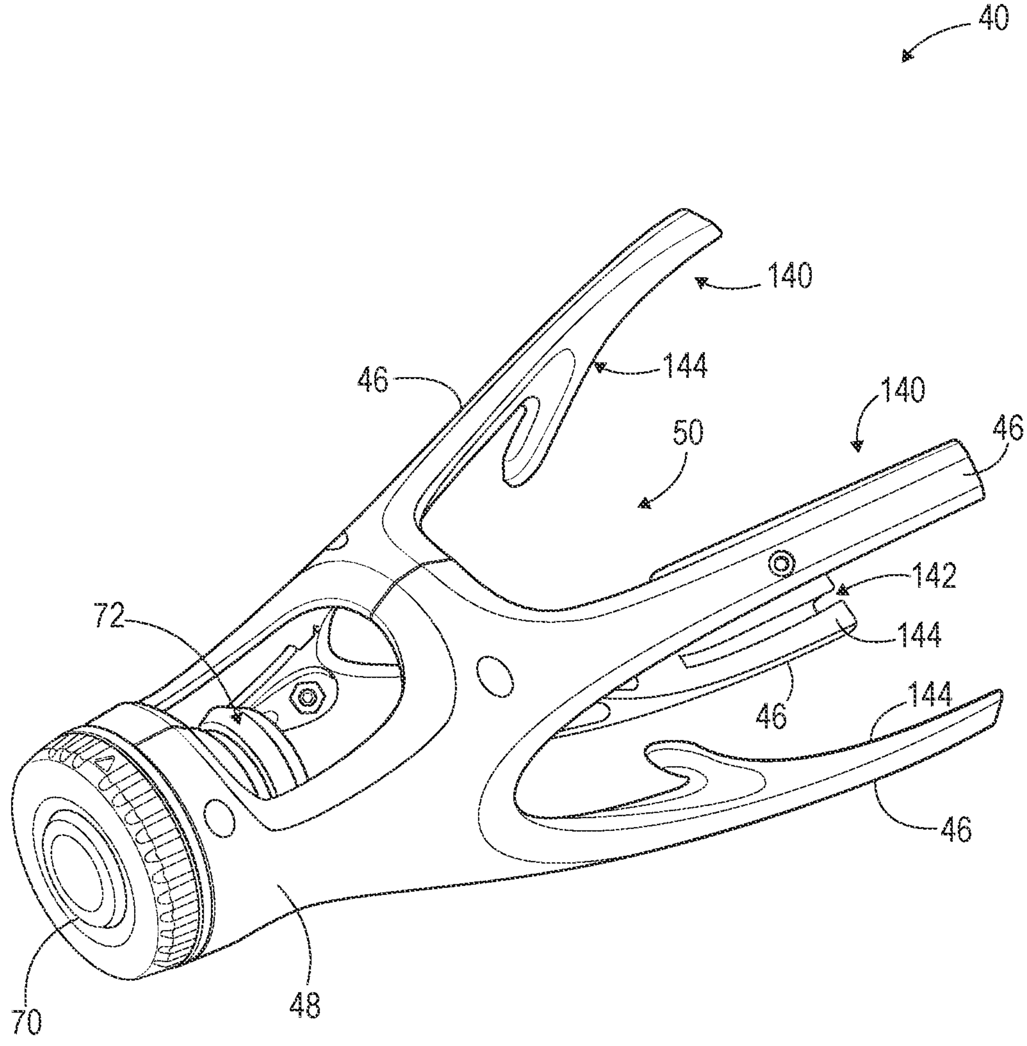
FIG. 10 is a perspective view of an example of a chassis and a plurality of elongate counters.
Figure 11:
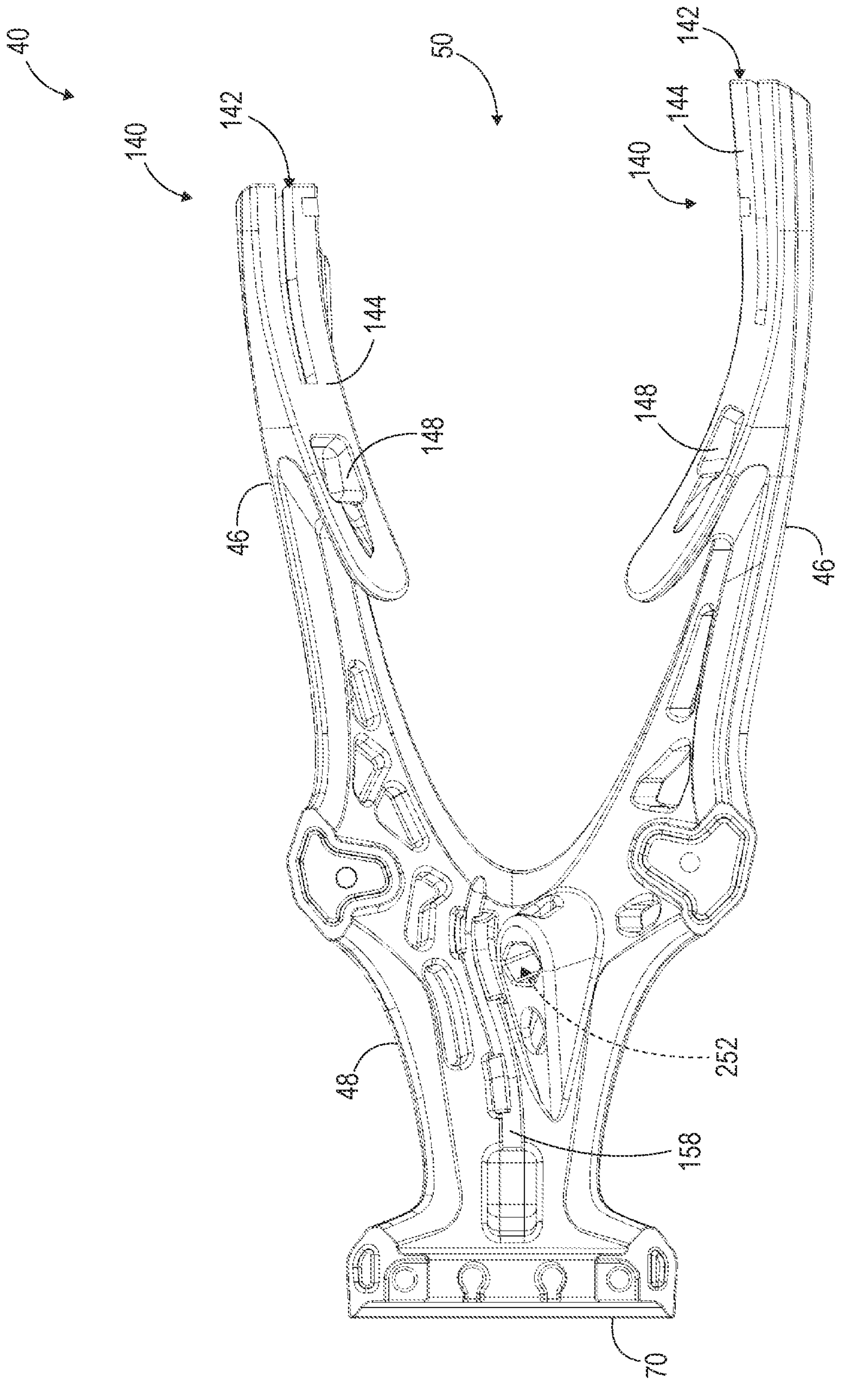
FIG. 11 is a section view of an example of a chassis and a plurality of elongate counters.

FIGS. 10-11 illustrate an example of chassis 48 shown isometrically in isolation (FIG. 10) and in cross section (FIG. 11). Elongate counters 46 may include a keyed-rail system 140 and associated fixing hardware for coupling socket 44 (e.g., lower textile socket 56, an example of which is shown in FIGS. 5-9) to elongate counters 46. In some examples, keyed-rail system 140 serves to couple each individual elongate counter 46 to the lower textile socket 56. Keyed-rail system 140 may be configured to allow elongate counters 46 to be attached securely to socket 44, so that the non-stretch portions of socket 44 form a hammock-like support structure that secures socket 44 to residual limb 38 and resists movement (e.g., slip) of socket 44 with respect to residual limb 38.

Figure 13:
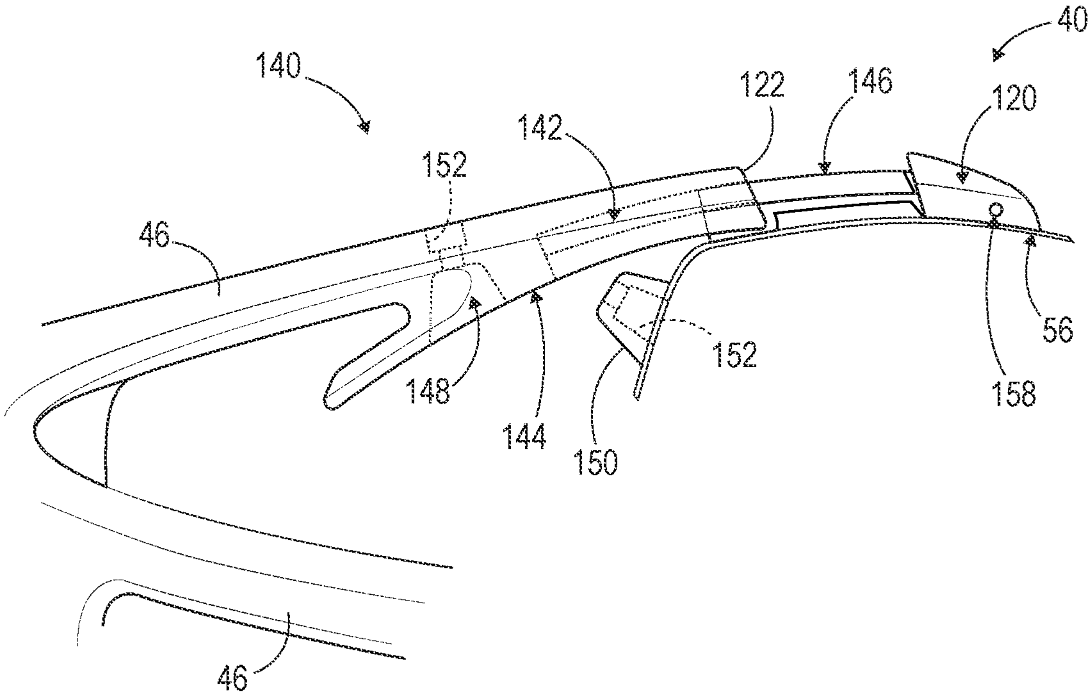
FIG. 13 is a partial side elevation view of an example of a keyed-rail system for use with disclosed prosthetic devices, shown with the rail partially inserted.
Figure 14:
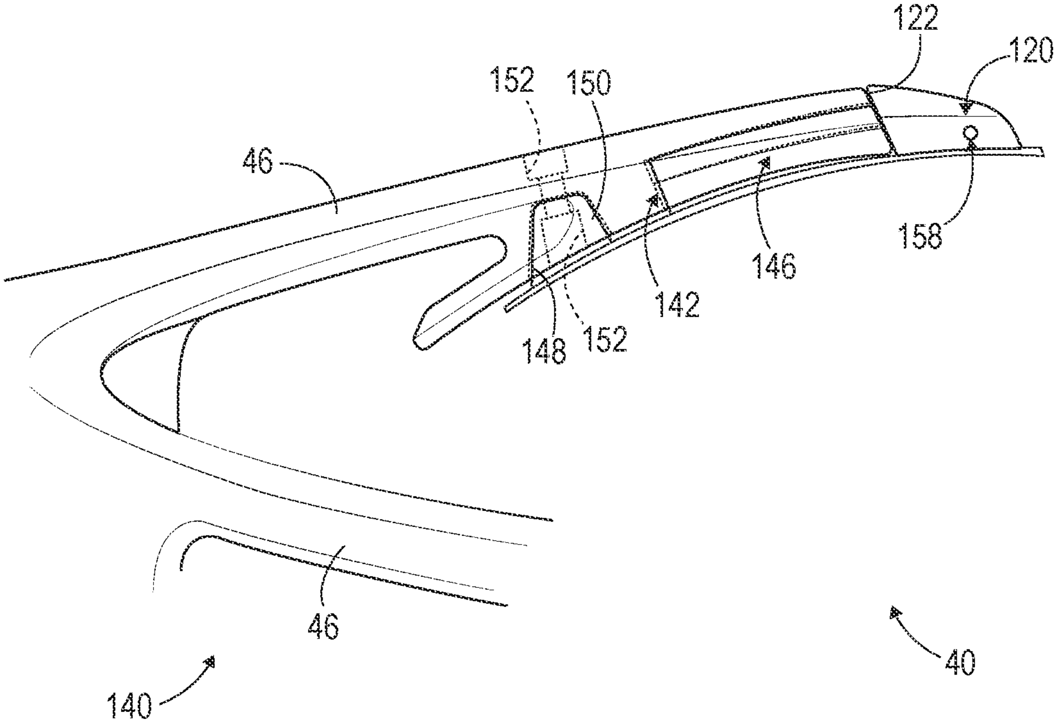
FIG. 14 is a partial side elevation view of the keyed-rail system of FIG. 13, shown with the rail fully inserted.

Keyed-rail system 140 may include a recessed track 142 formed in an inner counter surface 144 of each respective elongate counter 46. Keyed-rail system 140 also may include a plurality of complementary rails 146 protruding from lower textile socket 56, as best seen in FIGS. 13-14. Each respective rail 146 is configured to slide into a respective recessed track 142 of a respective elongate counter 46. FIGS. 13-14 illustrate a close-up of a portion of keyed-rail system 140, showing rail 146 partially (FIG. 13) and fully (FIG. 14) inserted into recessed track 142. As best seen in FIGS. 11 and 13-14, keyed-rail system 140 may include a plurality of cavities 148, with each respective cavity 148 being formed in a respective elongate counter 46. Keyed-rail system 140 also includes a plurality of projections 150, with each respective projection 150 extending from the lower textile socket distal to a respective rail 146. Each respective projection 150 is configured to be at least partially inserted within a respective cavity 148 when the elongate counters 46 are coupled to the lower textile socket, as shown in FIG. 14. Keyed-rail system 140 also may include a respective proximal cap 120 positioned at an end of rail 146, opposite projection 150, with proximal cap 120 being enlarged with respect to rail 146. Each proximal cap 120 may engage with (e.g., be in direct contact with) a respective proximal end 122 of a respective elongate counter 46 when the respective rail 146 is fully inserted into the respective recessed track 142 of the respective elongate counter 46. In this manner, each proximal cap 120 may effectively serve as a stop to prevent further translation of each respective rail 146 into a respective recessed track 142 of each elongate counter 46, as proximal cap 120 is sized to preclude insertion into recessed tracks 142.

Keyed-rail system 140 also may include a respective threaded bore 152 extending through each respective cavity 148 and each respective projection 150, such that keyed-rail system 140 may be configured to receive a respective fastener through each respective cavity-projection pair 148, 150 to further secure each elongate counter 46 to the lower textile socket. Rails 146 and projections 150 may be formed of a material with enough strength and rigidity sufficient such that keyed-rail system 140 is configured to secure elongate counters 46 to keyed-rail system 140, and thereby to lower textile socket 56. Keyed-rail system 140 is configured to allow for replacement, cleaning, and interchangeability of components. For example, lower textile socket 56 may be removed from elongate counters 46 by disengaging projections 150 from cavities 148 of elongate counters 46, and sliding rails 146 out from the recessed tracks 142 of elongate counters 46. Lower textile socket 56 may then be cleaned and re-coupled to elongate counters 46, and/or replaced with a different textile socket or other component, as desired. The sizes of recessed tracks 142, rails 146, cavities 148, and/or projections 150 may be varied depending on the size of prosthetic device 40, as determined by the size and unique anatomy of each particular residual limb.

Figure 19:
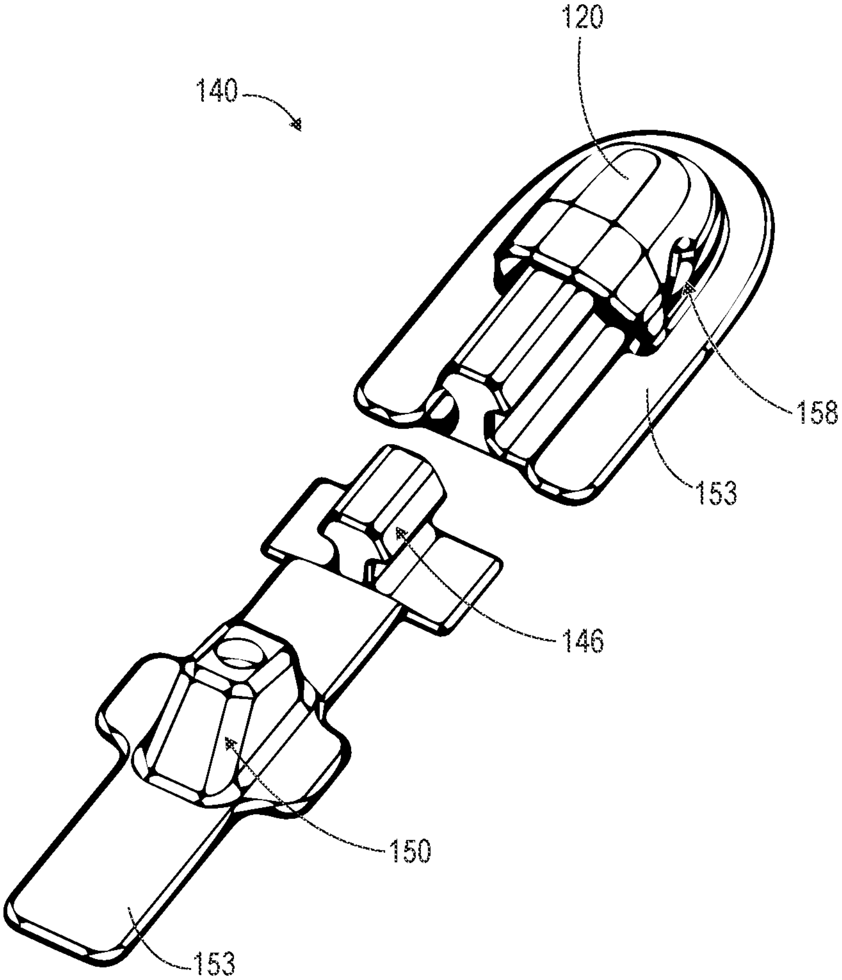
FIG. 19 is a perspective view of components of an example of keyed-rail system of presently disclosed prosthetic devices.

FIG. 19 illustrates an example of the portion of keyed-rail system 140 coupled to lower textile socket 56, shown in isolation for clarity. As best seen in FIG. 19, keyed-rail system 140 may include one or more sew tabs 153 configured to aid in integrating rails 146 and projections 150 into socket 44. For example, sew tabs 153 may be thin plastic (or other material) components extending around the perimeter of rails 146, and proximal and distal to projections 150, that can be sewn through to integrate keyed-rail system 140 with socket 44. Sew tabs 153 may be overlayed with sturdier non-stretch materials or fabrics to reinforce attachment of keyed-rail system 140 to socket 44, and/or to create a smooth transition from stiffer components to more flexible components, thereby creating a gradual transition from stretch and cushion (e.g., interface pads 64 and socket 44) to more rigid support (e.g., elongate counters 46).

Figure 12:
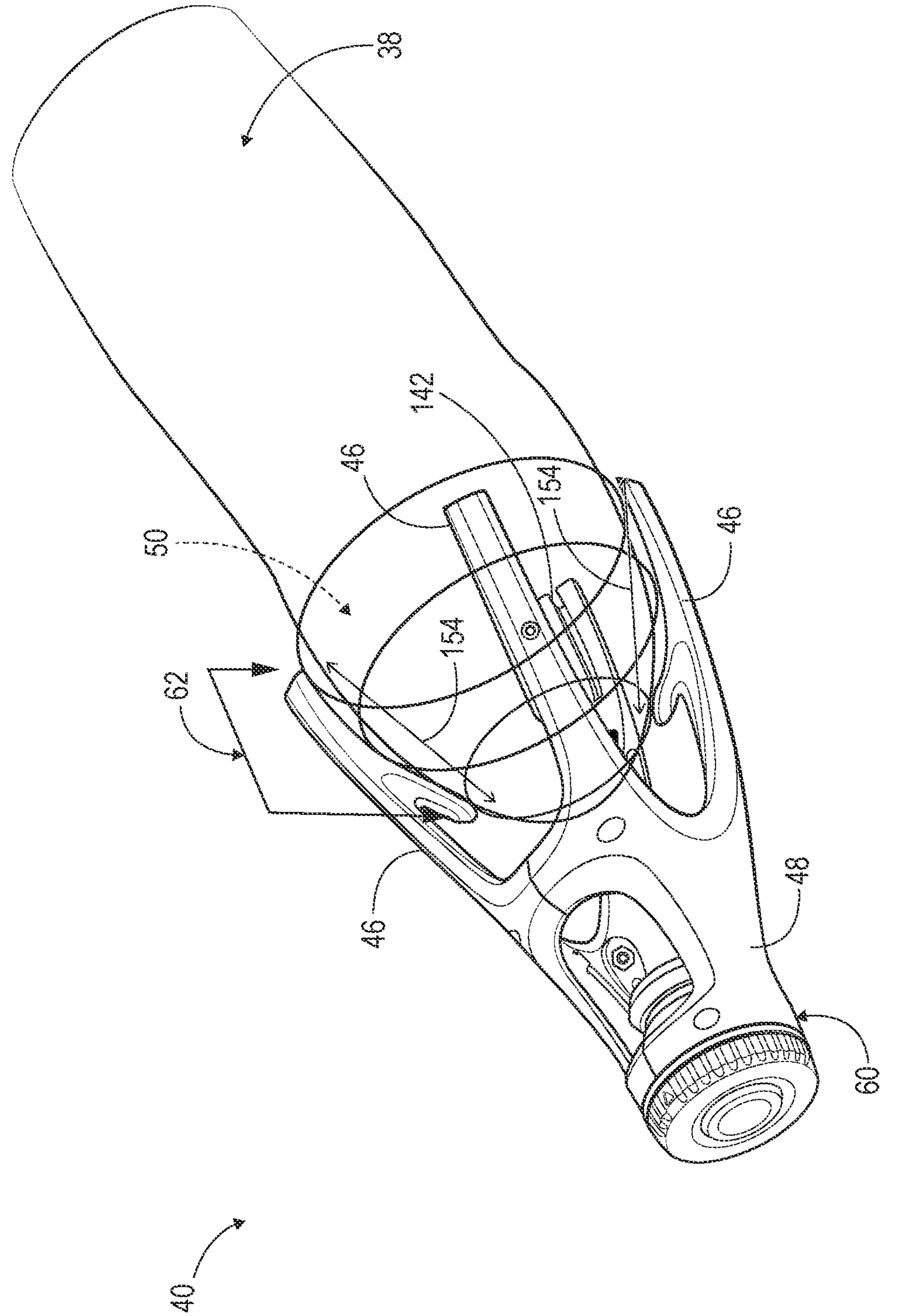
FIG. 12 is a perspective view of an example of a chassis and a plurality of elongate counters, shown with a schematic representation of a residual limb.

FIG. 12 shows chassis 48 in isolation, with an approximation of residual limb 38 (represented by a series of ellipses) positioned within volume 50 defined between elongate counters 46. Proximal portion 62 of elongate counters 46 may be formed to follow a 3D-surface scan of residual limb 38, with an offset to account for the thickness of socket 44, or may be approximated with a series of measured circumferences. A contact length 154 representing the portion of elongate counter 46 engaged with residual limb 38 may be patient-specific, and may vary with each respective elongate counter 46, depending on the anatomy of the specific residual limb 38.

Figure 15:
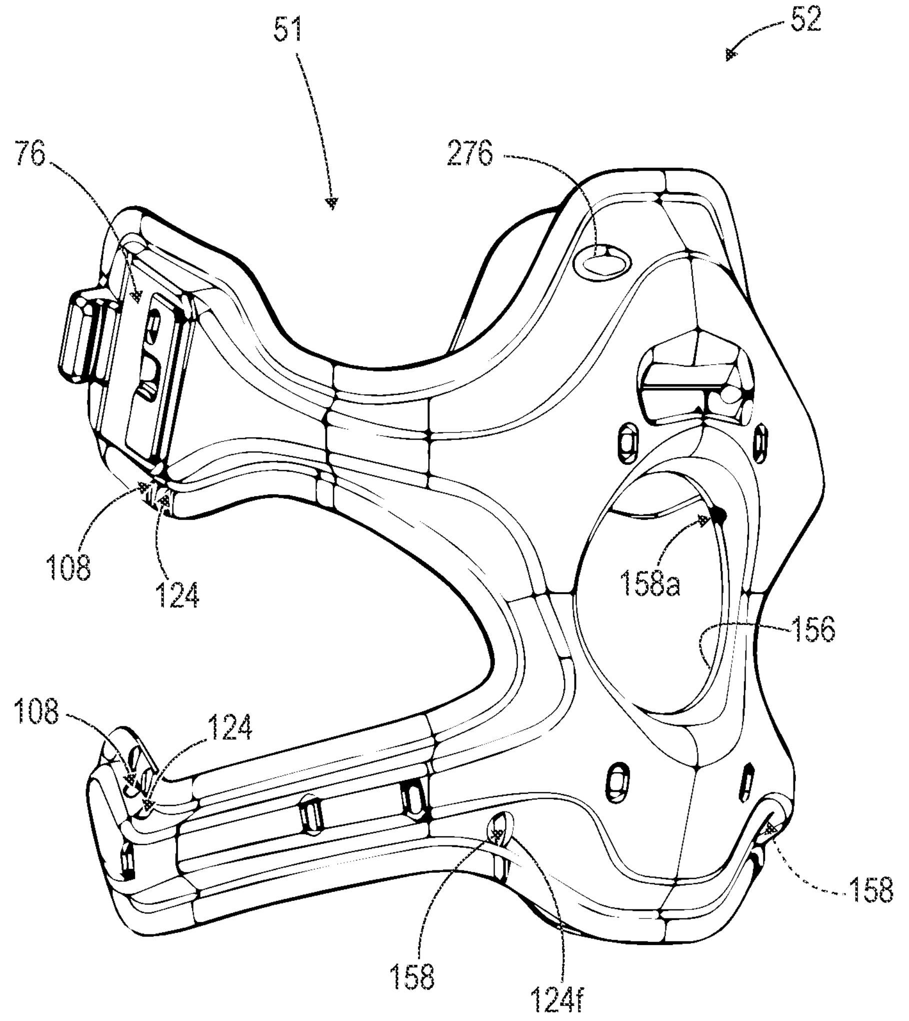
FIG. 15 is a perspective view of an example of an independent counter.

FIG. 15 illustrates an example of independent counter 52 in isolation from the rest of prosthetic device 40. In the example of FIG. 15, independent counter 52 is illustrated as an elbow counter configured to engage the patient's residual limb proximal to the patient's elbow, though independent counters 52 may be designed for other areas of the body and/or other levels of amputation. In the example of independent counter 52 being an elbow counter, independent counter 52 may be configured to be positioned posterior to an ulna of the patient when prosthetic device 40 is worn. Independent counter 52 may be configured to apply flexible inward pressure on one or more interface pads (e.g., supracondylar counter interface pads), and may be directly coupled (e.g., sewn) to socket 44 (e.g., upper textile socket 58). Independent counter 52 may house proximal tensioning reel 66, which may be seated within or through a recessed aperture 156 formed through independent counter 52. The surrounding area of such recessed aperture 156 also may be configured to ensure access to proximal tensioning reel 66, while at the same time guarding against unintentional adjustment of proximal tensioning reel 66. Independent counter 52 of FIG. 15 also includes coupler 76, which may be a magnetic attachment point configured for selective coupling to a harness worn by the patient.

Independent counter 52 may include one or more internal lace guides 158 that extend through a thickness of independent counter 52. For example, internal lace guides 158 may be a bore formed through independent counter, with entry and exit points on independent counter 52 through which one or more cables, wires, lines, etc. of selective adjustment system 42 may be passed. Passing components of selective adjustment system 42 through internal lace guides 158 may serve to help couple selective adjustment system 42 to independent counter 52, to secure the position of the respective components of selective adjustment system 42 with respect to independent counter 52, and/or to protect the components of selective adjustment system 42 from damage or wear by shielding the components of the selective adjustment system from the environment.

Figure 16:
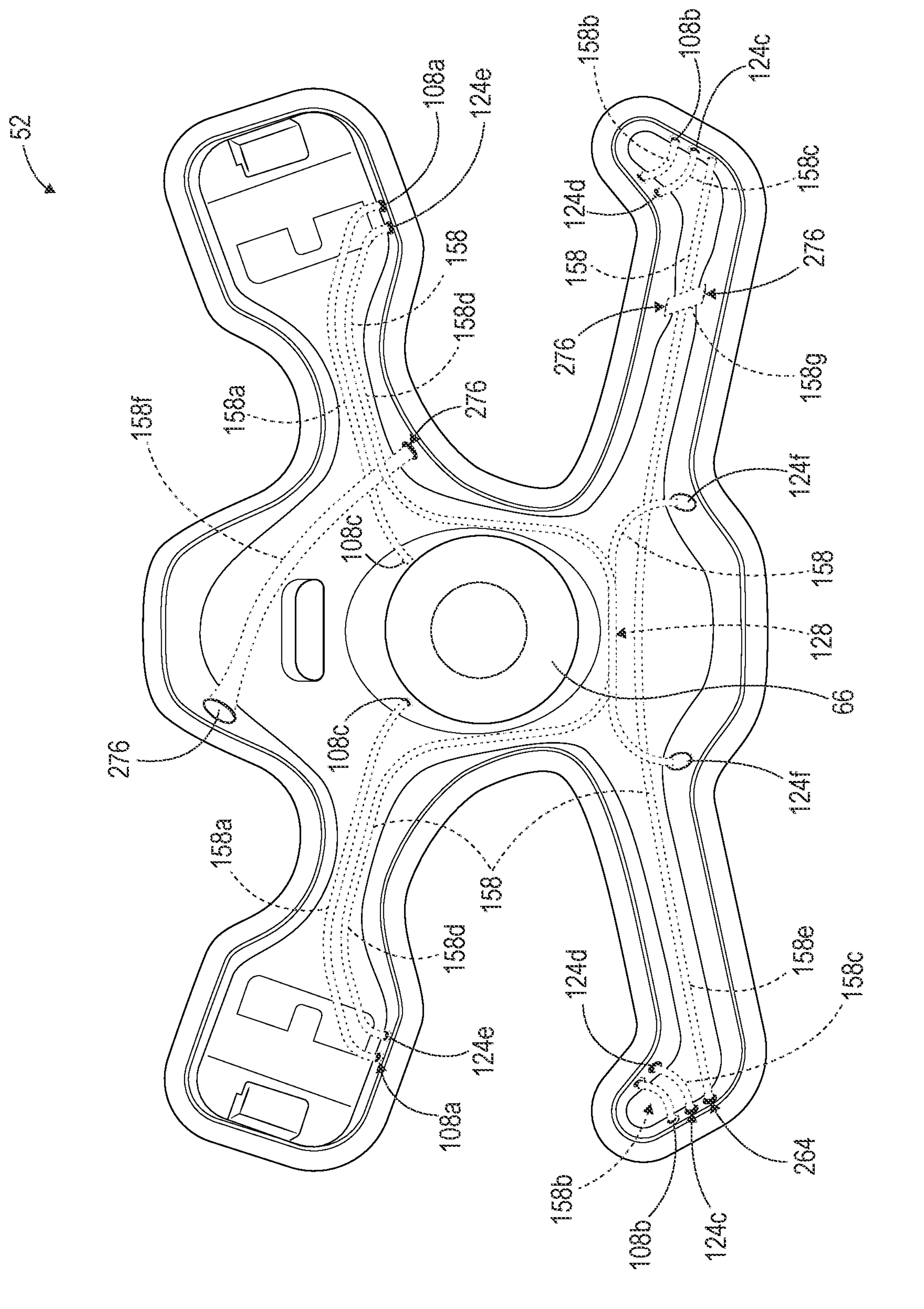
FIG. 16 is a flattened top plan view of an example of an independent counter.

FIG. 16 shows a flattened view of an example of independent counter 52, with internal lace guides 158 shown extending through independent counter 52 in dashed lines. Internal lace guides 158 may serve to route balancing lace 98 through a plurality of crossings of balancing lace 98 in the patient's elbow area. Additionally or alternatively, internal lace guides 158 of independent counter 52 may be configured to route top lace 100 from proximal tensioning reel 66 to one or more crossings of top lace 100 in the patient's elbow area. In some examples, internal lace guides 158 of independent counter 52 route top lace 100 from proximal tensioning reel 66 over a guide, located on one or more interface pads 64, and then to elongate counters 46. Such routing may be configured to ensure that top lace 100 pulls on the guide to tighten interface pads 64 around the residual limb when chassis 48 is load-bearing. Interface pads 64 may be configured to be positioned to exert pressure on the patient's epicondyles, thereby helping to secure socket 44 onto the residual limb. As shown in FIG. 16, independent counter 52 also may include internal guides **158*f* and 158*g* for receiving the housing for an actuation cable (also referred to as a control cable) to open or close a body-powered terminal device. Such actuation cables may be coupled to harness 68 at one end, and to the terminal device or other end effector at the other end, passing through at least independent counter 52**. Actuation cables are understood in the art and not described in detail herein. The actuation cable housing, internal guides, and integrated stops may be provided in lieu of the Bowden cable of a traditional body-powered device, and the cable hangers that secure its two ends.

Figure 17:
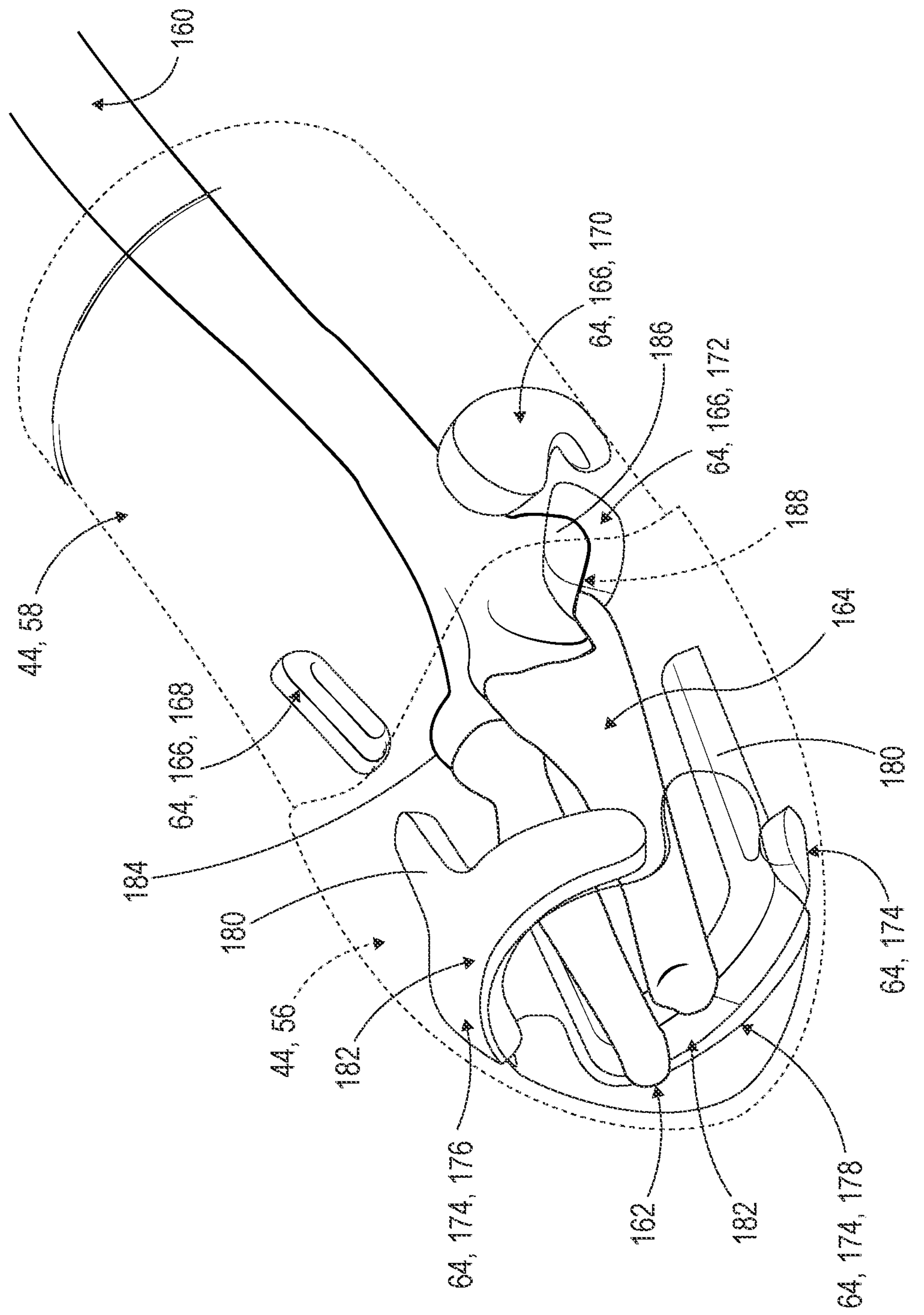
FIG. 17 is a perspective schematic view of a socket of presently disclosed prosthetic devices, illustrating an example of placement of interface pads relative to bones of the residual limb.

FIG. 17 shows an example of a collection of interface pads 64 that may be incorporated into disclosed prosthetic devices 40. In FIG. 17, interface pads 64 are illustrated in the context of each interface pads' position relative to socket 44, which is shown in dashed line. The patient's humerus 160, radius 162, and ulna 164 also are illustrated for the context of demonstrating areas of the residual limb that interface pads 64 may be configured to engage with, or be positioned over or under. While interface pads 64 illustrated in FIG. 17 have been found to be advantageous in prosthetic devices 40 developed for transradial amputations, other examples of prosthetic devices 40 according to the present disclosure may include fewer interface pads 64, more interface pads 64, differently positioned interface pads 64, and/or differently shaped or oriented interface pads 64. Placement, form, density and scale of interface pads 64 may be individually determined for each unique individual residual limb to ensure a secure and comfortable fit with prosthetic device 40, while preserving the patient's range of motion.

In the example of FIG. 17, upper textile socket 58 includes one or more interface pads 64 that may be configured as elbow interface pads 166 (i.e., elbow interface pads 166 are an example of interface pads 64). Such elbow interface pads 166 may be configured to be positioned to engage with and cushion humerus 160 of the residual limb. In a specific example, elbow interface pads 166 include a lateral elbow pad 168 configured to be positioned on a lateral side of the patient's elbow (e.g., to rest on or against lateral epicondyle 184 of the residual limb), a medial elbow pad 170 configured to be positioned on a medial side of the patient's elbow (e.g., to rest on or against medial epicondyle 186 of the residual limb), and a posterior elbow pad 172 configured to be positioned on a posterior side of the patient's elbow (e.g., to rest on or against olecranon fossa 188 of the residual limb), as illustrated in FIG. 17. Elbow interface pads 166 may be configured to interface with the bony prominences (e.g., epicondyles 184, 186) of the patient's elbow, through the tissues of the residual limb. Independent counter 52 may be sized, shaped, and positioned relative to elbow interface pads 166 to apply a variable amount of pressure on elbow interface pads 166 to help keep the interface pads in a desired position relative to the patient's humerus 160.

Additionally or alternatively, lower textile socket 56 may include one or more interface pads 64 that are configured as forearm interface pads 174 (e.g., forearm interface pads 174 are an example of interface pads 64). Such forearm interface pads 174 may be configured to be positioned to support the forearm of the residual limb (e.g., radius 162 and ulna 164). In a specific example, forearm interface pads 174 may include an anterior forearm pad 176 configured to be positioned on an anterior side of the residual limb, and a posterior forearm pad 178 configured to be positioned on a posterior side of the residual limb. As shown in FIG. 17, forearm interface pads 174 each may include one or more elongate portions 180, which may be configured to be positioned to extend substantially parallel to radius 162 and ulna 164. These elongate portions 180 may be configured to function to help center prosthetic device 40 relative to a central longitudinal axis of the residual limb. Additionally or alternatively, forearm interface pads 174 each may include a curved portion 182 configured to be positioned such that the respective curved portion 182 extends substantially perpendicularly to radius 162 and ulna 164 of the residual limb. Curved portions 182 may be positioned distally to elongate portions 180, with elongate portions 180 extending proximally away from curved portions 182. Forearm interface pads 174 may be configured to restrict ends of radius 162 and ulna 164 of the residual limb when chassis 48 is under different loads, via the curved portion 182 of each forearm interface pad 174. To adapt interface pads 64 for use in other levels of amputation, interface pads 64 may be positioned and configured to engage other bony prominences of other residual limbs, such as to provide cushioning and engage with the patella and the distal tips of the tibia and fibula to support weight bearing in amputations of the leg (e.g., transtibial amputations).

FIG. 18 illustrates an exploded view of an example of lower textile socket 56 of socket 44. As shown in FIG. 18, lower textile socket 56 may include a plurality of layers, such as an outer layer 190, a middle layer 192, an inner liner 194, and/or a padded distal cup 196. If made of a stiffer material, such as for a weight-bearing transtibial prosthesis, distal cup 196 also may be supported by a similarly shaped distal tip counter, which may be a distal independent counter, or a distal counter neither elongate nor directly connected to the chassis of the prosthesis. Overall, lower textile socket 56 may be custom-patterned and fabricated for each individual patient. Lower textile socket 56 is configured to allow for some stretch, while the combination of layers 190, 192, 194, 196 are configured to provide structure and padding to support the residual limb. In some examples, layers 190, 192, 194, 196 may be individually formed, and then joined or coupled together to form lower textile socket 56.

In some examples, lower textile socket 56 (and/or upper textile socket 58) may be an engineered knit textile socket that may incorporate one or more stretch features of socket 44 as well as one or more non-stretch features (such as those of middle layer 192) in a single layer, with these different functional features achieved by the use of different fibers and stitches to achieve the same properties as the assembled textile sockets 44 described herein. Engineered knit shoe uppers used in athletic shoes have managed to incorporate many features of modern athletic footwear design that previously required separate hands on manufacturing steps and individually placed components. For example, eyelets and lace guides, channels for laces and structural members, stretch and non-stretch regions of the shoe upper, and features for easing assembly of the finished shoe have been incorporated in engineered knit shoe upper. Similar concepts may be utilized with disclosed prosthetic devices 40, such as to upper textile socket 58, lower textile socket 56, and/or other components of prosthetic device 40. Such examples may, in the same way that shoe uppers have been engineered, be constructed of engineered knit textiles that incorporate all of the features included in every layer of the upper or lower textile sockets 58, 56 and related components, including but not limited to the eyelets, lace guides, channels for lace components, pockets and containers for padding and counters or stiffeners, reinforcements, and any other components of the multiple separate layers or additions to the upper and lower textile sockets. In this way, in the same way that manufacturing steps and waste have been reduced or eliminated in shoe manufacturing through the use of engineered knitting in either flat or circular fashion, many separate components of upper and/or lower textile sockets 58, 56 can be directly manufactured into a single piece. This piece can either be directly circular knit in three dimensions, or flat knit with individual three dimensional extensions, and later sewn or laminated to create a three dimensional component.

Figure 20:
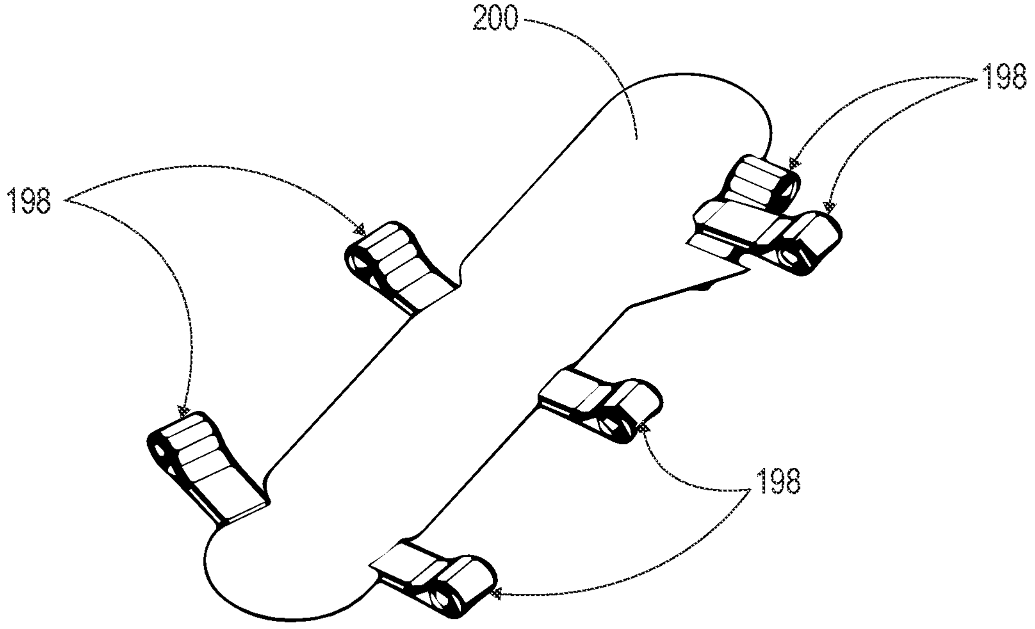
FIG. 20 is a perspective view of an example of lace guides that may be integrated into textile sockets of presently disclosed prosthetic devices.

Outer layer 190 may include a plurality of lace guides 198, or eyelets, for receiving one or more laces, wires, cables, fibers, or lines of selective adjustment system 42. Outer layer 190 may include one or more reinforcing overlays 200, which may include lace guides 198. For example, outer layer 190 in FIG. 18 includes three reinforcing overlays 200, each with a plurality of lace guides 198 for receiving components of selective adjustment system 42. FIG. 20 illustrates an example of reinforcing overlay 200 with a plurality of lace guides 198, shown in isolation for clarity. With continued reference to FIG. 18, reinforcing overlays 200 also may include components of keyed-rail system 140, such as rails 146 and projections 150, discussed in-detail above, in connection with FIGS. 10-14. Overall, outer layer 190 may be formed from abrasion-resistant yet flexible textiles, and may include stretch knit or woven fabrics and/or non-stretch fabrics. For example, a first portion 202 of outer layer 190 may be formed from a stretch textile, while a second portion 204 of outer layer 190 may be formed of a non-stretch textile. In some examples, second portion 204 may coincide with reinforcing overlays 200 (e.g., reinforcing overlays may be formed of non-stretch or low-stretch textiles, such as microsuede). Reinforcing overlays 200 may be bonded and/or sewn to stretch portion 202 to form outer layer 190.

Middle layer 192 may be configured to constrain socket 44 by limiting the extent to which other portions of socket 44 may stretch in a particular direction, under particular loading situations. Middle layer 192 may include a plurality of spaced-apart reinforcement strips 206 configured to reinforce lower textile socket 56. In a non-exclusive example, reinforcement strips 206 may be formed of nylon, though many other materials may be suitable. Middle layer 192 also may include a plurality of elastic straps 208 positioned and configured to provide localized areas of extra stretch, extra compression, and/or resistance to sag in lower textile socket 56, while other areas of middle layer 192 may be lower stretch or non-stretch. For example, elastic straps 208 may be formed of BioThane® or any suitable material, such as a coated polyester webbing. Middle layer 192 of lower textile socket 56 also may include one or more non-woven overlays 210 positioned to at least partially overlay (e.g., overlap) one or more reinforcement strips 206 and/or one or more elastic straps 208. Such non-woven overlays 210 may serve to reinforce reinforcement strips 206 and/or elastic straps 208, and/or reinforce stitching or bonding used to couple reinforcement strips 206 and/or elastic straps 208 to a main body 212 of middle layer 192. Main body 212 may be, for example, a 4D-stretch spacer mesh fabric. In some examples, elongate counters 46 may be coupled to middle layer 192 of lower textile socket 56.

Inner liner 194 of lower textile socket 56 may include a first liner layer 214 and a second liner layer 216 that are laminated and/or stitched together. In some examples, one or more interface pads 64 (e.g. forearm interface pads 174) may be laminated between the first and second liner layers 214, 216. Inner liner 194 also may include a reinforcement overlay 218 in areas where interface pads are located. Padded distal cup 196 may be positioned between middle layer 192 and inner liner 194 for additional padding and/or suspension. Padded distal cup 196 may be configured to function like a hammock, and provides cushioning while at the same time avoiding excess pressure on the distal tip of residual limb 38.

Figure 21:
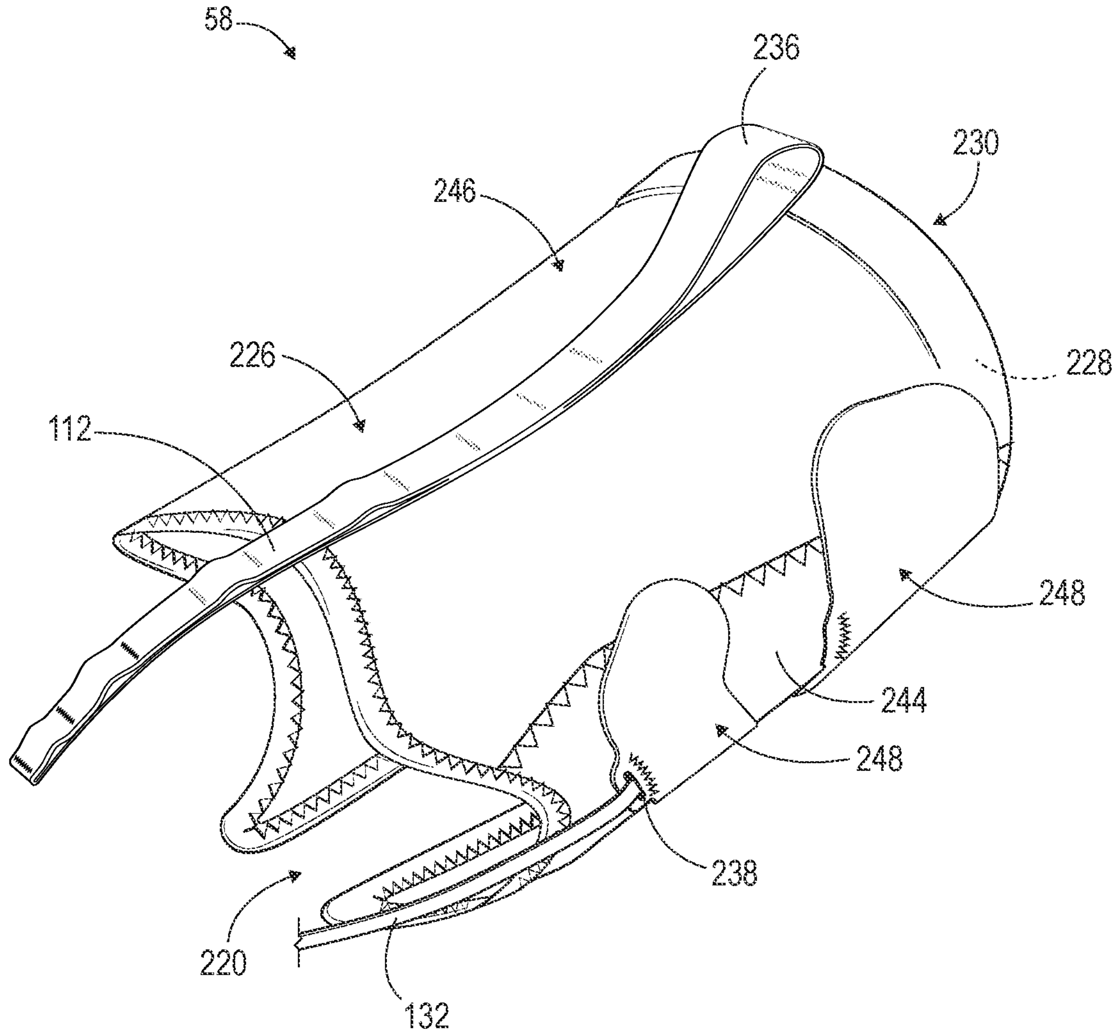
FIG. 21 is a perspective view of an example of an upper textile socket of presently disclosed prosthetic devices.
Figure 22:
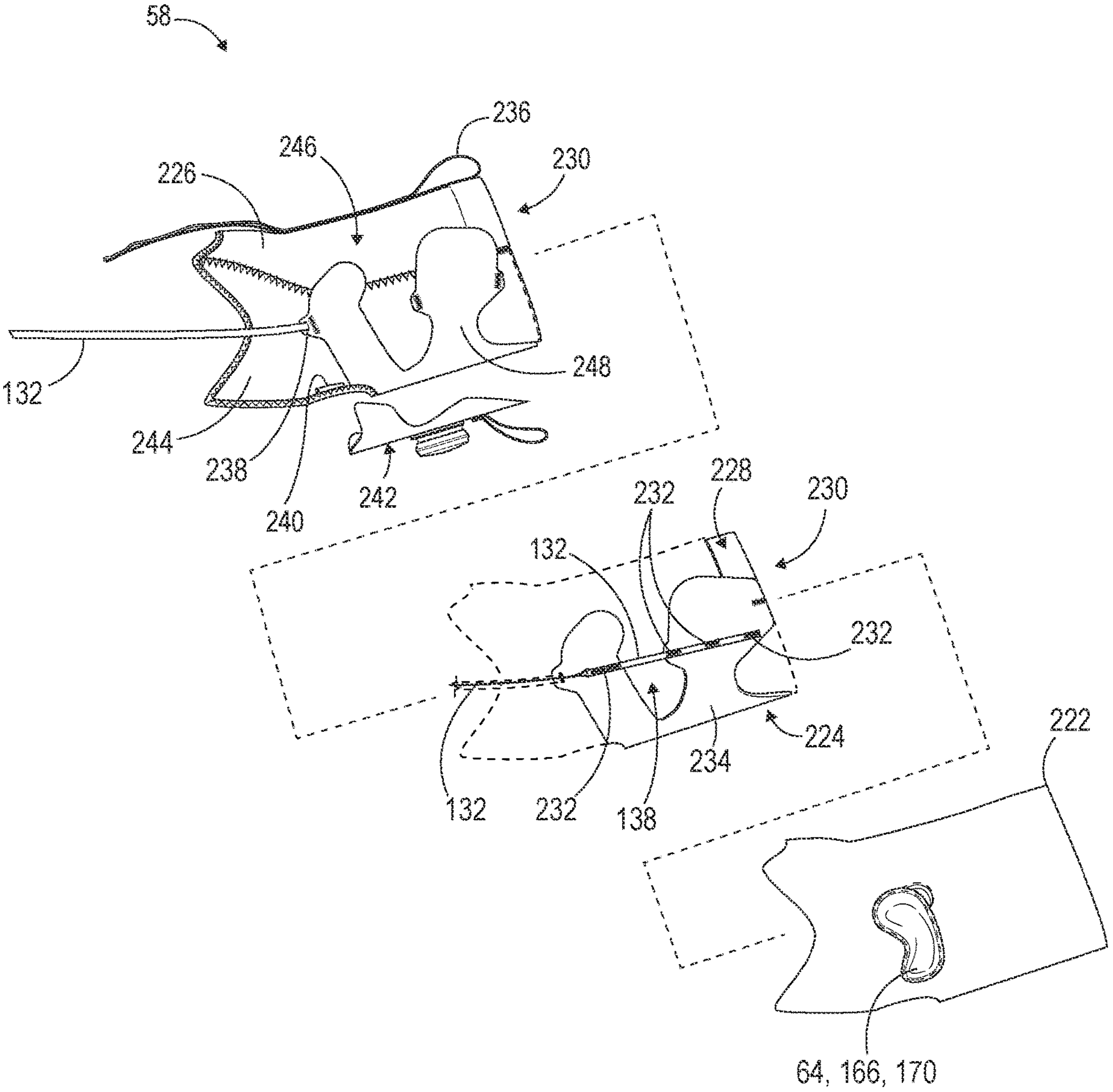
FIG. 22 is an exploded view of the upper textile socket of FIG. 21.

FIGS. 21-22 illustrate an example of upper textile socket 58 shown assembled (FIG. 21) and in an exploded view (FIG. 22). Upper textile socket 58 provides positioning for components of selective adjustment system 42 and independent counter 52, while allowing for expansion of tissues around the patient's joint of the residual limb during flexion. In prosthetic devices 40 configured for transradial amputations, upper textile socket 58 may specifically allow for expansion of the cubital fold region tissue of the residual limb, which may be enhanced by features such as a cutout 220 (e.g., to allow movement of the elbow or other joint of the residual limb) and the use of stretch fabric (e.g., four-way stretch fabric), such as Lycra® (spandex), polyester, or other knit fabrics, which sometimes may be referred to as polyspan (not to be confused with the nonwoven tissue of the same name). Upper textile socket 58 may advantageously be at least partially formed of four-way stretch fabrics, to allow for the greatest range of motion of the residual limb. Maximizing the coverage of the residual limb with regions of four-way stretch material may provide unexpected advantages over the use of merely two-way stretch fabrics, given that the expansion of tissue on limb flexion often is perceived to be primarily radial. In some applications, four-way stretch fabrics may be better suited to match the expansion of tissue. For example, as described in FIGS. 3 and 4 in connection with the elbow joint, the skin surface itself in flexion also undergoes significant stretch in the axial direction.

Like lower textile socket 56, upper textile socket 58 may be formed of a plurality of layers that are bonded and/or stitched together, such as an upper socket liner 222, an upper socket middle layer 224, and an upper socket outer layer 226. Upper socket liner 222 generally is configured to engage with the residual limb, and may be in direct contact with patient's skin of the residual limb when prosthetic device 40 is worn. As shown in FIG. 22, upper socket liner 222 may include one or more interface pads 64, such as elbow interface pads 166 (medial elbow interface pad 170 is visible in FIG. 22), which may be laminated and/or stitched within a stretch fabric (e.g., four-way stretch fabric), such as Lycra® (spandex), polyspan, or similar. Upper socket middle layer 224 may be configured to add cushioning and structural support. In an exemplary example, upper socket middle layer 224 may be formed at least partially of a 4D-spacer mesh material, though many other materials and types of fabrics are also suitable. The textile(s) used for upper socket middle layer 224 may be selected to provide some level of padding or cushioning from independent counter 52. Additionally or alternatively, a main body 234 of upper socket middle layer 224 may have a footprint, or profile, that is similar in shape and size to independent counter 52, such that upper socket middle layer 224 may underlie independent counter 52. In some examples, upper socket middle layer 224 is fixed to upper socket outer layer 226 and upper socket liner 222 by a perimeter stitch extending around the perimeter or sew channel of independent counter 52.

Upper socket middle layer 224 may be coupled to flexion fixed line 132, which may extend distally from upper textile socket 58. Specifically, flexion fixed line 132 may be anchored (e.g., terminate at) upper socket middle layer 224, such as via stitching or tacking 232. Upper socket middle layer 224 also may include an elastic strap 228 extending circumferentially at least partially around a proximal opening 230 of upper socket middle layer 224. Proximal opening 230 is configured to receive the residual limb therethrough, and elastic strap 228 is configured to help secure upper textile socket 58 around the residual limb and avoid sag of the material encircling residual limb 38.

Upper socket outer layer 226 may be configured to protect upper socket middle layer 224 and upper socket liner 222, with upper socket middle layer 224 being sandwiched between upper socket outer layer 226 and upper socket liner 222. Independent counter 52 may be engaged with upper socket outer layer 226, such as by being stitched to upper socket outer layer 226 around a perimeter of independent counter 52. In some examples, upper socket outer layer 226 includes a socket tab or pull loop 236 configured to aid in donning prosthetic device 40. In the example of FIGS. 21-22, socket pull loop 236 is positioned on the anterior side of the residual limb when prosthetic device 40 is worn; though in other examples, socket pull loop 236 may be positioned elsewhere with respect to upper textile socket 58 and/or the residual limb. Flexion fixed line 132 may exit upper textile socket 58 through an exit port 238, while a balancing lace guide 240 may provide a guiding channel through which balancing lace 98 passes. Upper socket outer layer 226 may be formed of a plurality of different materials. In an exemplary, non-limiting example, upper socket outer layer 226 may include a stretch-woven fabric 244 having a first degree of stretch, a second fabric 246 (e.g., polyspan) having a second degree of stretch, and an overlay 248, which may be microsuede, for example, or other non-stretch or low-stretch material.

Figure 23:
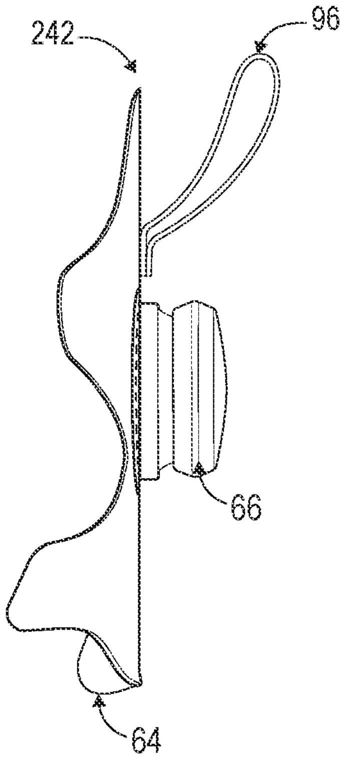
FIG. 23 is a side elevation view of an example of a back panel that may be integrated into a textile socket of disclosed prosthetic devices.
Figure 24:
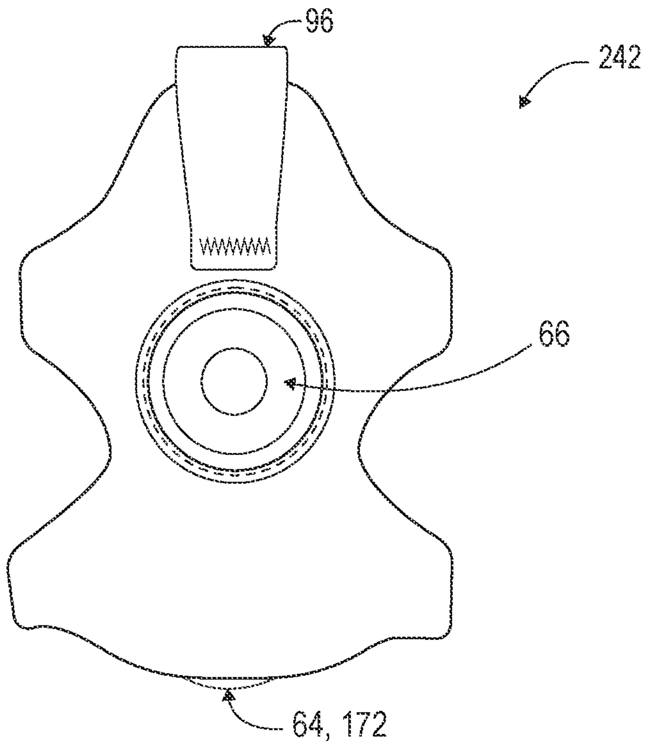
FIG. 24 is a top plan view of the back panel of FIG. 23.

Upper textile socket 58 also may include a back panel 242, which may be sandwiched between upper socket outer layer 226 and independent counter 52. Back panel 242 is best shown in FIGS. 23-24. Back panel 242 may be provided to house various components of prosthetic device 40, so that upper textile socket 58 may retain stretch characteristics and maximize comfort and range of motion of the residual limb. For example, back panel 242 may house counter pull loop 96, proximal tensioning reel 66, and one or more interface pads 64, such as posterior elbow pad 172 (e.g., to support the patient's olecranon fossa).

FIGS. 25-29 highlight details of examples of selective adjustment system 42. In addition to providing compression to elongate counters 46, independent counter 52, and socket 44 and maintaining a snug fit with the residual limb through the range of motion of the residual limb, selective adjustment system 42 effectively forms a plurality of hinges that connect upper textile socket 58 and lower textile socket 56 and/or that connect elongate counters 46 to one or more independent counters 52. While the components of selective adjustment system 42 are discussed independently in the context of FIGS. 25-29, for clarity, it is to be understood that the components of selective adjustment system 42 work together, in connection with socket 44 and chassis 48, to create the overall effects and advantages of disclosed prosthetic devices 40.

Figure 25:
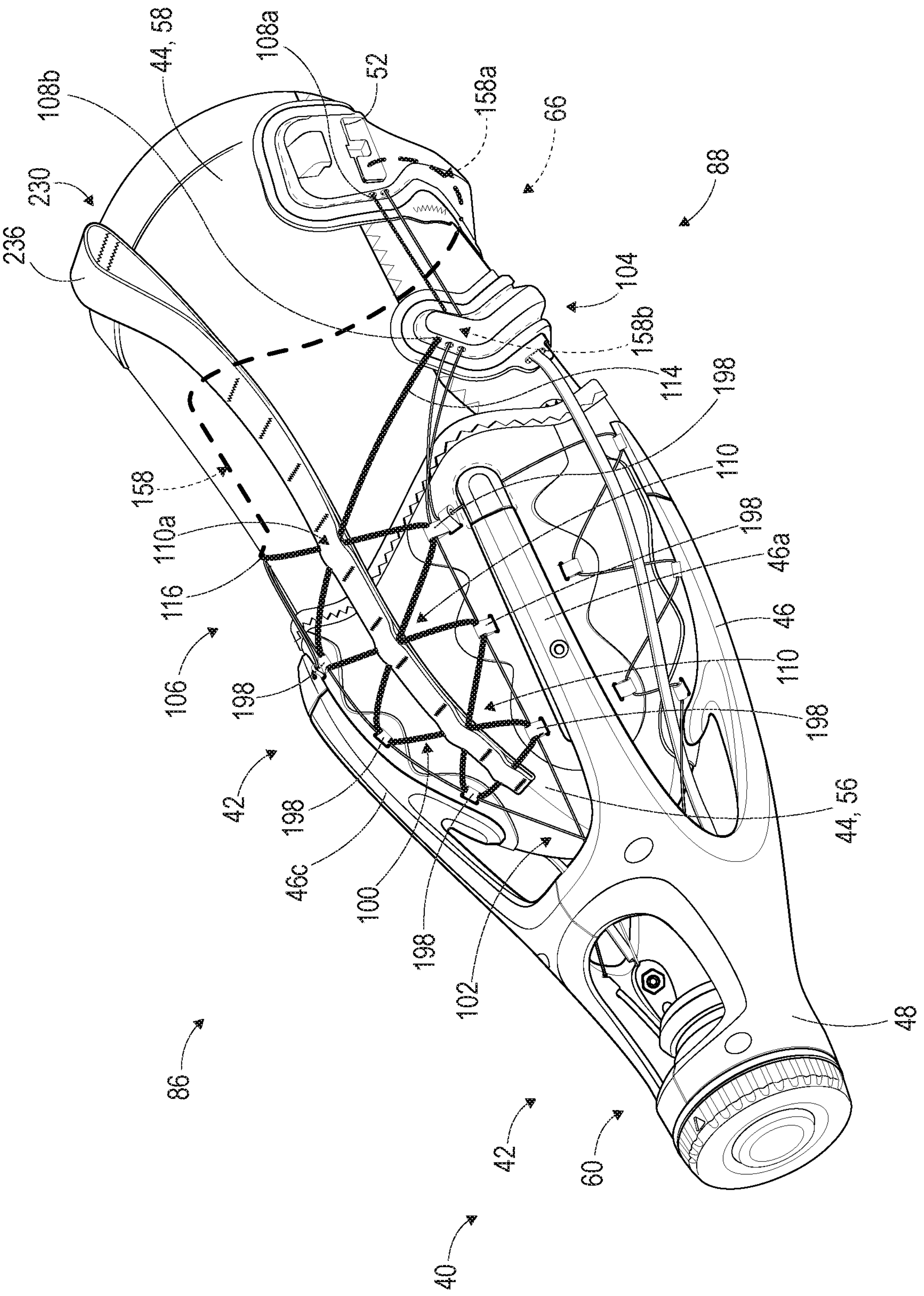
FIG. 25 is a perspective view of an example of a top lace of a selective adjustment system of disclosed prosthetic devices.

FIG. 25 highlights top lace 100 of selective adjustment system 42. The tension of top lace 100 may be adjusted via proximal tensioning reel 66. Specifically, proximal tensioning reel 66 (e.g., a BOA® reel or other type of tensioning reel) may be configured to selectively tighten or release top lace 100 by twisting, locking, and/or releasing proximal tensioning reel 66. Top lace 100 may be continuous from proximal tensioning reel 66 to a distal end region 102 of lower textile socket 56, and generally travels distally from proximal tensioning reel 66. As proximal tensioning reel 66 in this example is engaged with independent counter 52 and positioned on a posterior side 104 of socket 44, top lace 100 may extend from posterior side 104 to an anterior side 106 of socket 44, as shown in FIG. 25.

From proximal tensioning reel 66, top lace 100 may leave proximal tensioning reel 66 at exit ports 108*c* (FIG. 16), and extend through one or more internal lace guides 158 of independent counter 52. Specifically, in the example of FIG. 25, top lace 100 extends medially and laterally from proximal tensioning reel 66, through internal lace guides 158*a*, exiting independent counter 52 at a top lace exit port 108*a* on either side of prosthetic device 40. Top lace 100 then travels distally and enters internal lace guides 158*b*, also in independent counter 52, exiting internal lace guides 158 at top lace exit ports 108*b* on either side of prosthetic device 40. From there, top lace 100 crosses itself a plurality of times as the top lace travels distally along anterior side 106 of socket 44. Specifically, a medial portion 114 of top lace 100 travels towards lateral side 86 of prosthetic device 40 after leaving exit port 108*b* on medial side 88 of prosthetic device 40, while a lateral portion 116 of top lace 100 travels towards medial side 88 of prosthetic device 40 after leaving exit port 108*b* on lateral side 86 of prosthetic device 40. Medial portion 114 and lateral portion 116 of top lace 100 then cross paths on anterior side 106 of socket 44, and continue until each portion reaches a respective lace guide 198. In the example of FIG. 25, top lace 100 crosses itself three times along anterior side 106 of socket 44, such that three crossings 110 are created.

To create this arrangement, each portion of top lace 100 may be threaded through lace guides 198 to change the direction of each respective portion of top lace 100 as it travels distally along socket 44, similar to how shoe laces are commonly threaded through eyelets of a shoe. A most proximal crossing 110*a* may be configured to be positioned distal to the prominence of the bicep tendon in the cubital fold of the patient's elbow. Crossings 110 may be formed through a webbing 112 extending along anterior side 106 of socket 44, from socket pull loop 236, though socket pull loop 236 and webbing 112 may be separate structures in various examples. Webbing 112 may include a plurality of segments, or pass-throughs, through which top lace 100 may pass, with webbing 112 configured to protect top lace from snagging, and to help keep top lace 100 engaged with socket 44. Due to the arrangement of top lace 100 with respect to the other components of prosthetic device 40, top lace 100 is placed under increased tension when the residual limb is extended. This is because during extension of the residual limb, an overall distance from distal end region 60 of chassis 48 to proximal opening 230 of upper textile socket 58 is increased, thereby tensioning top lace 100. Selectively adjusting the tension of top lace 100 via proximal tensioning reel 66 may function to pull together elongate counters 46*a*, 46*c* on anterior side 106 of socket 44, due to interaction between lace guides 198 and keyed-rail system 140, as discussed above. Specifically, because lace guides 198 may be integrated into (e.g., laminated with) reinforcing overlays 200, which also house rails 146 to which elongate counters 46 are secured, when tightening motion of top lace 100 pulls lace guides 198 on opposite sides of socket 44 towards each other (e.g., towards webbing 112), movement of the lace guides 198 pulls rails 146 and the associated elongate counters 46 attached thereto closer together also.

Figure 26:
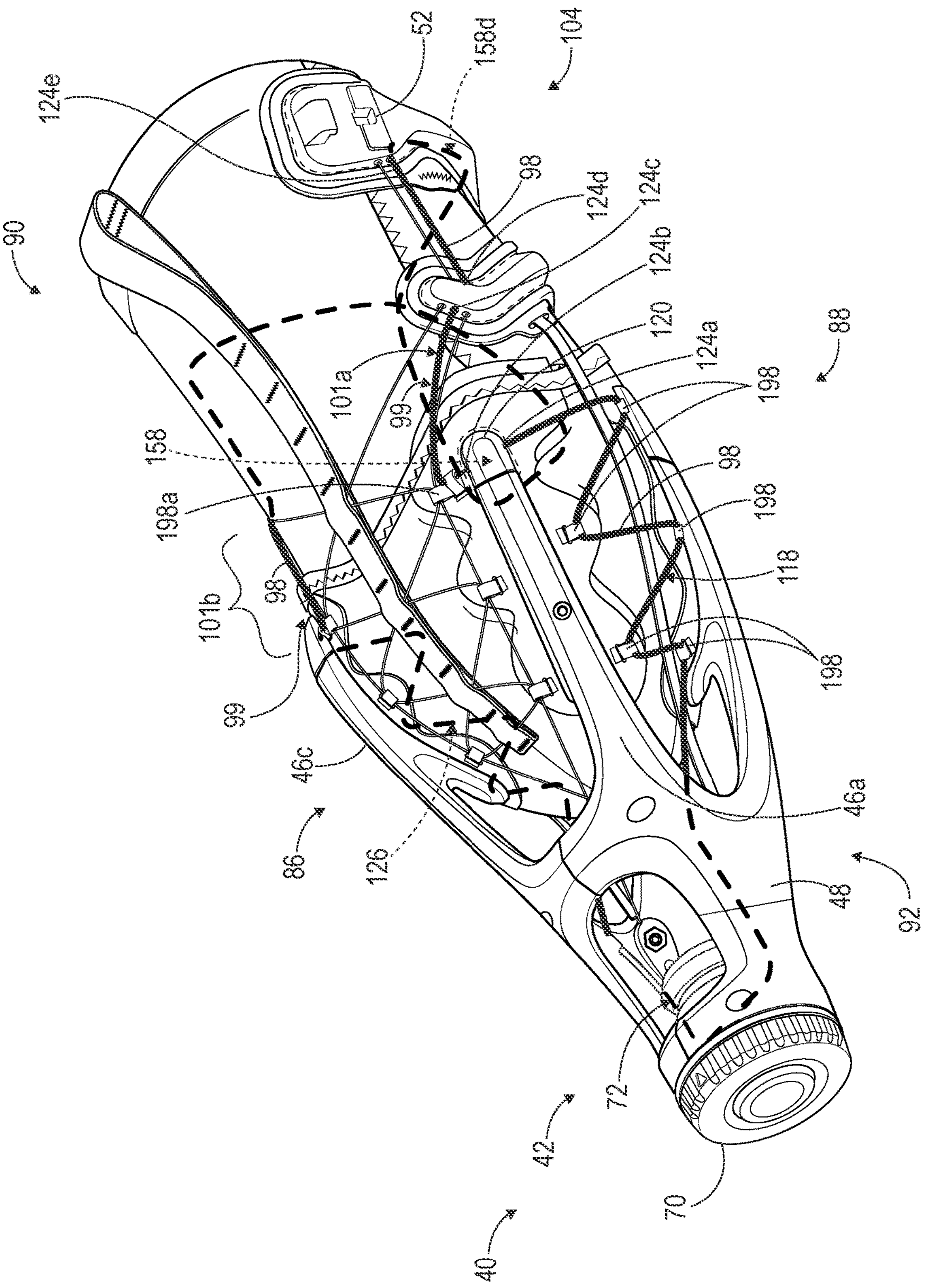
FIG. 26 is a perspective view of an example of a balancing lace of a selective adjustment system of disclosed prosthetic devices.

FIG. 26 highlights balancing lace 98 of selective adjustment system 42. Chassis 48 includes distal tensioning reel 72, which is configured to adjust the tension of balancing lace 98. When tightened by distal tensioning reel 72, balancing lace 98 is configured to pull independent counter 52 towards elongate counters 46, thereby drawing the residual limb into socket 44. Balancing lace 98 extends proximally from distal tensioning reel 72, along medial side 88 and lateral side 86 of prosthetic device 40. Balancing lace 98 may extend proximally from distal tensioning reel 72 to independent counter 52, and may form a zigzag pattern along lower textile socket 56 on both medial 88 and lateral 86 sides of prosthetic device 40 as balancing lace 98 passes through lace guides 198 on lower textile socket 56. Balancing lace 98 also passes through a plurality of internal lace guides 158, via a plurality of balancing lace entry and exit ports 124. For example, when a medial portion 118 of balancing lace 98 reaches a respective proximal cap 120 of elongate counter 46*a*, balancing lace 98 then enters an internal lace guide 158 in proximal cap 120 via a balancing lace entry port 124*a*, exits the internal lace guide 158 of proximal cap 120 at balancing lace exit port 124*b*, and then changes direction via lace guide 198*a*, such that balancing lace 98 turns to enter internal lace guide 158*c* (see FIG. 16) of independent counter 52 at balancing lace entry port 124*c*. Balancing lace 98 then exits independent counter 52 at balancing lace exit port 124*d*, and then travels proximally to enter another internal lace guide 158*d* of independent counter 52 at balancing lace entry port 124*e*. While medial portion 118 of balancing lace 98 is most easily seen in FIG. 26, a lateral portion 126 of balancing lace 98 follows a symmetrical path on lateral side 86 of prosthetic device 40. Once medial and lateral portions 118, 126 of balancing lace 98 enter internal lace guides 158*d* in independent counter 52, medial and lateral portions 118, 126 of balancing lace 98 travel to the posterior side 104 of socket 44, crossing each other distal to proximal tensioning reel 66, as best seen in FIG. 16 (indicated at 128).

Figure 27:
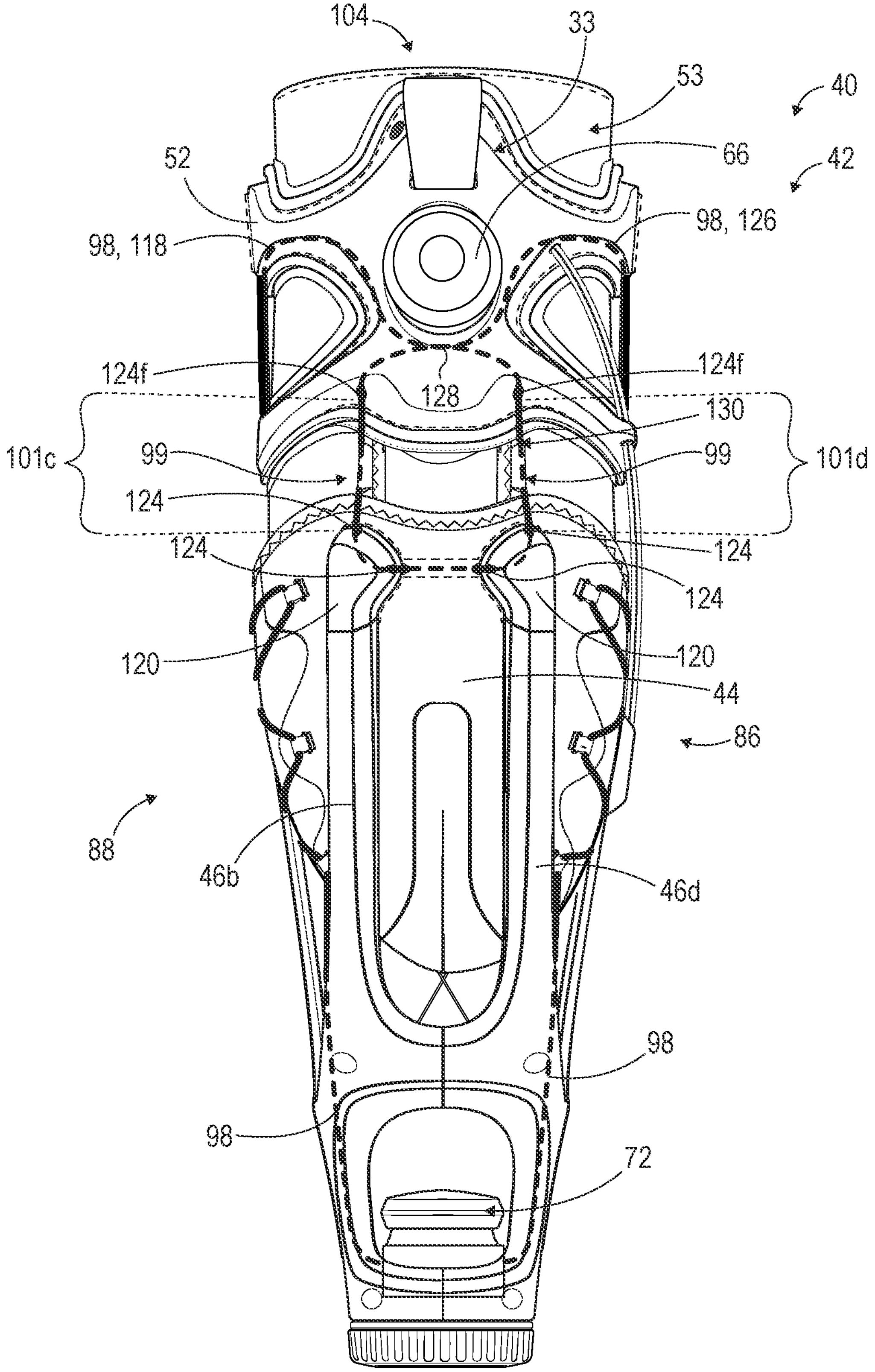
FIG. 27 is a bottom plan view of the balancing lace of FIG. 26.

With continued reference to FIGS. 16 and 26, and also to FIG. 27, after crossing at 128, balancing lace 98 exits internal lace guide 158*d* of independent counter 52 at exit ports 124*f* (FIG. 16) and extends distally on posterior side 104 of prosthetic device 40. When balancing lace 98 reaches lower textile socket 56 on posterior side 104 of prosthetic device 40, the balancing lace enters and exits proximal caps 120 of elongate counters 46*b*, 46*d*, traveling through internal lace guides 158 and through proximal caps 120 to form a looped path 130. This looped path 130 effectively creates a U-turn in balancing lace 98, and serves as the anchor of balancing lace 98.

Prosthetic device 40 may be said to form one or more flexible hinges 99. In some examples, each hinge 99 may be a respective segment of any lace, fiber, wire, rope, etc. of selective adjustment system 42 extending between the last (e.g., proximal-most or distal-most) point on upper or lower textile socket 58, 56 where it is constrained by a channel, lace guide, or other structure, such that either socket 56, 58 is free to move save for these constraints. In some examples, balancing lace 98 may be configured to function as one or more flexible hinges 99, which may be positioned on anterior, posterior, medial, and/or lateral sides of residual limb 38. In other words, balancing lace 98 may be said to create a plurality of balancing lace hinges 101 (an example of hinges 99), via portions or segments of balancing lace 98. The segments of balancing lace 98 that form hinges 99 are defined relative to upper textile socket 58, lower textile socket 56, elongate counters 46, and/or independent counter 52, rather than by any absolute location along balancing lace 98. Generally, balancing lace hinges 101 are formed by portions of balancing lace 98 extending between upper textile socket 58 and lower textile socket 56, and are configured to form flexible connections on which the two textile sockets 56, 58 and their respective counters 46, 52 are articulated, to allow the intermediate joint to bend.

Balancing lace hinges 101 on the anterior side 90 of prosthetic device 40 (e.g., configured to be positioned on the anterior side of the residual limb) may be effectively shortened during flexion of the residual limb, while balancing lace hinges 101 on the posterior side 92 of prosthetic device 40 (e.g., configured to be positioned on the posterior side of the residual limb) are effectively lengthened during flexion of the residual limb. Similarly, balancing lace hinges 101 on anterior side 90 may be effectively lengthened during extension of residual limb 38, while balancing lace hinges 101 on posterior side 92 may be effectively shortened during extension of the residual limb. In doing this, while the wire, rope, lace, or cable forming balancing lace 98 itself may remain mostly fixed, the effective shortening and lengthening of the segments forming balancing lace hinges 99 may allow for a fuller range of motion while still functioning during tensile loading. Two balancing lace hinges 101 are best visible in FIG. 26, namely a medial anterior balancing lace hinge 101*a* and a lateral anterior balancing lace hinge 101*b* on anterior side 90 of prosthetic device 40. Medial anterior balancing lace hinge 101*a* is the portion, or segment, of balancing lace 98 extending between elongate counter 46*a* (adjacent lace guide 198*a*) and entry port 124*c* in independent counter 52. Lateral anterior balancing lace hinge 101*b* is the portion, or segment, of balancing lace 98 extending between elongate counter 46*c* and a similar entry port 124 on the lateral side of independent counter 52. Two balancing lace hinges 101 are best visible in FIG. 27, namely a medial posterior balancing lace hinge 101*c* and a lateral posterior balancing lace hinge 101*d* on posterior side 92 of prosthetic device 40. Medial posterior balancing lace hinge 101*c* is the portion, or segment, of balancing lace 98 extending between elongate counter 46*b* and entry port 124*f* on the medial side of independent counter 52. Lateral posterior balancing lace hinge 101*d* is the portion, or segment, of balancing lace 98 extending between elongate counter 46*d* and entry port 124*f* on the lateral side of independent counter 52.

Thus, balancing lace 98 may be said to create four flexible hinges 99 in this example. As balancing lace 98 is free to move through and within internal lace guides 158, the length of the portion or segment of balancing lace 98 that forms a respective balancing lace hinge 101 may increase and decrease as the residual limb is moved (which causes movement of independent counter 52 relative to elongate counters 46). Balancing lace hinges 101 thus may form two sets of flexible hinges that may be configured to equalize lengths to maintain the fit of socket 44 on residual limb 38 throughout the range of motion of the residual limb. Hinges 99 are thus part of the overall system that tightens prosthetic device 40 around residual limb (e.g., hinges 99 are part of the system or interaction between selective adjustment system 32, elongate counters 46 or chassis 48, and independent counter 52). In some examples, hinges 99 are displaced from the neutral axis.

Top lace 100 may be similarly configured to function as one or more flexible hinges 99, which may be positioned on anterior, posterior, medial, and/or lateral sides of residual limb 38. In other words, top lace 100 may be said to create a plurality of top lace hinges 103 (an example of hinges 99), via portions or segments of top lace 100. Top lace hinges 103 are visible in all of FIGS. 25-29, but only labeled in FIG. 28, for clarity. The segments of top lace 100 that form hinges 99 are defined relative to components of prosthetic device 40, rather than by any absolute location along top lace 100. Generally, top lace hinges 103 are formed by portions of top lace 100 extending from independent counter 52 to where they pass through webbing 112, and are configured to add flexibility to the fit of prosthetic device 40 and contribute to the dynamic volume created therein. In this example, top lace hinges 103 cross over or near the elbow joint of the residual limb. For example, a first top lace hinge 103*a* may be formed by the portion, or segment, of top lace 100 that extends medially from a portion of independent counter 52 on lateral side 86 to webbing 112. Similarly, a second top lace hinge 103*c* may be formed by the portion, or segment, of top lace 100 that extends medially from a portion of independent counter 52 on medial side 88 (entering/exiting independent counter 52 at an entry port 124 as described herein) to webbing 112. As top lace 100 is free to move through and within internal lace guides 158, the length of the portion or segment of top lace 100 that forms a respective top lace hinge 103 may increase and decrease as the residual limb is moved (which causes movement of independent counter 52 relative to elongate counters 46).

Figure 28:
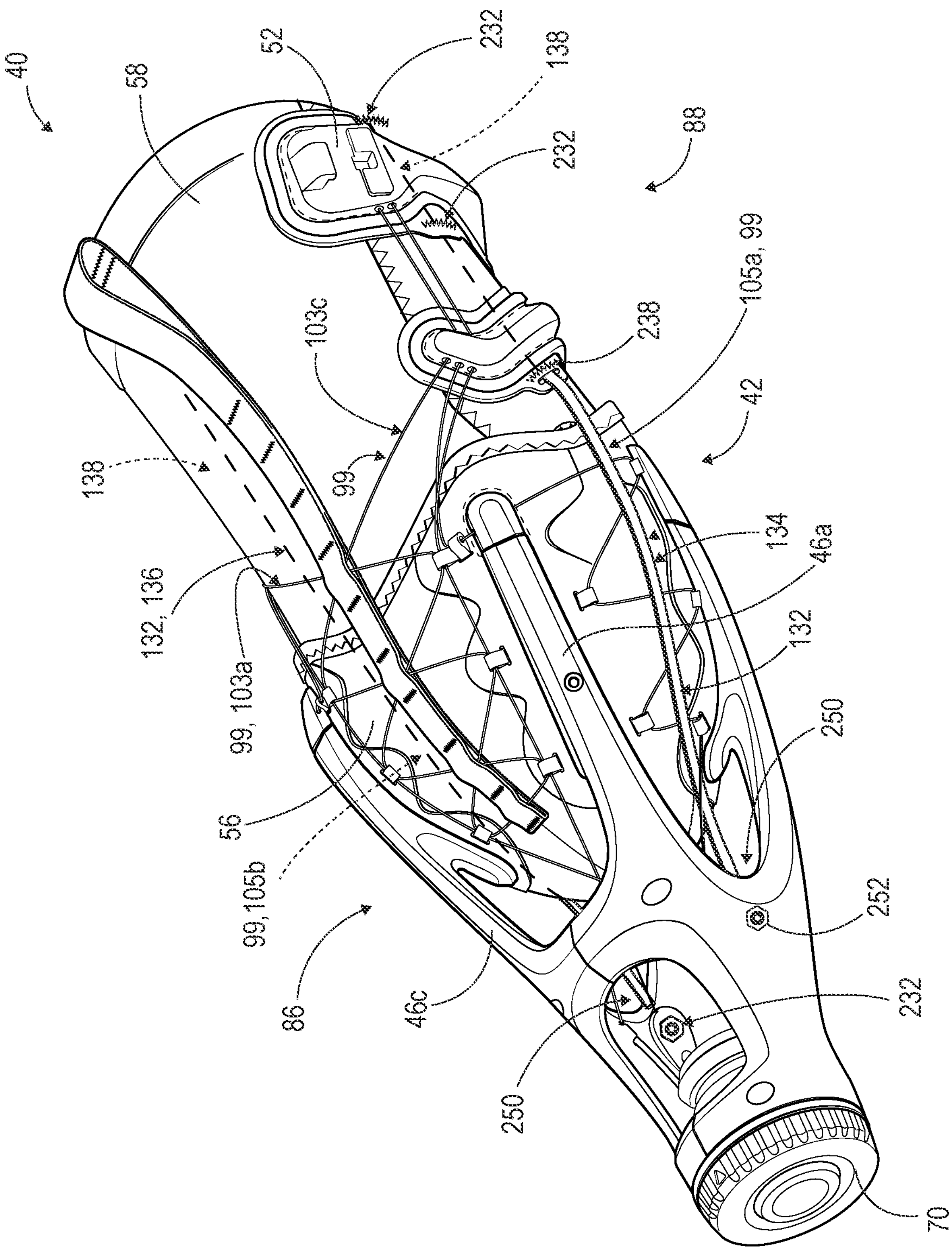
FIG. 28 is a perspective view of an example of a flexion fixed line of a selective adjustment system of disclosed prosthetic devices.

FIG. 28 highlights flexion fixed line 132, which may be configured to create a set distance between end effector attachment unit 70 and independent counter 52 when the residual limb is at full flexion. Flexion fixed line 132 may include a medial portion 134 that extends proximally along lower textile socket 56 and continues along upper textile socket 58 on medial side 88 of prosthetic device 40. Similarly, flexion fixed line 132 may include a lateral portion 136 which extends proximally along lower textile socket 56 and continues along upper textile socket 58 on lateral side 86 of prosthetic device 40. A proximal end region 138 of both medial and lateral portions 134, 136 of flexion fixed line 132 is fixed to upper textile socket 58, as described in connection with FIG. 22, such as by entering upper textile socket 58 through flexion fixed line port 238 and being stitched to upper textile socket 58 at 232. An origination region 250 of medial and lateral portions 134, 136 of flexion fixed line 132 is secured to chassis 48 via a set screw 252 or other fastener. In some examples, some or all of the exposed portion of flexion fixed line 132 (e.g., the portions outside of upper textile socket 58) may be partially or fully enclosed in a housing or sheath and/or coated with a protective coating. In some examples, the housing, sheath, or coating may be coupled to lower textile socket 56 and/or to balancing lace 98. Additionally or alternatively, portions of flexion flexed line 132 may be stitched through the housing, sheath, or coating such that spaced apart segments of flexion fixed line 132 pass externally, or laterally, to the housing, sheath, or coating. In some examples, balancing lace 98 may pass between such portions of flexion fixed line and the housing or coating, to help position flexion fixed line 132 with respect to lower textile socket 56 (e.g., to keep flexion fixed line 132 close to lower textile socket 56, while still allowing anterior and posterior movement of flexion fixed line 132 relative to lower textile socket 56). Additionally or alternatively, balancing lace 98 may pierce the housing, sheath, or coating of flexion fixed line 132 each time balancing lace 98 and flexion fixed line 132 cross, or pass by one another. A set length of flexion fixed line 132 can be lengthened or shortened by removing set screw 252 (or other fastener or tensioning device) and translating origination region 250 of flexion fixed line 132 relative to set screw 252. While the example of FIG. 28 illustrates flexion fixed line 132 in the form of two separate fixed lines (i.e., medial portion 134 and lateral portion 136), in other examples, flexion fixed line 132 may be a single continuous line with medial and lateral portions 134, 136 connected on posterior side 92 of prosthetic device 40.

Flexion fixed line 132 is coupled to chassis 48 and extends to engage with independent counter 52, and thus may be configured to function as one or more flexible hinges 99, which may be positioned on anterior, posterior, medial, and/or lateral sides of residual limb 38. In other words, flexion fixed line 132 may be said to create, or include, a plurality of flexion line hinges 105 (an example of hinges 99), where flexion fixed line 132 connects upper and lower textile sockets 58 and 56, between independent counter 52 and balancing lace 98. The segments of flexion fixed line 132 that form hinges 99 are defined relative to where it exits independent counter 52, rather than by any absolute location along flexion fixed line 132. Generally, flexion line hinges 105 are formed by portions of flexion fixed line 132 extending between upper textile socket 58 and lower textile socket 56, and are configured to add flexibility to the fit of prosthetic device 40 and contribute to the dynamic volume created therein. In this example, flexion fixed line 132 includes a medial flexion line hinge **105*a* on medial side 88 of prosthetic device 40, and a lateral flexion line hinge 105*b* on lateral side 86 of prosthetic device 40. Medial flexion line hinge 105*a* is the portion, or segment, of flexion fixed line 132 that extends from where flexion fixed line 132 makes its proximal-most crossing of balancing lace 98, to entry/exit port 238 of upper textile socket 58 on medial side 88 of prosthetic device 40. Similarly, lateral flexion line hinge 105*b* is the portion, or segment, of flexion fixed line 132 that extends from where flexion fixed line 132 makes its proximal-most crossing of balancing lace 98, to entry/exit port 238 of upper textile socket 58 on lateral side 86 of prosthetic device 40**.

Figure 29:
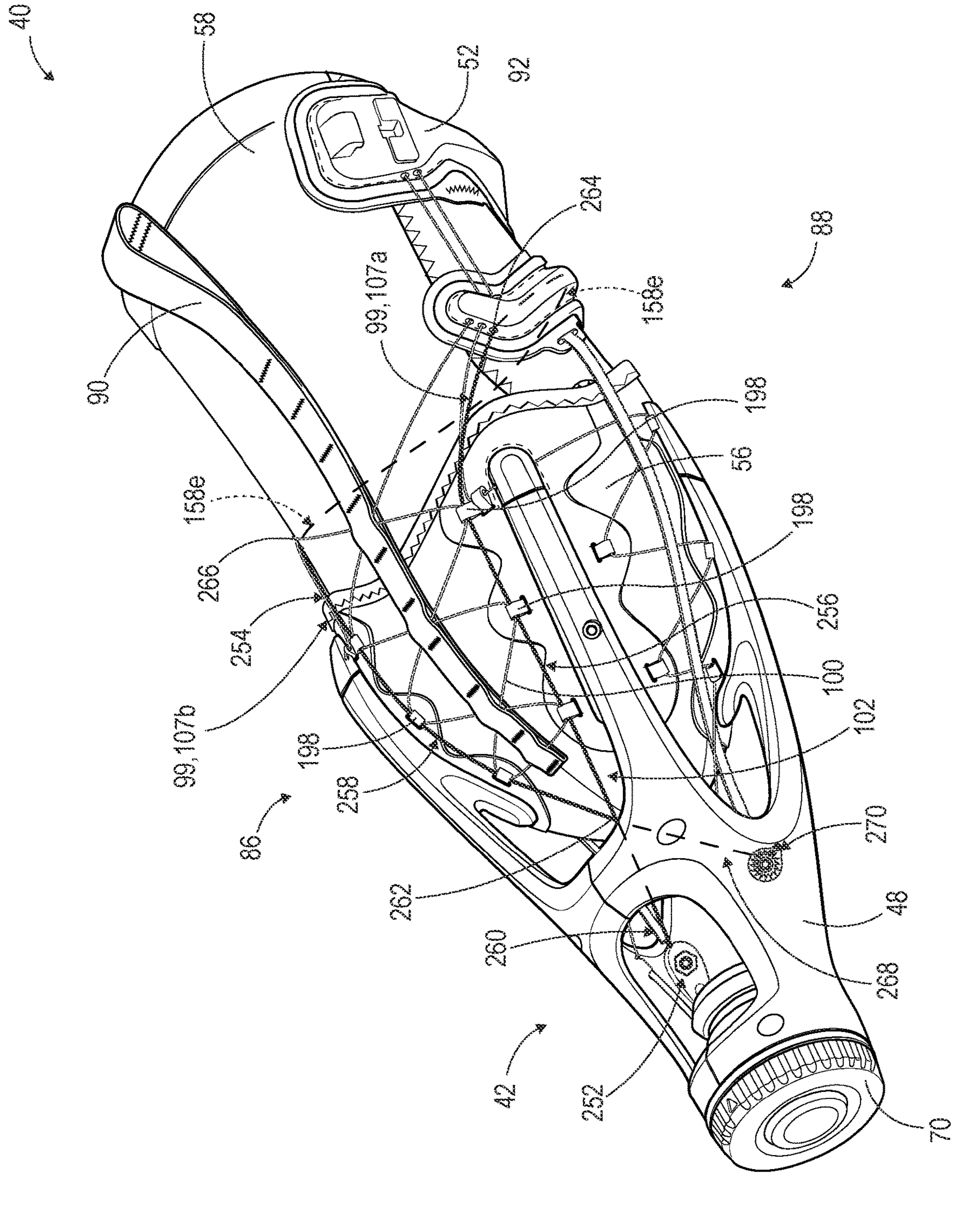
FIG. 29 is a perspective view of an example of an extension fixed line of a selective adjustment system of disclosed prosthetic devices.

FIG. 29 illustrates extension fixed line 254, which is configured to create a set distance from end effector attachment unit 70 to independent counter 52 when the residual limb is at full extension. Similarly to flexion fixed line 132, extension fixed line 254 may include a medial portion 256 extending proximally along lower textile socket 56, on anterior side 90 of prosthetic device 40. Further, extension fixed line 254 may include a lateral portion 258 that extends proximally along lower textile socket 56 on anterior side 90 of prosthetic device 40. An origination region 260 of extension fixed line 254 is secured to chassis 48 via a set screw 252 or other fastener. A set length of extension fixed line 254 can be lengthened or shortened by removing set screw 252 (or other fastener) and translating origination region 260 of extension fixed line 254 relative to set screw 252. Set screw 252 for extension fixed line 254 may be the same set screw as for flexion fixed line 132, or separate set screws 252 may be used for each fixed line 132, 254. Medial and lateral portions 256, 258 of extension fixed line 254 may cross each other at 262, near distal end region 102 of lower textile socket 56. From origination region 260, extension fixed line 254 extends proximally from chassis 48 to independent counter 52. Specifically, medial portion 256 of extension fixed line 254 extends proximally along lower textile socket 56, until extension fixed line enters internal lace guide **158*e* of independent counter 52 (see also FIG. 16) at port 264. As extension fixed line 254 passes through internal lace guide 158*e*, the extension fixed line extends, or travels, circumferentially along posterior side 92 of prosthetic device 40, exiting independent counter 52 though port 266 on lateral side 86 of prosthetic device 40. Lateral portion 258 of extension fixed line 254 then travels distally along lower textile socket 56 on anterior side 90 of prosthetic device, and then crosses over to medial side 88 near distal end region 102 of lower textile socket 56. Extension fixed line 254 then terminates at an extension fixed line terminus 268. A ratcheted spool or other adjustment mechanism 270 may be operatively coupled to flexion fixed line 132 and/or extension fixed line 254 (such as to terminus 268 of extension fixed line 254). Said ratcheted spool 270 may be configured for micro-adjustments of a set length of flexion fixed line 132 and/or for micro-adjustments of a set length of extension fixed line 254**.

Extension fixed line 254 is configured to tighten, or be placed under increased tension, under loading of chassis 48, such that tensioning of extension fixed line 254 is configured to pull one or more interface pads (e.g., posterior elbow interface pad 172) into the residual limb (e.g., into the olecranon fossa of the residual limb). For example, extension fixed line 254 may pass through independent counter 52 posterior to one or more interface pads 64 of independent counter 52. Extension fixed line 254 and/or flexion fixed line 132 may include plastic tubing or other protective coating surrounding external portions of the fixed line (i.e., portions of the fixed line not within internal lace guides 158). As extension fixed line 254 travels along lower textile socket 56, it may pass through a plurality of lace guides 198 that guide the fixed line along the intended path. Said lace guides 198 also may receive top lace 100, as described herein.

Extension fixed line 254 is coupled to chassis 48 and extends to engage with independent counter 52, and thus may be configured to function as one or more flexible hinges 99, which may be positioned on anterior, posterior, medial, and/or lateral sides of residual limb 38. In other words, extension fixed line 254 may be said to create a plurality of extension line hinges 107 (an example of hinges 99), via portions or segments of extension fixed line 254. The segments of extension fixed line 254 that form hinges 99 are defined relative where extension fixed line 254 enters the proximal-most lace guides 198 on lower textile socket 56, rather than by any absolute location along extension fixed line 254. Generally, extension line hinges 107 are formed by portions of extension fixed line 254 extending between independent counter 52 and the first point redirecting extension fixed line 254 on lower socket 56 (a lace guide 198), and are configured to add flexibility to the fit of prosthetic device 40 and contribute to the dynamic volume created therein. In this example, extension fixed line 254 includes a medial extension line hinge **107*a* on medial side 88 of prosthetic device 40, and a lateral extension line hinge 107*b* on lateral side 86 of prosthetic device 40. Medial extension line hinge 107*a* is the portion, or segment, of extension fixed line 254 that extends from entry/exit port 264 on the medial side of independent counter 52 to the proximal-most lace guide 198 on the medial side of lower socket 56. Similarly, lateral extension line hinge 107*b* is the portion, or segment, of extension fixed line 254 that extends from a respective entry/exit port 264 on the lateral side of independent counter 52 to the proximal-most lace guide 198 on the lateral side of lower textile socket 56. Thus, with two hinges 99 created by extension fixed line 254, two hinges 99 created by flexion fixed line 132, two hinges 99 created by top lace 100, and four hinges 99 created by balancing lace 98, disclosed prosthetic devices 40 may include ten flexible hinges 99. Other examples of prosthetic device 40 may include more or fewer hinges 99**.

Figure 30:
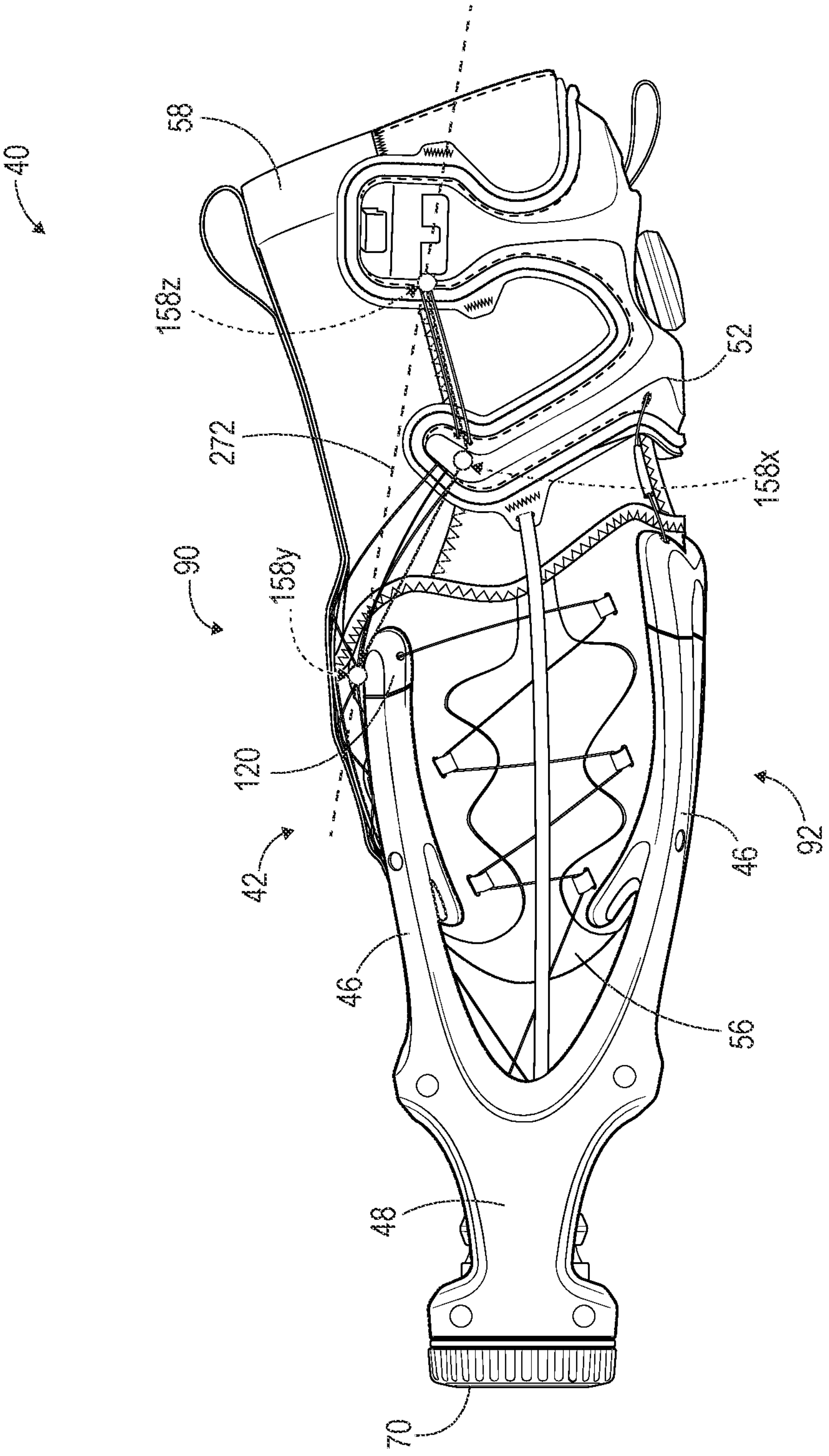
FIG. 30 is a side elevation view of an example of a selective adjustment system, highlighting a feature of the example of a selective adjustment system for disclosed prosthetic devices.

FIG. 30 illustrates a feature of an example of selective adjustment system 42, in which at least one internal lace guide 158*x* is placed posterior to an imaginary straight line 272 created between an anterior-most internal lace guide 158*y* extending through proximal cap 120 of elongate counter 46 and an anterior-most internal lace guide 158*z* extending through independent counter 52. While internal lace guide 158*y* may be positioned as far onto the anterior plane of the prosthetic device as possible, it may still be positioned to avoid the cubital fold region of the residual limb (or other area of a different residual limb). In some examples, the arrangement of lace guides 158*x*, 158*y*, and 158*z* forms, within all other constraints, an angle as much as possible less than 180 degrees (in the anterior and medial directions, in the sagittal and coronal planes, respectively) in order for the lace that travels through them to exert a medial and therefore compressive force on the counter that contains lace guide 158*x* and its underlying interface pad (e.g., medial elbow pad 170). Additionally, the tightening action upon extension only occurs to the extent that the sides of the angle (e.g., segments 158*x*-158*y* and 158*x*-158*z*) decrease upon flexion, and lengthen upon extension. To meet this limitation, the segments formed by these lace guide locations may follow a contour on the anterior side of the neutral axis of the joint that they transit (for a joint that flexes anteriorly).

Figure 31A:
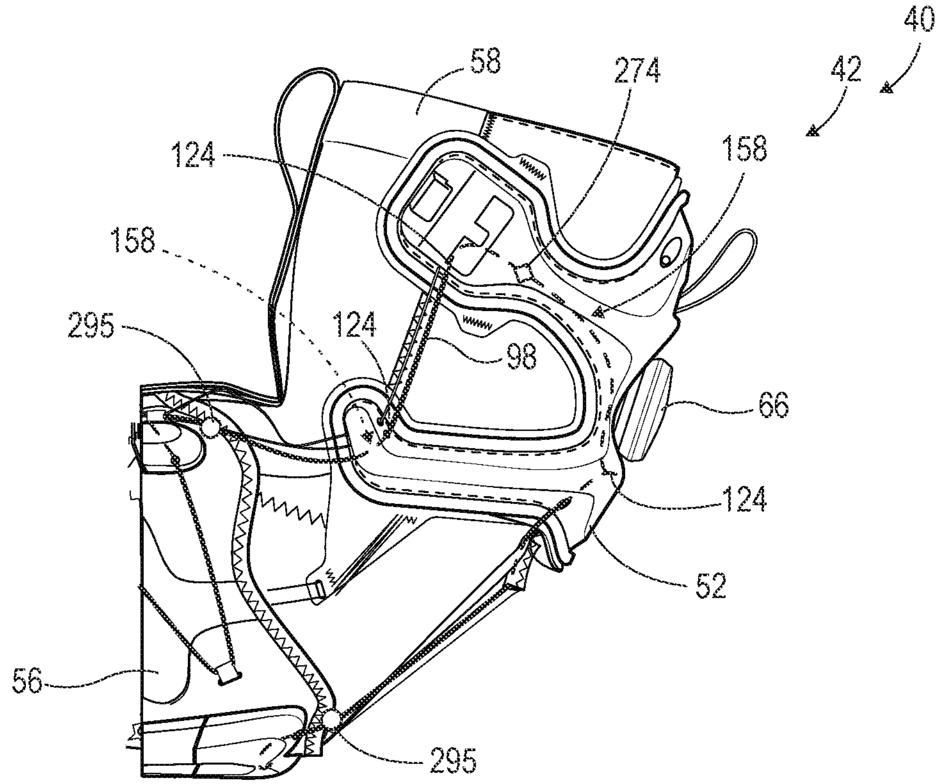
FIG. 31A is a side elevation view of an example of an independent counter of disclosed prosthetic devices, illustrating relative positions of locations on a balancing lace during flexion of the residual limb.
Figure 31B:
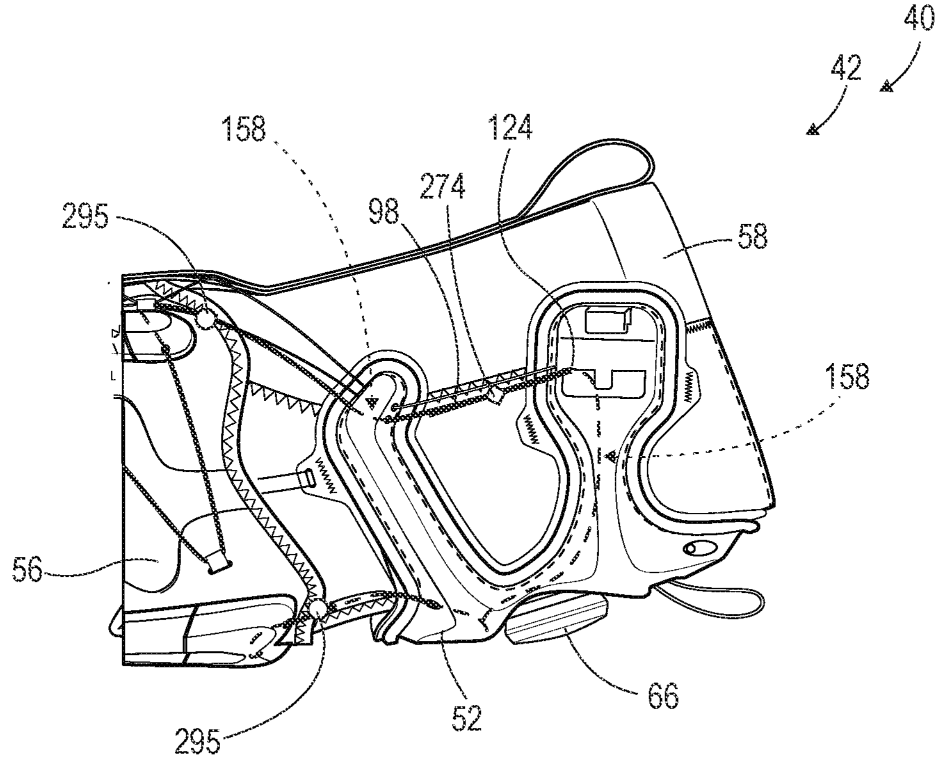
FIG. 31B is a side elevation view of the independent counter of FIG. 31A, illustrating relative positions of locations on a balancing lace during extension of the residual limb.

FIGS. 31A and 31B show two positions of independent counter 52 viewed from the medial side. FIG. 31A shows the arm in flexion, and FIG. 31B shows the arm at extension. FIGS. 31A-B illustrate an example of movement of balancing lace 98 within independent counter 52, as the residual limb and independent counter 52 are moved together between flexion (FIG. 31A), and extension (FIG. 31B), showing the relative positions of fixed locations on balancing lace 98. The solid portions of balancing lace 98 are external to independent counter 52, while the dashed portions of balancing lace 98 are internal to independent counter 52 (e.g., within an internal lace guide 158). While balancing lace 98 is free to move through its entire path, and does so somewhat to balance the differences between medial and lateral balancing lace 98 segment lengths, the apex of loop path 130 (which represents the furthest point along balancing lace 98 from distal tensioning reel 72) can be imagined as an anchor for balancing lace 98. It can therefore be helpful to imagine circle locations 295 where balancing lace 98 enters loop path 130 and returns to distal tensioning reel 72 as points where balancing lace 98 is fixed during movement of upper textile socket 58 and independent counter 52 with respect to lower textile socket 56. During such movement, independent counter 52 is sliding over the exposed portions of balancing lace 98, alternately lengthening and shortening the anterior and posterior exposed portions of balancing lace 98, or its hinges, 99

The diamond indicators 274 indicate a representative fixed location of balancing lace 98 that is positioned between lace entry ports 124*d* and 124*e* in FIG. 31B at extension, and that travels into internal lace guide 158*d* and is positioned therein when the residual limb is in flexion. Again, independent counter 52 may effectively move over balancing lace 98 during movement of the residual limb, with balancing lace 98 sliding within the internal lace guides 158 of independent counter 52 as the counter moves. This function may help independent counter 52 to maintains a secure connection to the bony prominences of the residual limb engaged by the interface pads, even as the textile sockets 56, 58 and selective adjustment system 42 allow the soft tissue of the residual limb the freedom to naturally move and expand and contract as the residual limb flexes, contracts, and extends.

Figure 32:
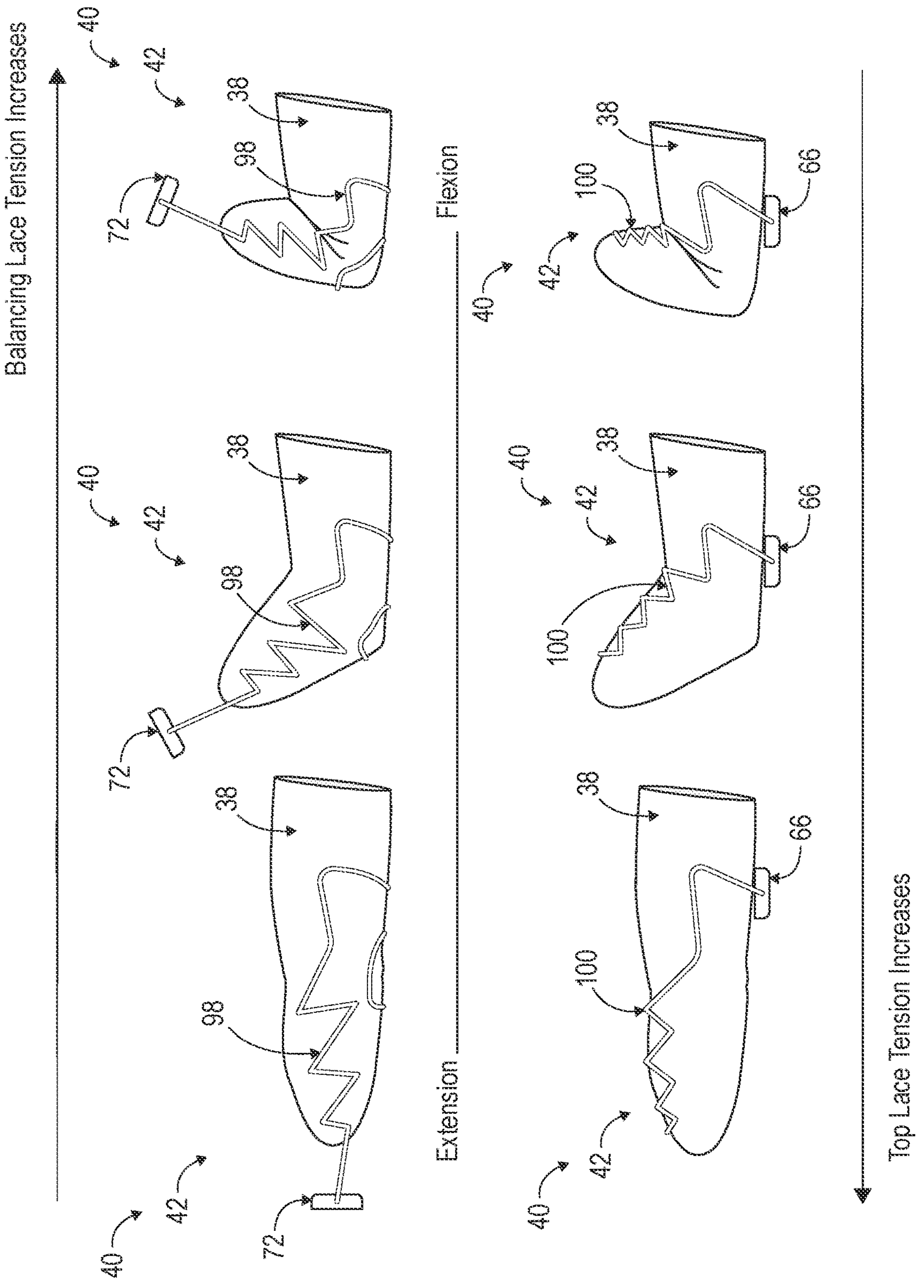
FIG. 32 is a schematic representation illustrating examples of relative tension in a balancing lace and a top lace, during extension and flexion of the residual limb.

FIG. 32 schematically represents residual limb 38 moving between extension and flexion, illustrating the relative changes of tension of balancing lace 98 and top lace 100. Balancing lace 98 is schematically represented extending proximally from distal tensioning reel 72, and top lace 100 is schematically represented extending distally from proximal tensioning reel 66. As represented in FIG. 32, the tension of balancing lace 98 increases slightly as residual limb 38 flexes, and decreases slightly as residual limb 38 is extended. The routing of balancing lace 98 through various lace guides and internal lace guides, as described herein, creates this result in balancing lace 98 during movement of residual limb 38. On the other hand, the tension of top lace 100 decreases as residual limb 38 flexes, and increases as residual limb 38 is extended. Again, the routing of top lace 100 through various lace guides and internal lace guides, as described herein, creates this result in top lace 100 during movement of residual limb 38. The dramatic difference in the stretch of the skin surface on the posterior surface of the elbow at flexion as shown in FIGS. 3 and 4 is significant enough that the balancing effect of balancing lace 98 may be incomplete, resulting in the slight tension increase at full flexion. The tension decrease at flexion in top lace 100 may be configured to compensate for this, at the same time as the slight increase in tension in balancing lace 98 actually has a benefit in correcting the natural gapping that occurs in a rigid prosthetic arm socket distal to the olecranon. The combination of the tightening of balancing lace 98 with the flexibility in the elongate counters 46 and socket 44 allow the proximal end of lower textile socket 56 to conform to the shape of the flexed residual limb and maintain a close and secure fit.

Figure 33:
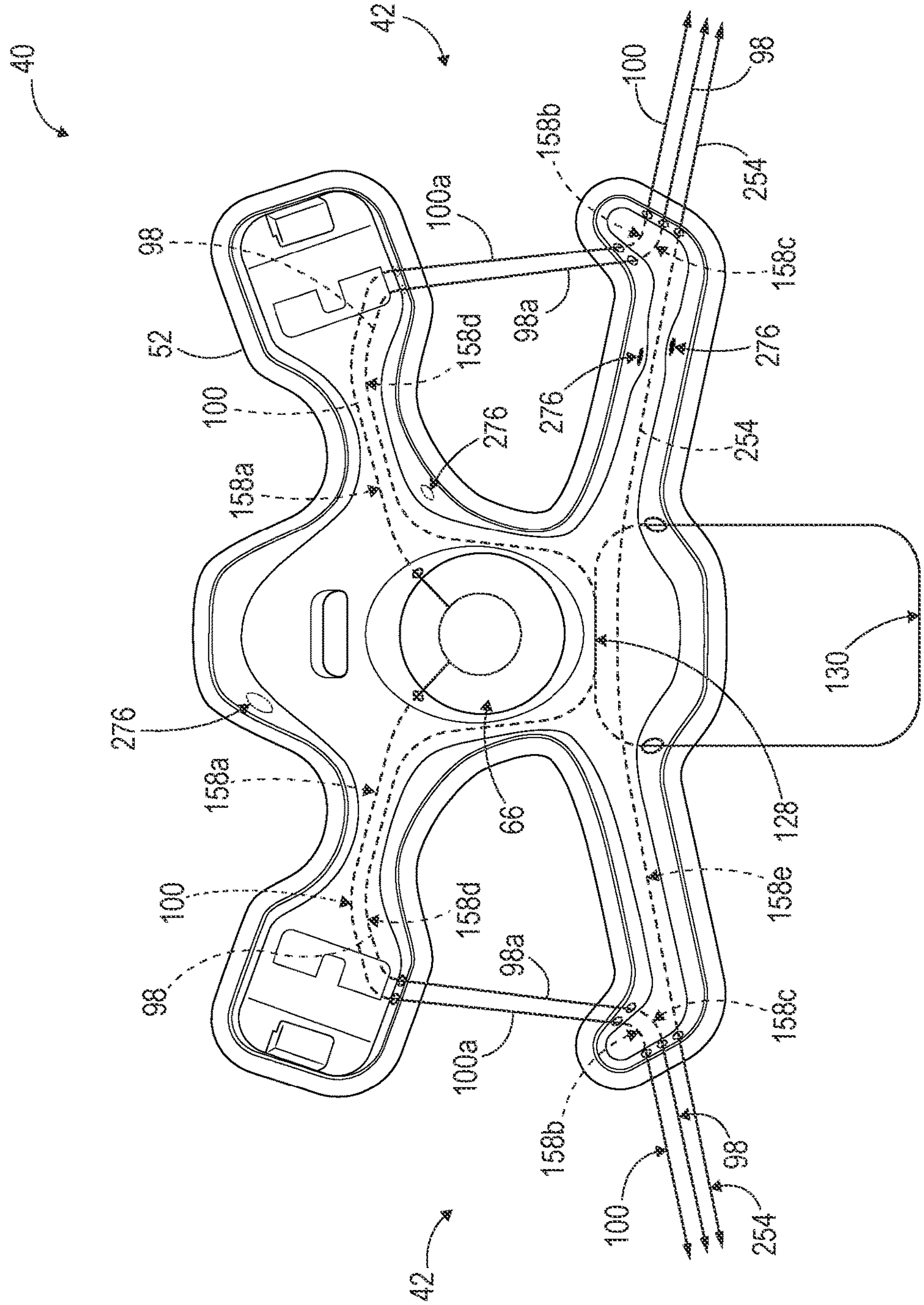
FIG. 33 is a flattened plan view of an example of an independent counter for use with disclosed prosthetic devices, illustrating routing of a portion of a selective adjustment system through the independent counter.

FIG. 33 illustrates an example of independent counter 52, shown flattened, with the routing of a portion of selective adjustment system 42, shown with respect to independent counter 52. Top lace 100 is shown leaving proximal tensioning reel 66 in two directions, heading both medially and laterally through internal lace guides 158*a* formed through each side of independent counter 52. Then a portion of top lace 100 (e.g., top lace 100*a*) exits internal lace guides 158*a* and travels externally to independent counter 52 to enter another internal lace guide on each side of independent counter 52 (internal lace guides 158*b*), and then continues to other components of prosthetic device 40. A portion of balancing lace 98 is shown traveling through internal lace guides 158*c* on each side of independent counter 52, then externally to independent counter 52 (at portion 98*a*), and then through internal lace guides 158*d* within each side of independent counter 52. The two portions of balancing lace 98 then cross under proximal tensioning reel 66 (indicated at 128), and then continue to looped path 130. FIG. 33 also shows a portion of extension fixed line 254, which extends across independent counter 52 through internal lace guide 158*e*. Independent counter 52 also may include ports 276 for an actuation cable or control cable to pass through independent counter 52 (e.g., through internal lace guides 158*f* and 158*g* shown in FIG. 16).

Figure 34:
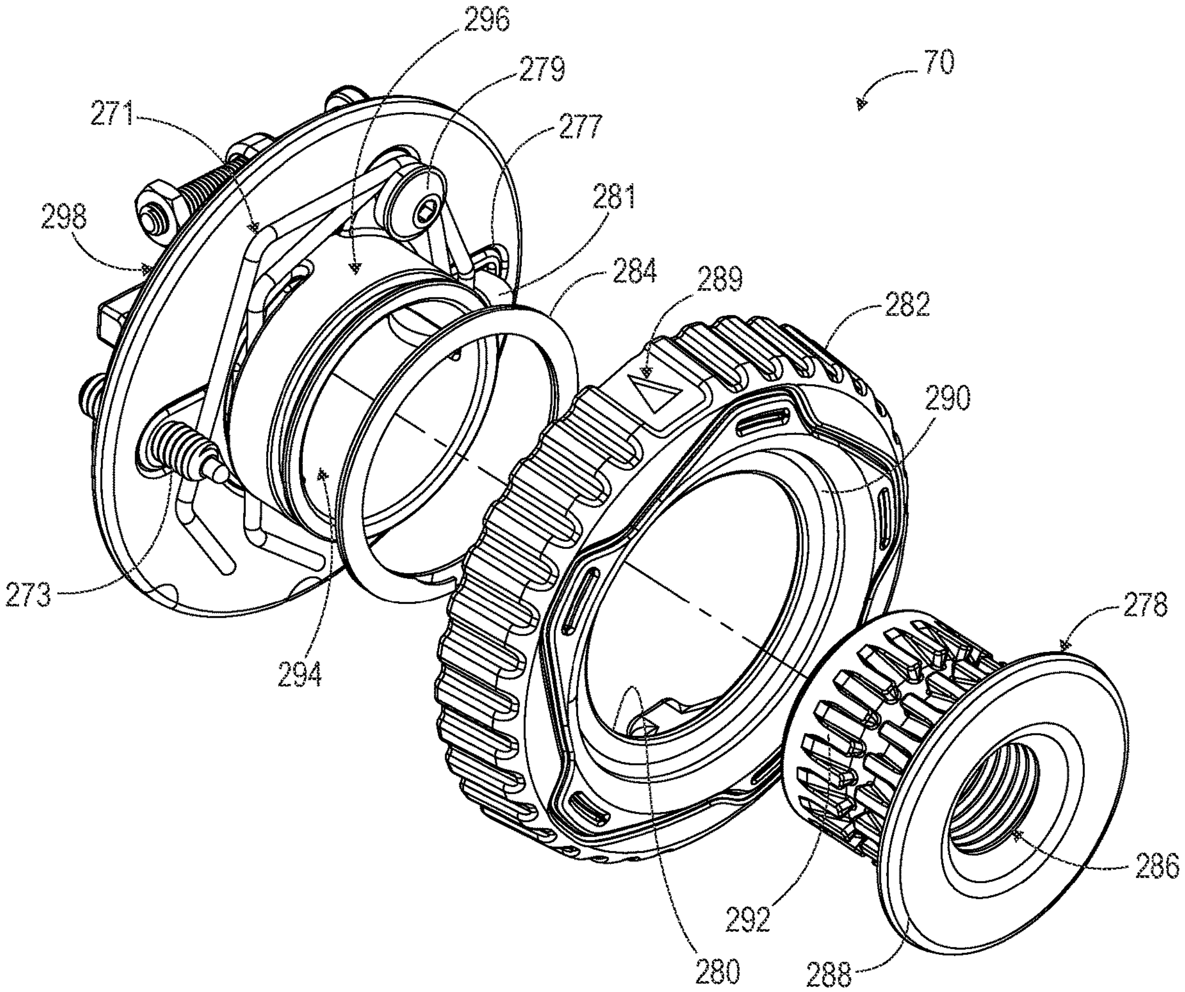
FIG. 34 is an exploded perspective view of an example of an end effector attachment unit for use with disclosed prosthetic devices.

FIGS. 34-37 illustrate an example of end effector attachment unit 70 that may be used with, included in, integrated into, and/or coupled to prosthetic devices 40. FIG. 34 illustrates the main components of end effector attachment unit 70, shown in an exploded view. A quick release adaptor 278 may be received through an aperture 280 of a rotating ring 282 and retained via a retaining ring 284. Quick release adaptor 278 may have a threaded bore 286 which may be configured to receive and engage with an end effector that the user may manipulate via prosthetic device 40. A flange 288 of quick release adaptor 278 may be configured to engage with or be seated against a recessed surface 290 of rotating ring 282. A cylindrical portion 292 of quick release adaptor 278 may extend through aperture 280 of rotating ring 282, and be received through a bore 294 of an attachment unit base 296. A custom washer 298 may be engaged with attachment unit base 296, and may be configured to reduce friction within end effector attachment unit 70. Washer 298 and an internal spring 271 may be configured to interact with quick release adaptor 278 to establish different positions and configurations for end effector attachment unit 70, such as the lock configuration, release configuration, and caster configuration discussed herein. Other configurations and functions also are within the scope of the present disclosure. Specifically, in the example mechanism illustrated in FIG. 34, as rotating ring 282 is rotated, internal spring 271 is moved aside (e.g., radially outward). A ball detent 273 of attachment unit base 296 may engage with rotating ring 282 to indicate when end effector attachment unit 70 is transitioned to a different configuration. In other words, a user may rotate rotating ring 282 until a click is heard or felt (from ball detent 273 engaging a feature of rotating ring 282), thus indicating that the configuration of end effector attachment unit 70 was changed. Additionally or alternatively, rotating ring 282 may include one or more visual markings 289 configured to visually indicate which configuration end effector attachment unit 70 is in.

Figure 35:
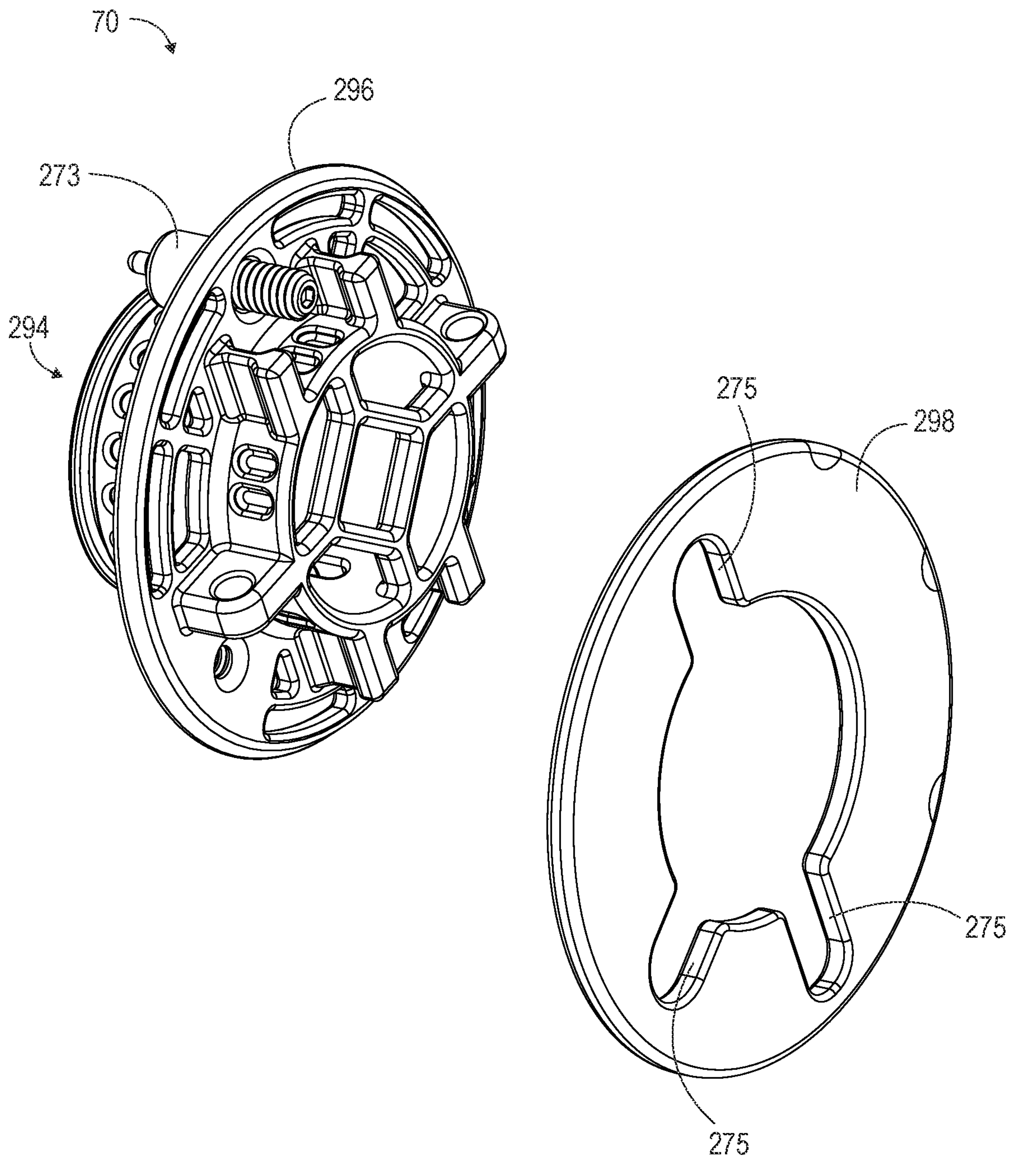
FIG. 35 is an exploded perspective view of a subassembly of the end effector attachment unit of FIG. 34.
Figure 36:
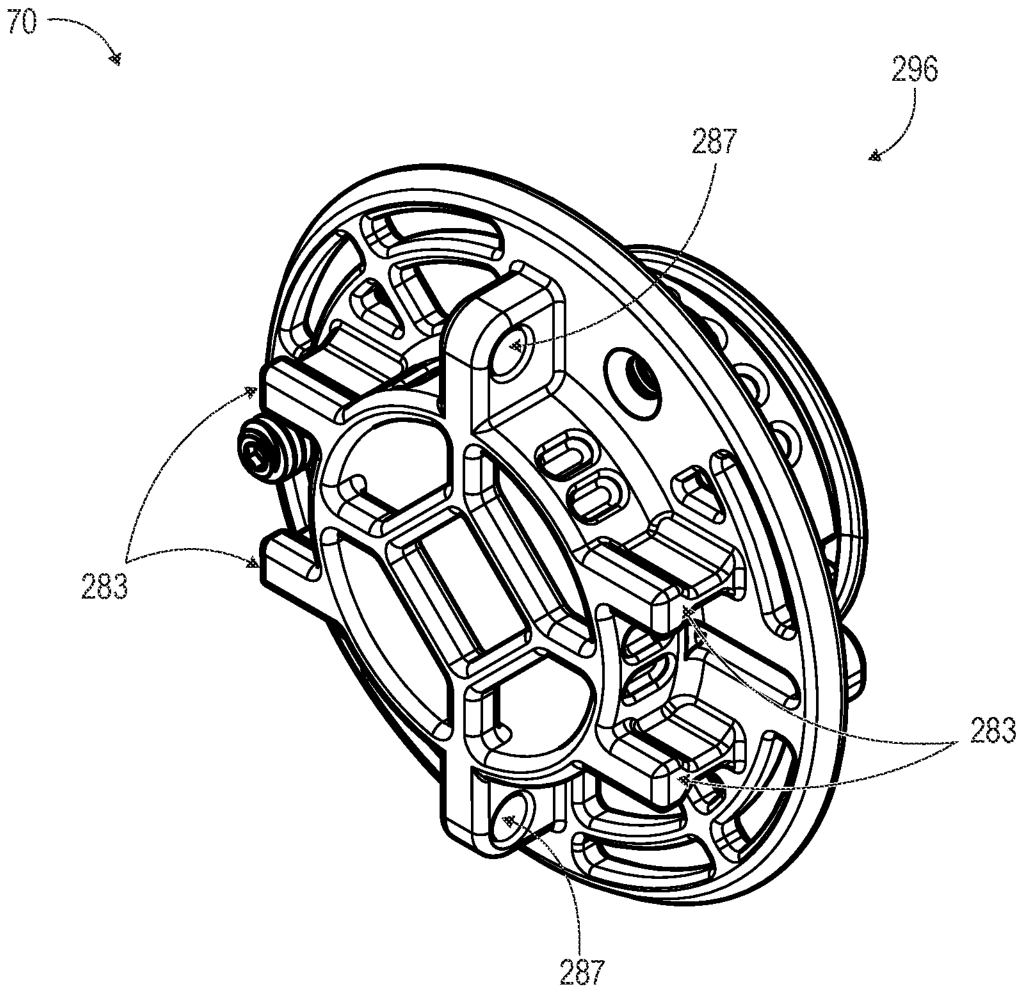
FIG. 36 is a perspective view of a component of the end effector attachment unit of FIG. 34, viewed from the back.

FIG. 35 shows an exploded view of the subassembly of washer 298 and attachment unit base 296. As best seen in FIG. 35, washer 298 may include a plurality of cutouts 275, through which features of attachment unit base 296 may be received. In this manner, washer 298 may be substantially prevented from rotating with respect to attachment unit base 296 due to engagement between cutouts 275 and features of attachment unit base 296, such as ball detent 273, a slot 277 for a caster lock washer 281 (see FIG. 34), and a spring attachment point 279. A rear side of attachment unit base 296 may be configured to be coupled to elongate counters 46, as best illustrated in FIG. 36. In a specific example, features on attachment unit base 296 create a mechanical connection to elongate counters 46 to secure end effector attachment unit 70 to chassis 48 of prosthetic device 40. For example, one or more male engagement features 283 may be configured to be inserted into a corresponding receptacle in elongate counters 46, and/or attachment unit base 296 may be secured to chassis 48 via one or more fasteners inserted through one or more fastener holes 287.

Figure 37:
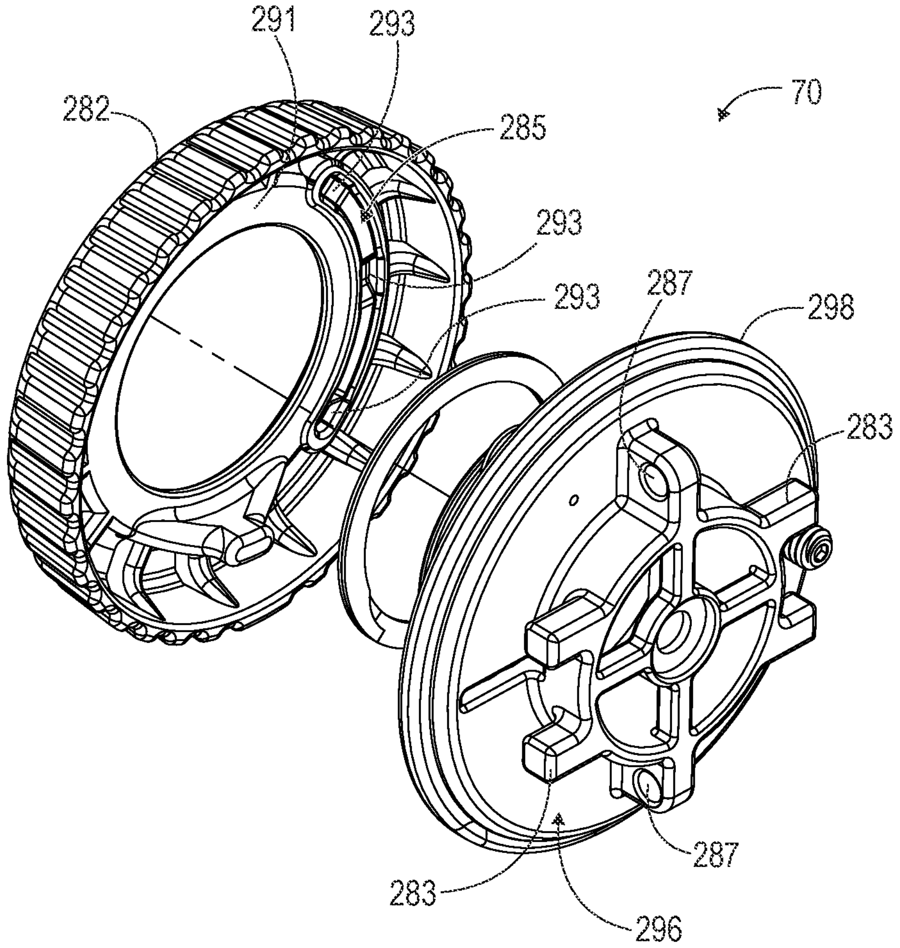
FIG. 37 is a partially exploded view of the end effector attachment unit of FIG. 34, viewed from the back.

FIG. 37 illustrates a partially exploded view of an example of end effector attachment unit 70, viewed from the back. A track 285 on inner surface 291 of rotating ring 282 may include a plurality of spaced apart recesses 293. For example, rotating ring 282 may include one respective recess 293 for each respective configuration of end effector attachment unit 70. While examples of end effector attachment units 70 have been described with three configurations herein, and thus may include three recesses 293, other examples of prosthetic devices 40 may include end effector attachment units 70 with more or fewer configurations, and thus more or fewer corresponding recesses 293. As rotating ring 282 is selectively rotated, ball detent 273 may extend into a respective recess 293 each time ball detent 273 reaches the respective recess 293. The position of rotating ring 282 is then maintained in that configuration until rotating ring 282 is selectively rotated again, and ball detent 273 may be engaged with a different respective recess 293 corresponding to a different configuration of end effector attachment unit 70. While the selective configuration changes are effectuated in this example via selective rotation of rotating ring 282, those of ordinary skill in the art will understand that other mechanisms and actuators for changing configurations of end effector attachment unit 70 also are within the scope of the present disclosure. In the exemplary but non-limiting configurations described herein, in the lock configuration, quick release adaptor 278 is substantially prevented from rotating with respect to rotating ring 282; in the caster configuration, quick release adaptor is free to rotate with respect to rotating ring 282; and in the release configuration, quick release adaptor 278 is released from rotating ring 282, such that any end effector coupled to quick release adaptor 278 may be selectively removed from end effector attachment unit 70.

Figure 38:
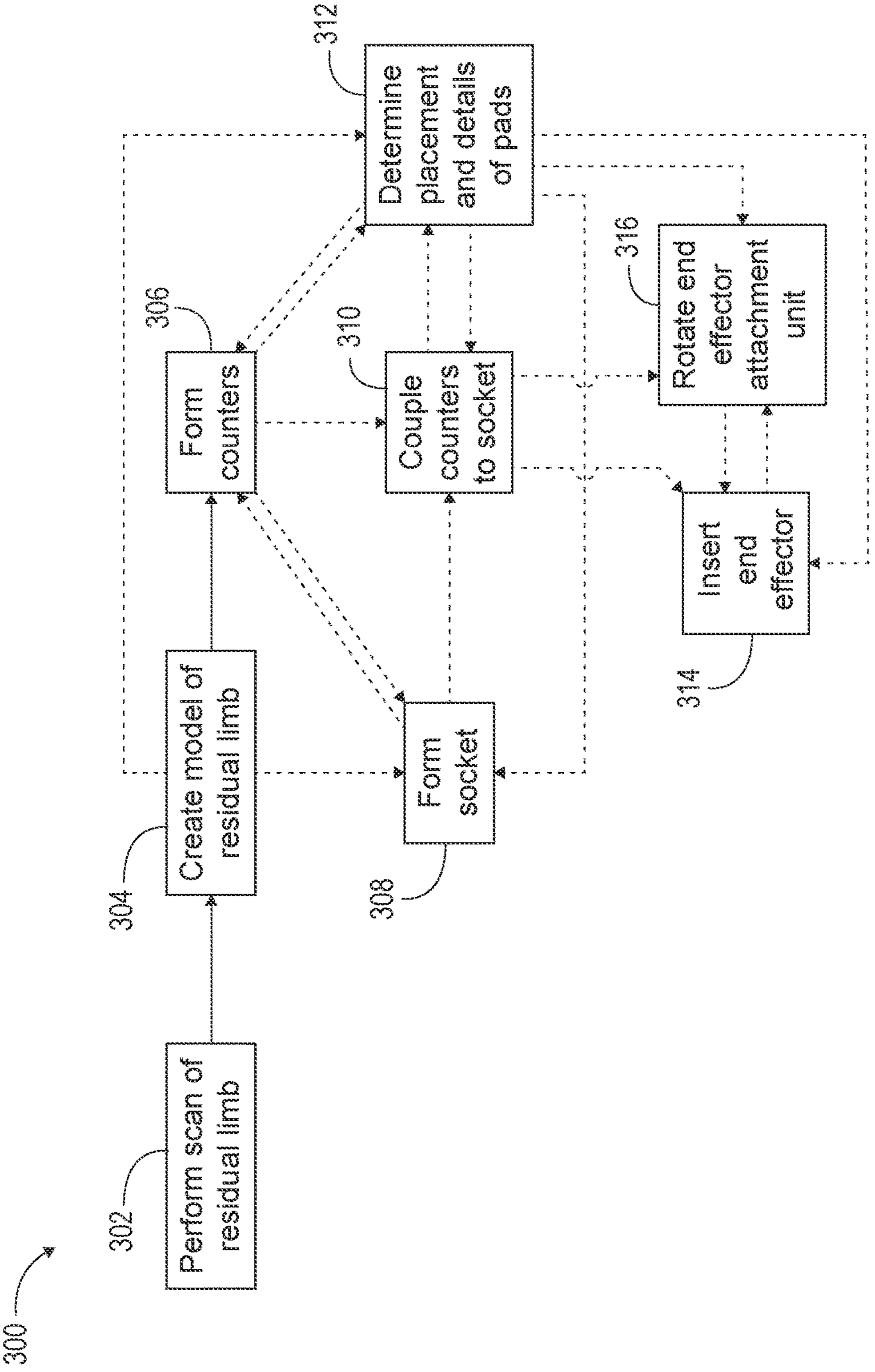
FIG. 38 is a schematic flowchart diagram of examples of methods of making prosthetic devices, according to the present disclosure.

FIG. 38 schematically provides a flowchart that represents illustrative, non-exclusive examples of methods 300 according to the present disclosure. In FIG. 38, some steps are illustrated in dashed boxes indicating that such steps may be optional or may correspond to an optional version of a method according to the present disclosure. That said, not all methods according to the present disclosure are required to include the steps illustrated in solid boxes. The methods and steps illustrated in FIG. 38 are not limiting, and other methods and steps are within the scope of the present disclosure, including methods having greater than or fewer than the number of steps illustrated, as understood from the discussions herein.

Methods 300 for making a prosthetic device (e.g., prosthetic device 40) for a given residual limb generally include performing a 3D-scan and/or measuring circumferences of the residual limb at 302, creating a computer-aided design (CAD) model of the given residual limb at 304, and forming a plurality of elongate counters (e.g., elongate counters 46) and an independent counter (e.g., independent counter 52) at 306 with the CAD model created at 304. Thus, the elongate counters and independent counter are custom-sized and shaped for the given patient's residual limb. In some examples, forming the elongate counters and the independent counter at 306 is performed by 3D-printing the elongate counters and the independent counter. Additionally or alternatively, forming the plurality of elongate counters at 306 may include building in an offset into a proximal portion of the plurality of elongate counters to account for a thickness of a lower textile socket of a socket of the prosthetic device. Additionally or alternatively, forming the plurality of elongate counters at 306 may include determining a respective contact length for each respective elongate counter of the plurality of elongate counters using the CAD model of the given residual limb.

Methods 300 also may include forming the socket (e.g., socket 44) at 308, which generally includes forming an upper socket (e.g., upper textile socket 58) and a lower socket (e.g., lower textile socket 56) and coupling the upper and lower sockets together. In examples, forming the socket at 308 includes shaping and preparing a plurality of textile pattern pieces to form the upper textile socket and the lower textile socket. Additionally or alternatively, the forming the socket at 308 may include sewing a mapped and flattened textile into a 3D-shape to create the lower textile socket and/or the upper textile socket. Again, the plurality of textile pattern pieces may be custom-sized and shaped for the given residual limb using the CAD model of the given residual limb.

Methods 300 also may include coupling the elongate counters to the socket (e.g., the lower textile socket), and coupling the independent counter to the socket (e.g., the upper textile socket) at 310. In coupling the elongate counters to the socket, methods 300 may, in the specific example of transradial amputations, include determining an arm length by determining a distance from a lateral epicondyle of the patient to an end effector attachment unit of the prosthetic device with a terminal device offset.

Methods 300 also may include determining a placement, a form, a density, and a scale of a plurality of interface pads (e.g., interface pads 64), such that the plurality of interface pads are configured to create effective and comfortable suspension for the given residual limb at 312. In some examples, one or more interface pads may be laminated between layers of the upper textile socket and/or between layers of the lower textile socket.

Once the prosthetic device is assembled, methods 300 may include placing an end effector (e.g., a terminal device, a leg end effector, a leg pylon, and/or a prosthetic foot) partially within the end effector attachment unit of the prosthetic device at 314, thereby securing the end effector to a chassis of the prosthetic device such that the patient may manipulate the end effector using the prosthetic device. The end effector attachment unit may be rotated at 316 to transition the end effector attachment unit between configurations, such that the end effector may be locked in placed, removed, and/or freely rotatable in a caster configuration. In this manner, as desired, the end effector may be removed from the prosthetic device by placing the end effector attachment unit in a release configuration, and then replaced with the same or different end effector.

Illustrative, non-exclusive examples of inventive subject matter according to the present disclosure are described in the following enumerated paragraphs:

A1. A prosthetic device for engaging a residual limb, the prosthetic device comprising:

a plurality of elongate counters extending proximally from a chassis and configured to receive at least a portion of the residual limb within a volume defined by the plurality of elongate counters, wherein each respective elongate counter of the plurality of elongate counters is configured to counteract forces applied to the residual limb via the prosthetic device;

a socket configured to engage with the residual limb; and a selective adjustment system configured to secure the prosthetic device to the residual limb and configured to provide selective adjustment of compression of the socket around the residual limb.

A1.1. The prosthetic device of paragraph A1, wherein the socket comprises:

a lower textile socket coupled to the plurality of elongate counters; and an upper textile socket coupled to the lower textile socket.

A1.2. The prosthetic device of paragraph A1 or A1.1, wherein the selective adjustment system is configured to couple the plurality of elongate counters and the socket such that the prosthetic device is configured to bear a required load.

A1.3. The prosthetic device of any of paragraphs A1-A1.2, wherein the selective adjustment system is a selective adjustment and suspension system.

A1.4. The prosthetic device of any of paragraphs A1-A1.3, wherein the selective adjustment system comprises at least one fixed line having a predetermined length, and at least one lace having a selectively adjustable length.

A2. The prosthetic device of any of paragraphs A1-A1.4, wherein the prosthetic device is configured to create a dynamic volume within the socket, such that the dynamic volume is configured to account for and accommodate changes in shape of the residual limb through a range of motion of the residual limb.

A3. The prosthetic device of paragraph A2, wherein the selective adjustment system is configured to create the dynamic volume.

A4. The prosthetic device of any of paragraphs A2-A3, wherein the plurality of elongate counters, the socket, and the selective adjustment system interact together to create the dynamic volume of the socket.

A5. The prosthetic device of any of paragraphs A2-A4, wherein the prosthetic device is configured to preserve the range of motion of the residual limb via the dynamic volume of the socket.

A6. The prosthetic device of any of paragraphs A1-A5, wherein the selective adjustment system is configured to selectively adjust suspension of the residual limb via the prosthetic device.

A7. The prosthetic device of any of paragraphs A1-A6, wherein the prosthetic device is configured to avoid predetermined portions of the residual limb so as to preserve a/the range of motion the residual limb.

A8. The prosthetic device of any of paragraphs A1-A7, wherein the socket is configured to tighten around the residual limb if forces applied to a distal end region of the chassis cause the socket to be pulled away from the residual limb.

A9. The prosthetic device of any of paragraphs A1-A8, wherein the socket is breathable.

A10. The prosthetic device of any of paragraphs A1-A9, wherein the socket is moisture-wicking.

A11. The prosthetic device of any of paragraphs A1-A10, wherein the plurality of elongate counters are configured to directly translate motion of the residual limb to a/the distal end region of the chassis.

A12. The prosthetic device of any of paragraphs A1-A11, wherein a combination of the plurality of elongate counters, the socket, and the selective adjustment system is configured to translate motion from the residual limb to a/the distal end region of the chassis.

A13. The prosthetic device of any of paragraphs A1-A12, wherein the plurality of elongate counters are configured to apply compression to one or more interface pads of the prosthetic device.

A14. The prosthetic device of any of paragraphs A1-A13, wherein the plurality of elongate counters are configured to bridge between the residual limb and a/the distal end region of the chassis.

A15. The prosthetic device of any of paragraphs A1-A14, wherein a/the distal end region of the chassis is standardized.

A16. The prosthetic device of any of paragraphs A1-A15, wherein a/the distal end region of the chassis is configured as a wrist unit.

A17. The prosthetic device of any of paragraphs A1-A16, wherein the plurality of elongate counters are configured to be 3D-printed.

A18. The prosthetic device of any of paragraphs A1-A17, wherein the plurality of elongate counters are configured to be customized for individual patients.

A19. The prosthetic device of any of paragraphs A1-A18, wherein a contact length of each respective elongate counter is patient-specific.

A20. The prosthetic device of any of paragraphs A1-A19, wherein the plurality of elongate counters comprise nylon and/or thermoplastic polyurethane.

A21. The prosthetic device of any of paragraphs A1-A20, wherein the plurality of elongate counters are coupled to an outer surface of a/the lower textile socket of the socket.

A21.1. The prosthetic device of any of paragraphs A1-A21, wherein the plurality of elongate counters are coupled to a middle layer of a/the lower textile socket of the socket.

A22. The prosthetic device of any of paragraphs A1-A21.1, wherein the plurality of elongate counters comprise a plurality of forearm counters that are configured to be positioned surrounding a residual forearm of a patient.

A23. The prosthetic device of paragraph A22, wherein the plurality of forearm counters are configured to terminate distal to a cubital fold region of the patient when the prosthetic device is donned.

A24. The prosthetic device of any of paragraphs A1-A23, wherein the plurality of elongate counters are integrally formed with the chassis.

A25. The prosthetic device of any of paragraphs A1-A23, wherein the plurality of elongate counters are coupled to the chassis.

A26. The prosthetic device of any of paragraphs A1-A25, wherein a lateral portion of the plurality of elongate counters is configured to support an anterior side of the residual limb and a posterior side of the residual limb.

A27. The prosthetic device of paragraph A26, wherein the lateral portion of the plurality of elongate counters comprises a lateral-anterior elongate counter and a lateral-posterior elongate counter.

A28. The prosthetic device of any of paragraphs A1-A27, wherein a medial portion of the plurality of elongate counters is configured to support an/the anterior side of the residual limb and a/the posterior side of the residual limb.

A29. The prosthetic device of paragraph A28, wherein the medial portion of the plurality of elongate counters comprises a medial-anterior elongate counter and a medial-posterior elongate counter.

A30. The prosthetic device of any of paragraphs A1-A29, wherein the plurality of elongate counters are configured to maintain consistent attachment of the socket on the residual limb.

A31. The prosthetic device of any of paragraphs A1-A30, wherein the plurality of elongate counters are shaped and sized such that the plurality of elongate counters are configured to avoid impeding a range of motion of the residual limb, while maintaining sufficient force to counter a load on a terminal device or an end effector coupled to the chassis.

A32. The prosthetic device of any of paragraphs A1-A31, wherein the plurality of elongate counters are configured to avoid applying pressure to pressure-intolerant areas of the residual limb.

A33. The prosthetic device of any of paragraphs A1-A32, wherein the plurality of elongate counters comprise a keyed-rail system and fixing hardware, and wherein a/the lower textile socket of the socket is coupled to each respective elongate counter of the plurality of elongate counters via the keyed-rail system.

A34. The prosthetic device of paragraph A33, wherein the keyed-rail system comprises a recessed track formed in an inner counter surface of each respective elongate counter of the plurality of elongate counters.

A35. The prosthetic device of any of paragraphs A33-A34, wherein the keyed-rail system comprises a plurality of rails protruding from the lower textile socket, wherein each respective rail of the plurality of rails is configured to slide into a respective recessed track of a respective elongate counter.

A36. The prosthetic device of any of paragraphs A33-A35, wherein the keyed-rail system comprises a plurality of cavities, with each respective cavity of the plurality of cavities being formed in a respective elongate counter of the plurality of elongate counters, wherein the keyed-rail system further comprises a plurality of projections, with each respective projection of the plurality of projections extending from the lower textile socket distal to a respective rail of the plurality of rails, and wherein each respective projection is configured to be at least partially inserted within a respective cavity when the plurality of elongate counters are coupled to the lower textile socket.

A37. The prosthetic device of any of paragraphs A33-A36, wherein the keyed-rail system comprises a respective threaded bore extending through each respective cavity and each respective projection, such that the keyed-rail system is configured to receive a respective fastener through each respective cavity and each respective projection to further secure the plurality of elongate counters to the lower textile socket.

A38. The prosthetic device of any of paragraphs A1-A37, further comprising an independent counter that is positioned proximal to the plurality of elongate counters.

A38.1. The prosthetic device of paragraph A38, comprising a plurality of independent counters.

A39. The prosthetic device of paragraph A38 or A38.1, wherein the independent counter comprises a proximal tensioning reel configured to adjust a tension of one or more laces, lines, cables, wires, and/or fibers of the selective adjustment system.

A40. The prosthetic device of paragraph A39, wherein the proximal tensioning reel is configured to adjust a tension of a top lace of the selective adjustment system.

A41. The prosthetic device of paragraph A40, wherein the proximal tensioning reel is configured to selectively tighten or release the top lace, and wherein the top lace is continuous from the proximal tensioning reel to a distal end of a/the lower textile socket of the socket.

A42. The prosthetic device of any of paragraphs A38-A41, wherein the independent counter is configured to be 3D-printed.

A43. The prosthetic device of any of paragraphs A38-A42, wherein the independent counter is configured to be patient-specific.

A44. The prosthetic device of any of paragraphs A38-A43, wherein the independent counter is configured to apply a compressive force on a/the one or more interface pads of the prosthetic device.

A45. The prosthetic device of any of paragraphs A38-A44, wherein the independent counter is configured to be coupled to a harness worn by the patient.

A46. The prosthetic device of any of paragraphs A38-A45, wherein the independent counter comprises a magnetic attachment point configured for selective coupling to a/the harness worn by the patient.

A47. The prosthetic device of any of paragraphs A38-A46, wherein the independent counter comprises a counter pull loop or tab configured to facilitate positioning of the prosthetic device on the residual limb.

A47.1. The prosthetic device of paragraph A47, wherein the counter pull loop or tab is a posterior counter pull loop or tab configured to be positioned on a/the posterior side of the residual limb.

A47.2. The prosthetic device of paragraph A47 or A47.1, wherein the counter pull loop or tab is configured to be positioned on a/the medial side of the residual limb and/or on a/the lateral side of the residual limb.

A48. The prosthetic device of any of paragraphs A38-A47.2, wherein the independent counter is directly coupled to an/the upper textile socket of the socket.

A49. The prosthetic device of any of paragraphs A38-A48, wherein the independent counter comprises one or more internal lace guides extending through a thickness of the independent counter, and wherein one or more laces of the selective adjustment system are configured to pass through the independent counter via the one or more internal lace guides.

A50. The prosthetic device of any of paragraphs A38-A49, wherein the independent counter is an elbow counter.

A51. The prosthetic device of paragraph A50, wherein the elbow counter is configured to be positioned proximal to an elbow of the residual limb when the prosthetic device is donned.

A52. The prosthetic device of any of paragraphs A50-A51, wherein the elbow counter is configured to be positioned posterior to an ulna of the residual limb when the prosthetic device is donned.

A53. The prosthetic device of any of paragraphs A50-A52, wherein the elbow counter is configured to resist movement of the elbow of the residual limb away from a/the distal end region of the chassis.

A54. The prosthetic device of any of paragraphs A50-A53, wherein the elbow counter comprises one or more supracondylar counter interface pads.

A55. The prosthetic device of any of paragraphs A38-A49, wherein the independent counter is a knee counter.

A56. The prosthetic device of paragraph A55, wherein the knee counter comprises one or more interface pads configured to engage medial epicondyles and lateral epicondyles of a femur of the residual limb.

A57. The prosthetic device of paragraph A55 or A56, wherein the knee counter is configured to be positioned proximal to a knee of the residual limb when the prosthetic device is donned.

A58. The prosthetic device of any of paragraphs A1-A57, wherein a/the lower textile socket of the socket comprises one or more interface pads configured to provide cushioning for one or more bony prominences of the residual limb.

A59. The prosthetic device of any of paragraphs A1-A58, wherein a/the lower textile socket of the socket comprises one or more forearm interface pads.

A60. The prosthetic device of any of paragraphs A1-A59, wherein a/the lower textile socket of the socket comprises a/the one or more interface pads configured to provide cushioning and engage with a patella of a/the patient and distal tips of a tibia and a fibula of a/the patient to support weight bearing.

A61. The prosthetic device of any of paragraphs A1-A60, wherein a/the lower textile socket of the socket is custom-patterned and fabricated for a residual limb of each respective patient.

A62. The prosthetic device of any of paragraphs A1-A61, wherein a/the lower textile socket of the socket comprises an outer layer.

A63. The prosthetic device of paragraph A62, wherein the outer layer of the lower textile socket comprises a plurality of lace guides for receiving one or more laces, lines, cables, wires, and/or fibers of the selective adjustment system therethrough.

A64. The prosthetic device of paragraph A62-A63, wherein the outer layer of the lower textile socket comprises at least one reinforcing overlay.

A65. The prosthetic device of any of paragraphs A62-A64, wherein the outer layer of the lower textile socket comprises an abrasion-resistant material and/or a stretch-woven material.

A66. The prosthetic device of any of paragraphs A1-A65, wherein a/the lower textile socket of the socket comprises a/the middle layer.

A67. The prosthetic device of paragraph A66, wherein the middle layer of the lower textile socket is configured to constrain the socket.

A68. The prosthetic device of paragraph A66 or A67, wherein the middle layer of the lower textile socket comprises a plurality of spaced-apart reinforcement strips configured to reinforce the lower textile socket.

A69. The prosthetic device of any of paragraphs A66-A68, wherein the middle layer of the lower textile socket comprises one or more elastic straps positioned and configured to provide localized areas of extra stretch, extra compression, and/or resistance to sag in the lower textile socket.

A70. The prosthetic device of any of paragraphs A66-A69, wherein the middle layer of the lower textile socket comprises one or more non-woven overlays positioned to at least partially overlay areas of overlap between one or more reinforcement strips of a/the plurality of spaced-apart reinforcement strips and a/the one or more elastic straps.

A71. The prosthetic device of any of paragraphs A1-A70, wherein a/the lower textile socket of the socket comprises an inner liner comprising a first liner layer and a second liner layer.

A72. The prosthetic device of paragraph A71, wherein the first liner layer and the second liner layer are laminated and stitched together.

A73. The prosthetic device of paragraph A71 or A72, wherein at least one interface pad of a/the one or more interface pads is positioned between the first liner layer and the second liner layer.

A74. The prosthetic device of any of paragraphs A1-A73, wherein a/the lower textile socket of the socket comprises a distal cup positioned between an/the inner liner and a/the middle layer and is configured to provide cushioning for the residual limb.

A75. The prosthetic device of any of paragraphs A1-A74, wherein an/the upper textile socket of the socket comprises one or more interface pads configured to be positioned to cushion a/the one or more bony prominences of the residual limb.

A76. The prosthetic device of any of paragraphs A1-A75, wherein an/the upper textile socket of the socket comprises one or more elbow interface pads.

A77. The prosthetic device of any of paragraphs A1-A75, wherein an/the upper textile socket of the socket comprises one or more knee interface pads.

A78. The prosthetic device of any of paragraphs A1-A77, wherein an/the upper textile socket of the socket is positioned at least partially within a/the lower textile socket of the socket.

A79. The prosthetic device of any of paragraphs A1-A78, wherein an/the upper textile socket of the socket is coupled to an inner socket surface of a/the lower textile socket.

A80. The prosthetic device of any of paragraphs A1-A79, wherein an/the upper textile socket of the socket is configured to accommodate expansion of tissue of a/the cubital fold region of a/the patient.

A81. The prosthetic device of any of paragraphs A1-A80, wherein an/the upper textile socket of the socket comprises four-way stretch material.

A82. The prosthetic device of any of paragraphs A1-A81, wherein an/the upper textile socket of the socket comprises a cutout to receive a/the joint of the residual limb.

A83. The prosthetic device of any of paragraphs A1-A82, wherein an/the upper textile socket of the socket comprises an upper socket liner configured to engage with the residual limb.

A84. The prosthetic device of paragraph A83, wherein the upper socket liner comprises one or more interface pads.

A85. The prosthetic device of paragraph A83 or A84, wherein the upper socket liner comprises a medial epicondyle interface pad.

A86. The prosthetic device of any of paragraphs A83-A85, wherein the upper socket liner comprises polyspan fabric.

A87. The prosthetic device of any of paragraphs A1-A86, wherein an/the upper textile socket of the socket comprises an upper socket middle layer.

A88. The prosthetic device of paragraph A87, wherein the upper socket middle layer comprises a 4D-spacer mesh material.

A89. The prosthetic device of any of paragraphs A87-A88, wherein a flexion fixed line of the prosthetic device is coupled to the upper socket middle layer, with the flexion fixed line extending distally from the upper textile socket.

A90. The prosthetic device of any of paragraphs A87-A89, wherein the upper socket middle layer comprises an elastic strap extending circumferentially around a proximal opening of the upper socket middle layer, wherein the proximal opening is configured to receive the residual limb therethrough, and wherein the elastic strap is configured to help secure the upper textile socket around the residual limb and avoid sag.

A91. The prosthetic device of any of paragraphs A1-A90, wherein an/the upper textile socket of the socket comprises an upper socket outer layer, wherein an/the upper socket middle layer is sandwiched between the upper socket outer layer and an/the upper socket liner.

A92. The prosthetic device of paragraph A91, wherein the upper socket outer layer is configured to engage with a/the independent counter of the prosthetic device.

A93. The prosthetic device of any of paragraphs A91-A92, wherein the upper socket outer layer comprises a socket pull loop or tab on an anterior side of the upper socket outer layer configured to aid in donning the prosthetic device, wherein the socket pull loop or tab is configured to be positioned on an/the anterior side of the residual limb when the prosthetic device is donned.

A94. The prosthetic device of any of paragraphs A91-A93, wherein the upper socket outer layer comprises a back panel comprising:

an olecranon fossa support pad;

a/the proximal tensioning reel; and a/the posterior socket pull loop.

A95. The prosthetic device of any of paragraphs A1-A94, wherein the socket comprises a plurality of layers that integrate with each other and with the plurality of elongate counters such that the socket is configured to reinforce a connection between the residual limb and a/the terminal device or a/the end effector coupled to the chassis.

A96. The prosthetic device of any of paragraphs A1-A95, wherein the socket comprises at least a first region comprising a stretch textile.

A97. The prosthetic device of any of paragraphs A1-A96, wherein the socket comprises at least a second region comprising a non-stretch textile.

A98. The prosthetic device of any of paragraphs A1-A97, wherein the prosthetic device comprises a/the plurality of interface pads configured to interface with underlying bone structures and/or bony prominences of the residual limb.

A99. The prosthetic device of paragraph A98, wherein the plurality of interface pads are compression molded.

A100. The prosthetic device of paragraph A98 or A99, Wherein the plurality of interface pads are contoured.

A101. The prosthetic device of any of paragraphs A98-A100, wherein the plurality of interface pads are positioned within the socket and configured to be positioned between the plurality of elongate counters and the residual limb.

A102. The prosthetic device of any of paragraphs A98-A101, wherein at least one of the interface pads of the plurality of interface pads is laminated within an/the upper textile socket of the socket.

A103. The prosthetic device of any of paragraphs A98-A102, wherein an/the upper textile socket of the socket comprises a/the one or more elbow interface pads of the plurality of interface pads.

A104. The prosthetic device of paragraph A103, wherein the one or more elbow interface pads are configured to be positioned to support a humerus of the residual limb.

A105. The prosthetic device of paragraph A103 or A104, wherein the one or more elbow interface pads comprises a lateral elbow pad, a medial elbow pad, and a posterior elbow pad.

A106. The prosthetic device of any of paragraphs A98-A105, wherein at least one interface pad of the plurality of interface pads is laminated within a/the lower textile socket of the socket.

A107. The prosthetic device of any of paragraphs A98-A106, wherein a/the lower textile socket of the socket comprises one or more forearm interface pads of the plurality of interface pads.

A108. The prosthetic device of paragraph A107, wherein the one or more forearm interface pads are configured to be positioned to support a radius of the residual limb and an/the ulna of the residual limb.

A109. The prosthetic device of paragraph A107 or A108, wherein the one or more forearm interface pads comprises an anterior forearm pad and a posterior forearm pad.

A110. The prosthetic device of any of paragraphs A107-A109, wherein the one or more forearm interface pads comprise an elongate portion configured to be positioned to extend substantially parallel to a/the radius of the residual limb and an/the ulna of the residual limb.

A111. The prosthetic device of any of paragraphs A107-A110, wherein the one or more forearm interface pads are configured to center the prosthetic device on the residual limb relative to a central axis via the elongate portion.

A112. The prosthetic device of any of paragraphs A107-A111, wherein the one or more forearm interface pads comprise a curved portion configured to be positioned such that the curved portion extends substantially perpendicularly to a/the radius of the residual limb and/or an/the ulna of the residual limb.

A113. The prosthetic device of any of paragraphs A107-A112, wherein the one or more forearm interface pads are configured to restrict ends of a/the radius of the residual limb and/or an/the ulna of the residual limb when the chassis is under load via a/the curved portion of the one or more forearm interface pads.

A114. The prosthetic device of any of paragraphs A98-A113, wherein the plurality of interface pads comprise a thermoplastic polyurethane (TPU), an ethylene-vinyl acetate (EVA) foam, neoprene, polyester, latex foam, a mineral or silicone gel, wool, cotton, cotton felt, leather, nylon, and/or polylactic acid (PLA).

A115. The prosthetic device of any of paragraphs A98-A114, wherein the plurality of interface pads are configured to improve suspension of the residual limb while maintaining a/the range of motion of the residual limb.

A116. The prosthetic device of any of paragraphs A98-A115, wherein the plurality of interface pads comprises a first pad, wherein when the prosthetic device is worn, the first pad is configured to be positioned to support a medial epicondyle of the residual limb.

A117. The prosthetic device of any of paragraphs A98-A116, wherein the plurality of interface pads comprises a second pad, wherein when the prosthetic device is worn, the second pad is configured to be positioned to support a lateral epicondyle of the residual limb.

A118. The prosthetic device of any of paragraphs A98-A117, wherein the plurality of interface pads comprises an olecranon fossa pad, wherein when the prosthetic device is worn, the olecranon fossa pad is configured to transfer forces between an/the elbow counter and a/the humerus of the residual limb.

A119. The prosthetic device of any of paragraphs A1-A118, wherein the chassis comprises an end effector attachment unit configured to receive a/the terminal device, an/the end effector, a leg end effector, a leg pylon, and/or a prosthetic foot.

A120. The prosthetic device of paragraph A119, wherein the end effector attachment unit is positioned within a/the distal end region of the chassis, such that the chassis is configured to operatively and removably couple the terminal device, the end effector, the leg end effector, the leg pylon, and/or the prosthetic foot to the residual limb.

A121. The prosthetic device of paragraph A119 or A120, wherein the end effector attachment unit is selectively adjustable between a lock configuration, a caster configuration, and a release configuration.

A122. The prosthetic device of paragraph A121, wherein in the lock configuration, the end effector attachment unit is configured to secure the terminal device, the end effector, the leg end effector, the leg pylon, and/or the prosthetic foot with respect to the chassis such that the terminal device, the end effector, the leg end effector, the leg pylon, and/or the prosthetic foot has a fixed position and orientation with respect to the chassis.

A123. The prosthetic device of paragraph A121 or A122, wherein in the caster configuration, the end effector attachment unit is configured to secure the terminal device, the end effector, the leg end effector, the leg pylon, and/or the prosthetic foot with respect to the chassis such that the terminal device, the end effector, the leg end effector, the leg pylon, and/or the prosthetic foot is free to rotate with respect to the chassis.

A124. The prosthetic device of any of paragraphs A121-A123, wherein in the release configuration, the end effector attachment unit is configured to release the terminal device, the end effector, the leg end effector, the leg pylon, and/or the prosthetic foot such that the terminal device, the end effector, the leg end effector, the leg pylon, and/or the prosthetic foot may be selectively removed from the chassis.

A125. The prosthetic device of any of paragraphs A121-A124, wherein the end effector attachment unit is configured to be selectively transitioned to the lock configuration, the caster configuration, or the release configuration by rotating the end effector attachment unit relative to the plurality of elongate counters.

A126. The prosthetic device of any of paragraphs A1-A125, wherein the selective adjustment system is configured to provide selective adjustment of compression of the plurality of elongate counters around the residual limb.

A127. The prosthetic device of any of paragraphs A1-A126, wherein the selective adjustment system is configured to provide selective adjustment of compression of a/the lower textile socket of the socket and an/the upper textile socket of the socket independently from one another around the residual limb.

A128. The prosthetic device of any of paragraphs A1-A127, wherein the selective adjustment system is coupled to the socket such that the prosthetic device is configured to preserve a/the range of motion of the residual limb.

A129. The prosthetic device of any of paragraphs A1-A128, wherein the selective adjustment system comprises any of five pairs of flexible hinges that connect an/the upper textile socket of the socket and a/the lower textile socket of the socket and maintain a snug fit to the residual limb through a/the range of motion of the residual limb.

A130. The prosthetic device of any of paragraphs A1-A129, wherein the selective adjustment system is configured to function as one or more flexible hinges.

A131. The prosthetic device of any of paragraphs A1-A130, wherein the selective adjustment system comprises lacing and/or a plurality of wires, fibers, laces, and/or cables that pass over and/or across a/the joint of the residual limb.

A132. The prosthetic device of any of paragraphs A1-A131, wherein the selective adjustment system comprises a plurality of wires, fibers, laces, and/or cables that are integrated into the socket.

A133. The prosthetic device of any of paragraphs A1-A132, wherein the selective adjustment system comprises a balancing lace.

A134. The prosthetic device of paragraph A133, wherein the balancing lace extends through an/the internal lace guide of a/the independent counter.

A135. The prosthetic device of paragraph A133 or A134, wherein the balancing lace comprises four crossings of a/the joint of the residual limb.

A136. The prosthetic device of any of paragraphs A133-A135, wherein the chassis comprises a distal tensioning reel configured to adjust tension in the balancing lace.

A137. The prosthetic device of any of paragraphs A133-A136, wherein the balancing lace extends proximally from a/the distal tensioning reel along a medial side of the socket and along a lateral side of the socket.

A138. The prosthetic device of any of paragraphs A133-A137, wherein the balancing lace extends proximally from a/the distal tensioning reel to a/the independent counter of the prosthetic device.

A139. The prosthetic device of any of paragraphs A133-A138, wherein the balancing lace travels internally through a/the one or more internal lace guides of a/the independent counter of the prosthetic device to a posterior side of the socket.

A140. The prosthetic device of any of paragraphs A133-A139, wherein a medial portion of the balancing lace crosses over a lateral portion of the balancing lace on a/the posterior side of the socket.

A141. The prosthetic device of any of paragraphs A133-A140, wherein the balancing lace is configured to pull a/the independent counter of the prosthetic device towards the plurality of elongate counters and draw the residual limb into the socket.

A142. The prosthetic device of any of paragraphs A1-A141, wherein the selective adjustment system comprises a/the top lace.

A143. The prosthetic device of paragraph A142, wherein the top lace extends through an/the internal lace guide of a/the independent counter.

A144. The prosthetic device of any of paragraphs A142-A143, wherein the top lace extends distally from a/the proximal tensioning reel of a/the independent counter.

A145. The prosthetic device of any of paragraphs A142-A144, wherein the top lace comprises two crossings of a/the joint of the residual limb.

A146. The prosthetic device of any of paragraphs A142-A145, wherein the top lace extends from a/the posterior side of the socket to an anterior side of the socket.

A147. The prosthetic device of any of paragraphs A142-A146, wherein a medial portion of the top lace crosses a lateral portion of the top lace on an/the anterior side of the socket.

A148. The prosthetic device of any of paragraphs A142-A147, wherein a/the medial portion of the top lace crosses a/the lateral portion of the top lace a plurality of times on an/the anterior side of the socket, thereby forming a plurality of crossings of the top lace.

A149. The prosthetic device of paragraph A148, wherein a most proximal crossing of the top lace is configured to be positioned distal to a bicep tendon and cubital fold of the residual limb.

A150. The prosthetic device of any of paragraphs A142-A149, wherein the top lace is configured such that extension of the residual limb tensions the top lace.

A151. The prosthetic device of any of paragraphs A142-A150, wherein the top lace engages with a/the independent counter and the plurality of elongate counters such that when the top lace is tightened, the top lace pulls together a subset of the plurality of elongate counters positioned on an/the anterior side of the prosthetic device.

A152. The prosthetic device of any of paragraphs A1-A151, wherein the selective adjustment system comprises an extension fixed line.

A153. The prosthetic device of paragraph A152, wherein a/the independent counter comprises an/the internal lace guide through which the extension fixed line extends.

A154. The prosthetic device of any of paragraphs A152-A153, wherein the extension fixed line is configured to pass through a/the independent counter posterior to a/the one or more interface pads of the independent counter.

A155. The prosthetic device of any of paragraphs A152-A154, wherein the extension fixed line is configured to tighten, or be placed under increased tension, under loading of the chassis, such that tensioning of the extension fixed line is configured to pull a/the posterior elbow pad into an olecranon fossa of the residual limb.

A156. The prosthetic device of any of paragraphs A152-A155, wherein the extension fixed line is configured to tighten, or be placed under increased tension, under loading of the chassis, thereby increasing compression of the socket around the residual limb.

A157. The prosthetic device of any of paragraphs A152-A156, wherein the extension fixed line is configured to create a set distance from an/the end effector attachment unit to a/the independent counter of the prosthetic device when the residual limb is at full extension.

A158. The prosthetic device of any of paragraphs A152-A157, wherein the extension fixed line extends proximally from the chassis to a/the independent counter, wherein the extension fixed line extends circumferentially along a/the posterior side of an/the upper textile socket of the socket, and wherein the extension fixed line further extends distally back to the chassis, terminating at an extension fixed line terminus.

A159. The prosthetic device of any of paragraphs A152-A158, wherein an origination region of the extension fixed line opposite a/the extension fixed line terminus is secured to the chassis via a set screw or other fastener, and wherein a set length of the extension fixed line can be lengthened or shortened by removing the set screw or other fastener and translating the origination region of the extension fixed line relative to the set screw or other fastener.

A160. The prosthetic device of any of paragraphs A152-A159, wherein the extension fixed line comprises plastic tubing surrounding the extension fixed line.

A161. The prosthetic device of any of paragraphs A1-A160, wherein the selective adjustment system comprises a/the flexion fixed line.

A162. The prosthetic device of paragraph A161, wherein the flexion fixed line is configured to create a set distance between an/the end effector attachment unit to a/the independent counter of the prosthetic device when the residual limb is at full flexion.

A163. The prosthetic device of any of paragraphs A161-A162, wherein the flexion fixed line comprises a medial portion that extends proximally along a/the medial side of a/the lower textile socket of the socket and an/the upper textile socket of the socket, and wherein the flexion fixed line comprises a lateral portion that extends proximally along a/the lateral side of the lower textile socket and a/the lateral side of the upper textile socket.

A164. The prosthetic device of any of paragraphs A161-A163, wherein a proximal end region of the flexion fixed line is fixed to an/the upper textile socket of the socket.

A165. The prosthetic device of any of paragraphs A161-A164, wherein an origination region of the flexion fixed line is secured to the chassis via a/the set screw or other fastener, and wherein a set length of the flexion fixed line can be lengthened or shortened by removing the set screw or other fastener and translating the origination region of the flexion fixed line relative to the set screw or other fastener.

A166. The prosthetic device of any of paragraphs A152-A165, further comprising a ratcheted spool operatively coupled to a/the flexion fixed line and/or the extension fixed line, wherein the ratcheted spool is configured for micro-adjustments of a set length of the flexion fixed line and/or for micro-adjustments of a set length of the extension fixed line.

A167. The prosthetic device of any of paragraphs A1-A166, wherein the selective adjustment system comprises a first lace configured to automatically increase in tension in response to extension of the residual limb, thereby limiting slip of the prosthetic device on the residual limb, and wherein the first lace is further configured to automatically decrease in tension in response to flexion of the residual limb.

A168. The prosthetic device of any of paragraphs A1-A167, wherein the selective adjustment system comprises a second lace configured to automatically increase in tension in response to flexion of the residual limb, thereby limiting slip of the prosthetic device on the residual limb, and wherein the second lace is further configured to automatically decrease in tension in response to extension of the residual limb.

A169. The prosthetic device of any of paragraphs A1-A168, wherein the selective adjustment system comprises at least one adjustable lace.

A170. The prosthetic device of paragraph A169, wherein the at least one adjustable lace comprises a/the top lace and a/the balancing lace.

A171. The prosthetic device of any of paragraphs A1-A170, wherein the selective adjustment system comprises a/the at least one fixed line having a set length.

A172. The prosthetic device of paragraph A171, wherein the at least one fixed line comprises an/the extension fixed line and a/the flexion fixed line.

A173. The prosthetic device of any of paragraphs A1-A172, wherein an/the extension fixed line, a/the flexion fixed line, a/the top lace, and/or a/the balancing lace comprise low-friction, small diameter cables, wires, fibers, or laces.

A174. The prosthetic device of any of paragraphs A1-A173, wherein the selective adjustment system comprises an anterior-most internal lace guide that exits a respective elongate counter of the plurality of elongate counters.

A175. The prosthetic device of paragraph A174, wherein the selective adjustment system comprises an anterior-most internal lace guide that enters a/the independent counter of the prosthetic device.

A176. The prosthetic device of paragraph A175, wherein the selective adjustment system comprises at least one internal lace guide in the independent counter that is posterior to an imaginary line connecting the anterior-most internal lace guide of the respective elongate counter and the anterior-most internal lace guide of the independent counter.

A177. The prosthetic device of any of paragraphs A1-A176, wherein the prosthetic device is configured to engage the residual limb, and the residual limb is the result of one or more selected from the group comprising a transfemoral amputation, a transtibial amputation, a hip disarticulation, a transhumeral amputation, and a shoulder disarticulation.

A178. The prosthetic device of any of paragraphs A1-A177, wherein the plurality of elongate counters on an/the anterior side of the residual limb are configured to terminate distal to an area enveloped by elbow flexion of the residual limb.

A179. The prosthetic device of any of paragraphs A1-A178, wherein the plurality of elongate counters on an/the anterior side of the residual limb are configured to avoid a/the cubital fold region of the residual limb.

A180. The prosthetic device of any of paragraphs A1-A179, wherein the plurality of elongate counters are configured to selectively avoid areas of the residual limb as needed to preserve a/the range of motion of the residual limb.

A181. The prosthetic device of any of paragraphs A1-A180, wherein the plurality of elongate counters on an/the posterior side of the residual limb are configured to avoid a popliteal fossa of the residual limb.

A182. The prosthetic device of any of paragraphs A1-A181, wherein at least one elongate counter of the plurality of elongate counters is configured to resist motion relative to the residual limb on heel-strike while walking.

A183. The prosthetic device of any of paragraphs A1-A182, wherein at least one elongate counter of the plurality of elongate counters is configured to resist motion relative to the residual limb on toe-off while walking.

A184. The prosthetic device of any of paragraphs A1-A183, wherein a/the keyed-rail system comprises one or more sew tabs configured to aid in integrating one or more rails of the keyed-rail system into the socket.

A185. The prosthetic device of paragraph A184, wherein the one or more sew tabs are configured to be sewn through to attach the one or more rails to the socket.

A186. The prosthetic device of any of paragraphs A1-A185, configured for use with powered and myo-electric or nerve-directed wrist devices and terminal devices.

A187. The prosthetic device of any of paragraphs A1-A186, further comprising mounting for electronics and a powered wrist in the plurality of elongate counters.

A188. The prosthetic device of any of paragraphs A1-A187, further comprising the replacement of any technique of manufacturing textile components with that of engineered knitting, including 3D-knitting of functional structures and features including stretch or non-stretch regions, eyelets, lace guides and channels, and pockets for components.

B1. A system, comprising:

the prosthetic device of any of paragraphs A1-A188; and a/the harness configured to be worn by a/the patient while the prosthetic device is worn, wherein the harness is coupled to the prosthetic device and configured to reinforce securement of the prosthetic device to the residual limb.

B2. The system of paragraph B1, wherein the prosthetic device is coupled to the harness via a coupler configured to be selectively coupled and uncoupled using one hand.

B3. The system of paragraph B2, wherein the coupler is magnetic.

B4. The system of paragraph B2 or B3, wherein the coupler is fixed to the a/the independent counter of the prosthetic device.

B5. The system of any of paragraphs B2-B4, wherein the coupler is fixed to a/the back panel of the prosthetic device.

B6. The system of any of paragraphs B2-B5, wherein the coupler is fixed to the prosthetic device via a string, a cord, a lace, a fiber, and/or a cable.

B7. The system of any of paragraphs B1-B6, wherein the harness comprises at least one portion comprising a stretch material and at least a second portion comprising a non-stretch material.

B8. The system of any of paragraphs B1-B7, wherein the harness is configured to stretch around a perimeter edge region of the harness, and wherein the harness is configured to be static in areas of a harness interior to the perimeter edge region.

B9. The system of any of paragraphs B1-B8, further comprising a/the terminal device, an/the end effector, a/the leg pylon, a/the leg end effector, and/or a/the prosthetic foot, wherein a/the end effector attachment unit of the prosthetic device is configured to selectively and removably receive any one of the terminal device, the end effector, the leg pylon, the leg end effector, or the prosthetic foot, at a time.

B10. The system of any of paragraphs B1-B9, wherein the chassis comprises an/the end effector attachment unit configured to receive a/the terminal device, an/the end effector, a/the leg end effector, a/the leg pylon, and/or a/the prosthetic foot.

B11. The system of paragraph B10, wherein the end effector attachment unit is positioned within a/the distal end region of the chassis, such that the chassis is configured to operatively and removably couple the terminal device, the end effector, the leg end effector, the leg pylon, and/or the prosthetic foot to the residual limb via the prosthetic device.

B12. The system of paragraph B10 or B11, wherein the end effector attachment unit is selectively adjustable between a/the lock configuration, a/the caster configuration, and a/the release configuration.

B13. The system of any of paragraphs B10-B12, wherein in the lock configuration, the end effector attachment unit is configured to secure the terminal device, the end effector, the leg end effector, the leg pylon, and/or the prosthetic foot with respect to the chassis such that the terminal device, the end effector, the leg end effector, the leg pylon, and/or the prosthetic foot has a/the fixed position and orientation with respect to the chassis.

B14. The system of any of paragraphs B10-613, wherein in the caster configuration, the end effector attachment unit is configured to secure the terminal device, the end effector, the leg end effector, the leg pylon, and/or the prosthetic foot with respect to the chassis such that the terminal device, the end effector, the leg end effector, the leg pylon, and/or the prosthetic foot is free to rotate with respect to the chassis.

B15. The system of any of paragraphs B10-1314, wherein in the release configuration, the end effector attachment unit is configured to release the terminal device, the end effector, the leg end effector, the leg pylon, and/or the prosthetic foot such that the terminal device, the end effector, the leg end effector, the leg pylon, and/or the prosthetic foot may be selectively removed from the chassis.

B16. The system of any of paragraphs B10-B15, wherein the end effector attachment unit is configured to be selectively transitioned to the lock configuration, the caster configuration, or the release configuration by rotating the end effector attachment unit relative to the plurality of elongate counters.

C1. A method of making a prosthetic device for a given residual limb, the method comprising:

performing a 3D-scan of the given residual limb;

creating a computer-aided design (CAD) model of the given residual limb; and forming a plurality of elongate counters and an independent counter of the prosthetic device of any of paragraphs A1-A188 using the CAD model of the given residual limb, wherein the plurality of elongate counters and the independent counter are custom-sized and shaped for the given residual limb.

C2. The method of paragraph C1, wherein the forming the plurality of elongate counters comprises 3D-printing the plurality of elongate counters and the independent counter.

C3. The method of any of paragraphs C1-C2, further comprising forming a plurality of textile pattern pieces to form an/the upper textile socket of the socket and a/the lower textile socket of the socket, wherein the plurality of textile pattern pieces are custom-sized and shaped for the given residual limb using the CAD model of the given residual limb.

C4. The method of paragraph C3, further comprising coupling the plurality of elongate counters to the lower textile socket and coupling the independent counter to the upper textile socket.

C5. The method of any of paragraphs C1-C4, wherein the forming the plurality of elongate counters comprises building in an offset into a proximal portion of the plurality of elongate counters, wherein the offset is configured to account for a thickness of a/the lower textile socket of the socket.

C6. The method of any of paragraphs C1-05, wherein the forming the plurality of elongate counters comprises determining a respective contact length for each respective elongate counter of the plurality of elongate counters using the CAD model of the given residual limb.

C7. The method of any of paragraphs C1-C6, further comprising determining a placement, a form, a density, and a scale of a/the plurality of interface pads, such that the plurality of interface pads are configured to create effective and comfortable suspension for the given residual limb.

C8. The method of any of paragraphs C1-C7, further comprising determining an arm length by determining a distance from a/the lateral epicondyle of a/the patient to an/the end effector attachment unit of the prosthetic device with a terminal device offset.

C9. The method of any of paragraphs C1-C8, further comprising rotating an/the end effector attachment unit, thereby removing a/the terminal device, an/the end effector, a/the leg end effector, a/the leg pylon, and/or a/the prosthetic foot.

C10. The method of any of paragraphs C1-C9, further comprising placing a/the terminal device, an/the end effector, a/the leg end effector, a/the leg pylon, and/or a/the prosthetic foot partially within an/the end effector attachment unit of the prosthetic device, thereby securing the terminal device, the end effector, the leg end effector, the leg pylon, and/or the prosthetic foot to the chassis.

C11. The method of any of paragraphs C1-C10, further comprising laminating one or more layers of a/the lower textile socket of the socket.

C12. The method of any of paragraphs C1-C11, further comprising laminating one or more layers of an/the upper textile socket of the socket.

C13. The method of any of paragraphs C1-C12, further comprising sewing a mapped and flattened textile into a 3D-shape, thereby forming a/the lower textile socket of the socket.

C14. The method of any of paragraphs C1-C13, further comprising creating a mapped and flattened engineered knit textile, designed to be sewn into a 3D shape, thereby forming a/the lower textile socket and/or a/the upper textile socket of the socket.

C15. The method of any of paragraphs C1-C14, further comprising creating a mapped and engineered knit textile, knit directly into a 3D-shape, or into a flatknit shape with 3D-extensions and regions, thereby forming a/the lower textile socket and/or a/the upper textile socket of the socket.

D1. The use of the prosthetic device of any of paragraphs A1-A188 and/or the system of any of paragraphs B1-B16 to operatively couple a/the terminal device, an/the end effector, a/the leg end effector, a/the leg pylon, and/or a/the prosthetic foot to a/the residual limb.

As used herein, the terms "selective" and "selectively," when modifying an action, movement, configuration, or other activity of one or more components or characteristics of an apparatus, mean that the specific action, movement, configuration, or other activity is a direct or indirect result of dynamic processes and/or user manipulation of an aspect of, or one or more components of, the apparatus. The terms "selective" and "selectively" thus may characterize an activity that is a direct or indirect result of user manipulation of an aspect of, or one or more components of, the apparatus, or may characterize a process that occurs automatically, such as via the mechanisms disclosed herein.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one example, to at least one, optionally including more than one, A, with no B present (and optionally including entities other than B); in another example, to at least one, optionally including more than one, B, with no A present (and optionally including entities other than A); in yet another example, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" may mean A alone, B alone, C alone, A and B together, A and C together, B and C together, or A, B, and C together, and optionally any of the above in combination with at least one other entity.

As used herein, the phrase "at least substantially," when modifying a degree or relationship, includes not only the recited "substantial" degree or relationship, but also the full extent of the recited degree or relationship. A substantial amount of a recited degree or relationship may include at least 75% of the recited degree or relationship. For example, a first direction that is at least substantially parallel to a second direction includes a first direction that is within an angular deviation of 22.5° relative to the second direction and also includes a first direction that is identical to the second direction.

FIGS. 5-11, 13-16, 18-31, and 33-37 are shown approximately to scale. Surfaces depicted as contacting each other may be in direct contact with one another. The term "on" may refer to face-sharing contact.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

As used herein, the phrase, "for example," the phrase, "as an example," and/or simply the term "example," when used with reference to one or more components, features, details, structures, examples, and/or methods according to the present disclosure, are intended to convey that the described component, feature, detail, structure, example, and/or method is an illustrative, non-exclusive example of components, features, details, structures, examples, and/or methods according to the present disclosure. Thus, the described component, feature, detail, structure, example, and/or method is not intended to be limiting, required, or exclusive/exhaustive; and other components, features, details, structures, examples, and/or methods, including structurally and/or functionally similar and/or equivalent components, features, details, structures, examples, and/or methods, are also within the scope of the present disclosure.

The invention claimed is:

1. A prosthetic device for engaging a residual limb, the prosthetic device comprising:

a plurality of elongate counters extending proximally from a chassis and configured to receive at least a portion of the residual limb within a volume defined by the plurality of elongate counters, wherein each respective elongate counter of the plurality of elongate counters is configured to counteract forces applied to the residual limb via the prosthetic device;

a socket configured to engage with the residual limb, wherein the socket comprises:

a lower textile socket coupled to the plurality of elongate counters; and an upper textile socket coupled to the lower textile socket; and a selective adjustment system configured to secure the prosthetic device to the residual limb and configured to provide selective adjustment of compression of the socket around the residual limb, wherein the selective adjustment system is configured to function as one or more flexible hinges.

2. The prosthetic device according to claim 1, wherein the prosthetic device is configured such that a dynamic volume is created within the socket, wherein the dynamic volume is configured to account for and accommodate changes in shape of the residual limb through a range of motion of the residual limb.

3. The prosthetic device according to claim 1, wherein the socket is configured to tighten around the residual limb if forces applied to a distal end region of the chassis cause the socket to be pulled away from the residual limb.

4. The prosthetic device according to claim 1, wherein the socket is breathable and moisture-wicking.

5. The prosthetic device according to claim 1, wherein the plurality of elongate counters are configured to be customized for individual patients, and wherein a contact length of each respective elongate counter is patient-specific.

6. The prosthetic device according to claim 1, wherein the plurality of elongate counters comprises a plurality of forearm counters that are configured to be positioned surrounding a residual forearm of a patient, and wherein the plurality of forearm counters are configured to terminate distal to a cubital fold region of the patient when the prosthetic device is donned.

7. The prosthetic device according to claim 1, wherein the plurality of elongate counters comprises a keyed-rail system and fixing hardware, wherein the lower textile socket of the socket is coupled to each respective elongate counter of the plurality of elongate counters via the keyed-rail system, and wherein the keyed-rail system comprises:

a recessed track formed in an inner counter surface of each respective elongate counter of the plurality of elongate counters; and a plurality of rails protruding from the lower textile socket, wherein each respective rail of the plurality of rails is configured to slide into a respective recessed track of a respective elongate counter.

8. The prosthetic device according to claim 1, wherein the lower textile socket comprises one or more interface pads configured to provide cushioning for one or more bony prominences of the residual limb, wherein the one or more interface pads are configured to be positioned between the plurality of elongate counters and the residual limb.

9. The prosthetic device according to claim 8, wherein the one or more interface pads comprise one or more forearm interface pads, wherein the one or more forearm interface pads comprise an elongate portion configured to be positioned to extend substantially parallel to a radius of the residual limb and an ulna of the residual limb, and wherein the one or more forearm interface pads comprise a curved portion configured to be positioned such that the curved portion extends substantially perpendicularly to the radius of the residual limb and the ulna of the residual limb.

10. The prosthetic device according to claim 1, wherein the lower textile socket comprises:

an outer layer comprising a plurality of lace guides for receiving one or more laces of the selective adjustment system therethrough;

a middle layer comprising a plurality of spaced-apart reinforcement strips configured to reinforce the lower textile socket, and wherein the middle layer further comprises one or more elastic straps positioned and configured to provide localized areas of extra stretch in the lower textile socket; and an inner liner comprising a first liner layer and a second liner layer, wherein the first liner layer and the second liner layer are laminated together, and wherein the inner liner comprises at least one interface pad positioned between the first liner layer and the second liner layer.

11. The prosthetic device according to claim 1, wherein the upper textile socket is positioned at least partially within the lower textile socket, and wherein the upper textile socket is coupled to an inner socket surface of the lower textile socket.

12. The prosthetic device according to claim 1, wherein the upper textile socket comprises four-way stretch material, and wherein the upper textile socket comprises a cutout to receive a joint of the residual limb.

13. The prosthetic device according to claim 1, wherein the upper textile socket comprises:

an upper socket liner configured to engage with the residual limb, wherein the upper socket liner comprises one or more interface pads;

an upper socket middle layer, wherein the upper socket middle layer comprises an elastic strap extending circumferentially around a proximal opening of the upper socket middle layer, wherein the proximal opening is configured to receive the residual limb therethrough, and wherein the elastic strap is configured to help secure the upper textile socket around the residual limb; and an upper socket outer layer, wherein the upper socket middle layer is sandwiched between the upper socket outer layer and the upper socket liner, and wherein the upper socket outer layer is configured to engage with an independent counter of the prosthetic device, wherein the upper socket outer layer is positioned proximal to the plurality of elongate counters.

14. The prosthetic device according to claim 13, wherein the upper socket outer layer comprises a back panel, the back panel comprising:

an interface support pad configured to support an olecranon fossa of the residual limb;

a proximal tensioning reel configured to adjust a tension of at least a portion of the selective adjustment system; and a posterior socket pull loop configured to aid in donning the prosthetic device.

15. The prosthetic device according to claim 1, wherein the selective adjustment system is configured to provide selective adjustment of compression of the lower textile socket of the socket and the upper textile socket of the socket independently from one another around the residual limb.

16. The prosthetic device according to claim 1, wherein the prosthetic device is configured to engage the residual limb, and the residual limb is the result of one or more selected from the group comprising a transfemoral amputation, a transtibial amputation, a hip disarticulation, a transhumeral amputation, or a shoulder disarticulation.

17. A prosthetic device for engaging a residual limb, the prosthetic device comprising:

a plurality of elongate counters extending proximally from a chassis and configured to receive at least a portion of the residual limb within a volume defined by the plurality of elongate counters, wherein each respective elongate counter of the plurality of elongate counters is configured to counteract forces applied to the residual limb via the prosthetic device;

a socket configured to engage with the residual limb; and a selective adjustment system configured to secure the prosthetic device to the residual limb and configured to provide selective adjustment of compression of the socket around the residual limb, wherein the selective adjustment system comprises at least one fixed line having a predetermined length and at least one lace having a selectively adjustable length, wherein the selective adjustment system is configured to function as one or more flexible hinges.

18. The prosthetic device according to claim 17, wherein the chassis comprises an end effector attachment unit, and wherein the prosthetic device further comprises an independent counter, wherein the independent counter is positioned proximal to the plurality of elongate counters, and wherein the end effector attachment unit is configured to receive and operatively couple to the chassis one or more selected from the group comprising a terminal device, an end effector, a leg end effector, a leg pylon, and a prosthetic foot.

19. The prosthetic device according to claim 18, wherein the end effector attachment unit is positioned within a distal end region of the chassis such that the chassis is configured to operatively and removably couple one or more of the terminal device, the end effector, the leg end effector, the leg pylon, and the prosthetic foot to the residual limb.

20. The prosthetic device according to claim 18, wherein the end effector attachment unit is selectively adjustable between a lock configuration, a caster configuration, and a release configuration, wherein in the lock configuration, the end effector attachment unit is configured to secure one or more of the terminal device, the end effector, the leg end effector, the leg pylon, and the prosthetic foot with respect to the chassis such that the terminal device, the end effector, the leg end effector, the leg pylon, and/or the prosthetic foot has a fixed position and orientation with respect to the chassis, wherein in the caster configuration, the end effector attachment unit is configured to secure one or more of the terminal device, the end effector, the leg end effector, the leg pylon, and the prosthetic foot with respect to the chassis such that the terminal device, the end effector, the leg end effector, the leg pylon, and/or the prosthetic foot is free to rotate with respect to the chassis, and wherein in the release configuration, the end effector attachment unit is configured to release one or more of the terminal device, the end effector, the leg end effector, the leg pylon, and the prosthetic foot such that the terminal device, the end effector, the leg end effector, the leg pylon, and/or the prosthetic foot may be selectively removed from the chassis.

21. The prosthetic device according to claim 20, wherein the end effector attachment unit is configured to be selectively transitioned to the lock configuration, the caster configuration, or the release configuration by rotating the end effector attachment unit relative to the plurality of elongate counters.

22. The prosthetic device according to claim 18, wherein the at least one fixed line of the selective adjustment system comprises:

an extension fixed line configured to tighten, or be placed under increased tension, under loading of the chassis, thereby increasing compression of the socket around the residual limb, wherein the extension fixed line is configured to create a first set distance from the end effector attachment unit to the independent counter when the residual limb is at full extension; and a flexion fixed line configured to create a second set distance from the end effector attachment unit to the independent counter when the residual limb is at full flexion.

23. The prosthetic device according to claim 18, wherein the at least one lace of the selective adjustment system comprises:

a top lace engaged with the independent counter and the plurality of elongate counters such that when the top lace is tightened, the top lace pulls together a subset of the plurality of elongate counters positioned on an anterior side of the prosthetic device; and a balancing lace configured to pull the independent counter towards the plurality of elongate counters and draw the residual limb into the socket as the balancing lace is tightened.

24. The prosthetic device according to claim 23, wherein the top lace is configured to automatically increase in tension in response to extension of the residual limb, thereby limiting slip of the prosthetic device on the residual limb, and wherein the top lace is further configured to automatically decrease in tension in response to flexion of the residual limb, and wherein the balancing lace is configured to automatically increase in tension in response to flexion of the residual limb, thereby limiting slip of the prosthetic device on the residual limb, and wherein the balancing lace is further configured to automatically decrease in tension in response to extension of the residual limb.

25. The prosthetic device according to claim 23, wherein the independent counter comprises a proximal tensioning reel configured to adjust a tension of the top lace of the selective adjustment system, and wherein the chassis comprises a distal tensioning reel configured to adjust a tension in the balancing lace.

26. The prosthetic device according to claim 17, wherein the independent counter comprises a magnetic attachment point configured for selective coupling of the prosthetic device to a harness worn by a patient.

27. The prosthetic device according to claim 18, wherein the socket comprises:

a lower textile socket coupled to the plurality of elongate counters; and an upper textile socket coupled to the lower textile socket, wherein the independent counter is directly coupled to the upper textile socket of the socket.

28. The prosthetic device according to claim 18, wherein the independent counter comprises one or more internal lace guides extending through a thickness of the independent counter, wherein one or more laces of the selective adjustment system are configured to pass through the independent counter via the one or more internal lace guides.

29. The prosthetic device according to claim 17, wherein the socket comprises a plurality of layers that integrate with each other and with the plurality of elongate counters such that the socket is configured to reinforce a connection between the residual limb and a terminal device or an end effector coupled to the chassis.

30. The prosthetic device according to claim 17, wherein the socket comprises at least a first region comprising a stretch textile and at least a second region comprising a non-stretch textile.

31. A system comprising:

the prosthetic device according to claim 18; and a harness configured to be worn by a patient while the prosthetic device is worn, wherein the harness is coupled to the prosthetic device and configured to reinforce securement of the prosthetic device to the residual limb, and wherein the harness comprises at least one portion comprising a stretch fabric and at least a second portion comprising a non-stretch fabric.

32. The system according to claim 31, wherein the prosthetic device is coupled to the harness via a magnetic coupler configured to be selectively coupled and de-coupled using one hand, and wherein the magnetic coupler is fixed to the independent counter of the prosthetic device.

33. The system according to claim 31, wherein the harness is configured to stretch around a perimeter edge region of the harness, and wherein the harness is configured to be static in areas of a harness interior to the perimeter edge region.

34. The system according to claim 31, further comprising one or more selected from the group consisting of the terminal device, the end effector, the leg pylon, the leg end effector, and the prosthetic foot, wherein the end effector attachment unit of the prosthetic device is configured to selectively and removably receive any one of the terminal device, the end effector, the leg pylon, the leg end effector, or the prosthetic foot, at a time.

35. A method of making a prosthetic device for a given residual limb, wherein the prosthetic device is the prosthetic device according to claim 27, the method comprising:

performing a 3D-scan of the given residual limb;

creating a computer-aided design (CAD) model of the given residual limb;

forming the plurality of elongate counters and the independent counter of the prosthetic device according to claim 27 using the CAD model of the given residual limb, wherein the plurality of elongate counters and the independent counter are custom-sized and shaped for the given residual limb;

forming a plurality of textile pattern pieces to form the upper textile socket and the lower textile socket of the socket of the prosthetic device according to claim 27, wherein the plurality of textile pattern pieces are custom-sized and shaped for the given residual limb using the CAD model of the given residual limb;

coupling the lower textile socket to the plurality of elongate counters;

coupling the upper textile socket to the lower textile socket, such that the independent counter is directly coupled to the upper textile socket; and forming the selective adjustment system configured to secure the prosthetic device to the residual limb such that the selective adjustment system is configured to provide selective adjustment of compression of the socket around the residual limb, wherein the forming the selective adjustment system comprises forming the at least one fixed line having the predetermined length and the at least one lace having the selectively adjustable length, wherein the selective adjustment system is configured to function as the one or more flexible hinges;

wherein the plurality of elongate counters extend from the chassis of the prosthetic device according to claim 27, wherein the chassis comprises the end effector attachment unit, and wherein the end effector attachment unit is configured to receive and operatively couple to the chassis the one or more selected from the group comprising the terminal device, the end effector, the legend effector, the leg pylon, and the prosthetic foot.

36. The method according to claim 35, further comprising:

determining a placement, a form, a density, and a scale of a plurality of interface pads, such that the plurality of interface pads are configured to create effective and comfortable suspension for the given residual limb.

37. The method according to claim 35, further comprising rotating the end effector attachment unit, thereby removing the terminal device, the end effector, the leg end effector, the leg pylon, or the prosthetic foot from the end effector attachment unit.

* * * * *